US010435398B2

(12) United States Patent
Kuduk et al.

(10) Patent No.: US 10,435,398 B2
(45) Date of Patent: Oct. 8, 2019

(54) OXAZOLE OREXIN RECEPTOR ANTAGONISTS

(71) Applicant: MERCK SHARP & DOHME CORP., Rahway, NJ (US)

(72) Inventors: Scott D. Kuduk, Harleysville, PA (US); Nigel Liverton, Harleysville, PA (US); Yunfu Luo, Shanghai (CN)

(73) Assignee: Merck Sharp & Dohme Corp., Rathaway, NJ (US)

( * ) Notice: Subject to any disclaimer, the term of this patent is extended or adjusted under 35 U.S.C. 154(b) by 25 days.

(21) Appl. No.: 15/523,247

(22) PCT Filed: Oct. 27, 2015

(86) PCT No.: PCT/US2015/057442
§ 371 (c)(1),
(2) Date: Apr. 28, 2017

(87) PCT Pub. No.: WO2016/069515
PCT Pub. Date: May 6, 2016

(65) Prior Publication Data
US 2017/0320865 A1    Nov. 9, 2017

(30) Foreign Application Priority Data

Oct. 30, 2014  (WO) ................ PCT/CN2014/089931

(51) Int. Cl.
*C07D 413/12* (2006.01)
*C07D 413/14* (2006.01)
*C07D 263/32* (2006.01)

(52) U.S. Cl.
CPC ......... *C07D 413/14* (2013.01); *C07D 263/32* (2013.01); *C07D 413/12* (2013.01)

(58) Field of Classification Search
CPC .................................................. C07D 413/12
See application file for complete search history.

(56) References Cited

U.S. PATENT DOCUMENTS

| | | |
|---|---|---|
| 7,951,797 B2 | 5/2011 | Breslin et al. |
| 8,242,121 B2 | 8/2012 | Coleman et al. |
| 8,263,586 B2 | 9/2012 | Cox et al. |
| 8,349,872 B2 | 1/2013 | Coleman et al. |
| 8,357,700 B2 | 1/2013 | Cox et al. |
| 8,357,709 B2 | 1/2013 | Coleman et al. |
| 8,362,009 B2 | 1/2013 | Bergman et al. |
| 8,399,494 B2 | 3/2013 | Bergman et al. |
| 8,466,281 B2 | 6/2013 | Coleman et al. |
| 8,618,102 B2 | 12/2013 | Coleman et al. |
| 8,623,863 B2 | 1/2014 | Coleman et al. |
| 8,669,272 B2 | 3/2014 | Breslin et al. |
| 8,685,961 B2 | 4/2014 | Brashear et al. |
| 8,710,076 B2 | 4/2014 | Breslin et al. |
| 8,940,898 B2 | 1/2015 | Kuduk et al. |
| 9,029,364 B2 | 5/2015 | Kuduk et al. |
| 9,156,819 B2 | 10/2015 | Kuduk et al. |
| 9,546,152 B2 | 1/2017 | Kuduk et al. |
| 9,550,786 B2 | 1/2017 | Cooke et al. |
| 9,556,145 B2 | 1/2017 | Kuduk et al. |
| 9,556,190 B2 | 1/2017 | Kuduk et al. |
| 9,586,934 B2 | 3/2017 | Kuduk et al. |
| 9,586,950 B2 | 3/2017 | Kuduk et al. |
| 9,617,246 B2 | 4/2017 | Kuduk et al. |
| 9,624,197 B2 | 4/2017 | Kuduk et al. |
| 2006/0047000 A1 | 3/2006 | Druzgala et al. |
| 2010/0029736 A1 | 2/2010 | Cox et al. |
| 2010/0093690 A1 | 4/2010 | Bruce et al. |
| 2011/0195957 A1 | 8/2011 | Bergman et al. |
| 2012/0196901 A1 | 8/2012 | Coleman et al. |
| 2013/0059883 A1 | 3/2013 | Baloglu et al. |
| 2013/0281465 A1 | 10/2013 | Nozawa et al. |
| 2015/0322039 A1 | 11/2015 | Kuduk et al. |
| 2015/0322040 A1 | 11/2015 | Kuduk et al. |
| 2015/0322041 A1 | 11/2015 | Kuduk et al. |
| 2016/0016935 A1 | 1/2016 | Kuduk et al. |
| 2016/0068510 A1 | 3/2016 | Kuduk et al. |

(Continued)

FOREIGN PATENT DOCUMENTS

| | | | | |
|---|---|---|---|---|
| WO | WO-2007107539 A1 * | 9/2007 | ............ | C07D 231/56 |
| WO | WO-2009043889 A2 * | 4/2009 | ............ | C07D 263/32 |

(Continued)

OTHER PUBLICATIONS

Mayo Clinic. "Insomnia." © 2018. Available from: < https://www.mayoclinic.org/diseases-conditions/insomnia/symptoms-causes/syc-20355167 >.*

Chumachenko, S.A., et al. "Synthesis and Some Properties of 5-Alkylamino-2-(phthalinmidoalkyl)-1,3-oxazole-4-carbonitriles." Chemistry of Heterocyclic Compounds. (Nov. 2011), vol. 47, No. 8, pp. 1020-1028. (Year: 2011).*

Anthony J. Roecker et al, Orexin Receptor Antagonists: New Therapeutic Agents for the Treatment of Insomnia, Journal of Medicinal Chemistry, 2016, 504-530, 59(2).

Jason W. Skudlarek et al., Investigation of orexin-2 selective receptor antagonists: Structural modifications resulting in dual orexin receptor antagonists, Bioorganic & Medicinal Chemistry Letters, 2017, 1364-1370, 27(6).

(Continued)

*Primary Examiner* — Andrew D Kosar
*Assistant Examiner* — John S Kenyon
(74) *Attorney, Agent, or Firm* — J. Eric Thies; John C. Todaro

(57) ABSTRACT

The present invention is directed to oxazole compounds which are antagonists of orexin receptors. The present invention is also directed to uses of the oxazole compounds described herein in the potential treatment or prevention of neurological and psychiatric disorders and diseases in which orexin receptors are involved. The present invention is also directed to pharmaceutical compositions comprising these compounds. The present invention is also directed to uses of these pharmaceutical compositions in the potential prevention or treatment of such diseases in which orexin receptors are involved.

13 Claims, No Drawings

(56) References Cited

U.S. PATENT DOCUMENTS

| | | |
|---|---|---|
| 2016/0068514 A1 | 3/2016 | Kuduk |
| 2016/0102073 A1 | 4/2016 | Kuduk et al. |
| 2016/0176858 A1 | 6/2016 | Liverton et al. |
| 2016/0185768 A1 | 6/2016 | Liverton et al. |
| 2016/0304490 A1 | 10/2016 | Kuduk et al. |
| 2016/0318900 A1 | 11/2016 | Kuduk et al. |
| 2016/0318923 A1 | 11/2016 | Kuduk et al. |

FOREIGN PATENT DOCUMENTS

| | | |
|---|---|---|
| WO | WO20100051238 | 5/2010 |
| WO | WO2013009810 | 1/2013 |
| WO | WO2016069510 | 5/2016 |
| WO | WO2016069512 | 5/2016 |
| WO | WO2016069515 | 5/2016 |
| WO | WO2016069517 | 5/2016 |
| WO | WO2016069519 | 5/2016 |
| WO | WO2016085783 | 6/2016 |
| WO | WO2016085784 | 6/2016 |
| WO | WO2016089721 | 6/2016 |
| WO | WO2016089722 | 6/2016 |
| WO | WO2016100154 | 6/2016 |
| WO | WO2016100156 | 6/2016 |
| WO | WO2016100157 | 6/2016 |
| WO | WO2016100161 | 6/2016 |
| WO | WO2016100162 | 6/2016 |
| WO | WO2016106105 | 6/2016 |
| WO | WO2016106106 | 6/2016 |

OTHER PUBLICATIONS

Meggs et al, Neurogenic Switching: A Hypothesis for a Mechanism for Shifting the Site of Inflammation in Allergy and Chemical Sensitivity, Environmental Health Perspective, 1995, 54-56, 103(1).

* cited by examiner

OXAZOLE OREXIN RECEPTOR ANTAGONISTS

CROSS REFERENCE TO RELATED APPLICATIONS

This application is a U.S. National Phase application under 35 U.S.C. § 371 of PCT Application No. PCT/US2015/057442, filed Oct. 27, 2015, which claims priority from PCT Application No. PCT/CN2014/089931, filed Oct. 30, 2014.

BACKGROUND OF THE INVENTION

The orexins (hypocretins) comprise two neuropeptides produced in the hypothalamus: orexin A (OX-A) (a 33 amino acid peptide) and orexin B (OX-B) (a 28 amino acid peptide) (Sakurai T. et al., Cell, 1998, 92, 573-585). Orexins are found to stimulate food consumption in rats, suggesting a physiological role for these peptides as mediators in the central feedback mechanism that regulates feeding behavior (Sakurai T. et al., Cell, 1998, 92, 573-585). Orexins regulate states of sleep and wakefulness opening potentially novel therapeutic approaches for narcoleptic or insomniac patients (Chemelli R. M. et al., Cell, 1999, 98, 437-451). Orexins have also been indicated as playing a role in arousal, reward, learning and memory (Harris, et al., Trends Neurosci., 2006, 29 (10), 571-577). Two orexin receptors have been cloned and characterized in mammals. They belong to the super family of G-protein coupled receptors (Sakurai T. et al., Cell, 1998, 92, 573-585): the orexin-1 receptor (OX or OX1R) is selective for OX-A, and the orexin-2 receptor (OX2 or OX2R) is capable of binding OX-A as well as OX-B. The physiological actions in which orexins are presumed to participate are thought to be expressed via one or both of OX1 receptor and OX2 receptor as the two subtypes of orexin receptors.

SUMMARY OF THE INVENTION

The present invention is directed to oxazole compounds which are antagonists of orexin receptors. The present invention is also directed to uses of the oxazole compounds described herein in the potential treatment or prevention of neurological and psychiatric disorders and diseases in which orexin receptors are involved. The present invention is also directed to pharmaceutical compositions comprising these compounds. The present invention is also directed to uses of these pharmaceutical compositions in the potential prevention or treatment of diseases in which orexin receptors are involved.

DETAILED DESCRIPTION OF THE INVENTION

The oxazole compounds having formula I below are orexin antagonists:

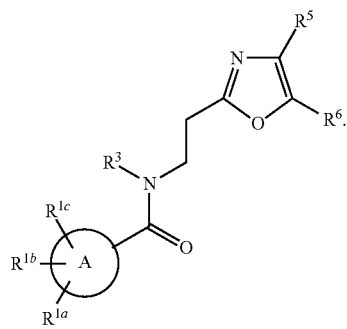

In the compounds of Formula I:
A is phenyl, naphthyl or heteroaryl;
$R^{1a}$, $R^{1b}$, and $R^{1c}$ are independently:
 (1) hydrogen,
 (2) halogen,
 (3) hydroxy,
 (4) —(C═O)$_m$O$_n$C$_{1-6}$alkyl, where m is 0 or 1, n is 0 or 1 (wherein if m is 0 or n is 0, a bond is present) and where alkyl is unsubstituted or substituted with 1-5 substituents independently selected from $R^4$,
 (5) —(C═O)$_m$O$_n$C$_{3-6}$cycloalkyl, where cycloalkyl is unsubstituted or substituted with 1-5 substituents independently selected from $R^4$,
 (6) —(C═O)$_m$C$_{2-4}$alkenyl, where alkenyl is unsubstituted or substituted with 1-5 substituents independently selected from $R^4$,
 (7) —(C═O)$_m$C$_{2-4}$alkynyl, where alkynyl is unsubstituted or substituted with 1-5 substituents independently selected from $R^4$,
 (8) —(C═O)$_m$O$_n$-phenyl or —(C═O)$_m$—O$_n$-naphthyl, where phenyl or naphthyl is unsubstituted or substituted with 1-5 substituents independently selected from $R^4$,
 (9) —(C═O)$_m$O$_n$-heterocycle, where the heterocycle is unsubstituted or substituted with 1-5 substituents independently selected from $R^4$,
 (10) —(C═O)$_m$NR$^{10}$R$^{11}$,
 (11) —S(O)$_2$NR$^{10}$R$^{11}$,
 (12) —S(O)$_q$R$^{12}$, where q is 0, 1 or 2 and where $R^{12}$ is selected from the definitions of $R^{10}$ and $R^{11}$,
 (13) —CO$_2$H,
 (14) —CN, or
 (15) —NO$_2$;
$R^3$ is C$_{1-6}$alkyl, C$_{2-6}$alkenyl, or C$_{3-6}$cycloalkyl, wherein $R^3$ is unsubstituted or substituted with 1-5 substituents independently selected from $R^4$;
Each $R^4$ is independently:
 (1) hydroxyl,
 (2) halogen,
 (3) C$_{1-6}$alkyl, optionally substituted with 1-5 halogens,
 (4) —C$_{3-6}$cycloalkyl,
 (5) —O—C$_{1-6}$alkyl, optionally substituted with 1-5 halogens,
 (6) —O(C═O)—C$_{1-6}$alkyl,
 (7) —NH$_2$,
 (8) —NH—C$_{1-6}$alkyl,
 (9) —NO$_2$,
 (10) phenyl,
 (11) heterocycle,
 (12) —CO$_2$H, or
 (13) —CN;

$R^5$ and $R^6$ are independently:
(1) hydrogen,
(2) halogen,
(3) —$C_{1-6}$alkyl, which is unsubstituted or substituted with 1-5 groups which are independently selected from halogen, hydroxy, —$OC_{1-3}$alkyl, —$NH_2$, —$NHC_{1-3}$alkyl, and —(C=O)$OC_{1-3}$alkyl,
(4) $C_{3-6}$cycloalkyl, which is unsubstituted or substituted with 1-5 groups which are independently $C_{1-3}$alkyl, halogen, hydroxy, —$OC_{1-3}$alkyl, —$NH_2$, —$NHC_{1-3}$alkyl, or —(C=O)$OC_{1-3}$alkyl,
(5) —$OC_{1-3}$alkyl, which is unsubstituted or substituted with 1-5 groups which are independently selected from halogen, hydroxy, —$OC_{1-3}$alkyl, —$NH_2$, —$NHC_{1-3}$alkyl, or —(C=O)$OC_{1-3}$alkyl,
(6) —(C=O)$OC_{1-3}$alkyl, which is unsubstituted or substituted with 1-5 halogens,
(7) —CN,
(8) —(C=O)$NH_2$, or
(9) —(C=O)$NHC_{1-3}$alkyl; and $R^{10}$ and $R^{11}$ are independently:
(a) hydrogen,
(b) $C_{1-6}$alkyl, which is unsubstituted or substituted with 1-4 groups independently selected from $R^4$,
(c) $C_{3-6}$alkenyl, which is unsubstituted or substituted with 1-4 groups independently selected from $R^4$,
(d) $C_{3-6}$alkynyl, which is unsubstituted or substituted with 1-4 groups independently selected from $R^4$,
(e) $C_{3-6}$cycloalkyl which is unsubstituted or substituted with 1-4 groups independently selected from $R^4$,
(f) phenyl, which is unsubstituted or substituted with 1-4 groups independently selected from $R^4$, or
(g) heterocycle, which is unsubstituted or substituted with 1-4 groups independently selected from $R^4$;
and pharmaceutically acceptable salts thereof.

An embodiment of the invention includes compounds of formula Ia:

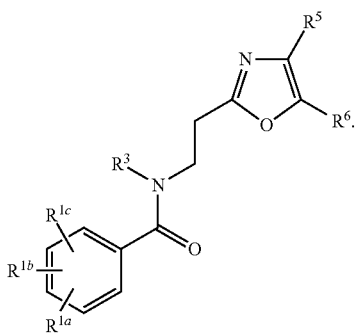

Ia wherein $R^{1a}$, $R^{1b}$, $R^{1c}$, $R^3$, $R^5$ and $R^6$ are as defined herein, or a pharmaceutically acceptable salt thereof.

An embodiment of the invention includes compounds of formula Ib:

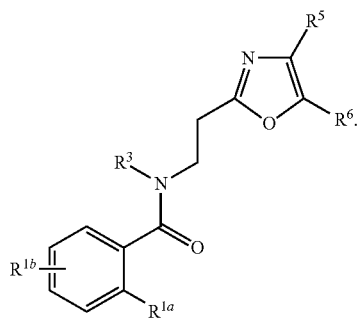

Ib wherein $R^{1a}$, $R^{1b}$, $R^3$, $R^5$ and $R^6$ are as defined herein, or a pharmaceutically acceptable salt thereof.

In an embodiment of each previous embodiment of the invention that includes compounds of Formula I, Ia or Ib, including pharmaceutically acceptable salts thereof, each of $R^{1a}$, $R^{1b}$, and $R^{1c}$, if present, is
(1) hydrogen,
(2) halogen,
(3) C(=O)$OC_{1-3}$alkyl,
(4) $C_{1-3}$alkyl, which is unsubstituted or substituted with 1-5 groups which are independently selected from halogen, hydroxyl and phenyl,
(5) —$OC_{1-3}$alkyl, which is unsubstituted or substituted with 1-5 groups which are independently selected from halogen, hydroxyl and phenyl,
(6) —C(=O)OH,
(7) heteroaryl, wherein heteroaryl is triazolyl, tetrazolyl, oxazolyl, oxadiazolyl, pyrrolyl, pyrazolyl, imidazolyl, indolyl, pyridyl, or pyrimidinyl, and is unsubstituted or substituted with 1-3 groups which are independently selected from halogen, hydroxy, —$C_{1-3}$alkyl, —$OC_{1-3}$alkyl, —CN, and —$NO_2$, wherein —$C_{1-3}$alkyl and —$OC_{1-3}$alkyl are optionally substituted with 1-3 halogens,
(8) phenyl, which is unsubstituted or substituted with 1-3 groups which are independently selected from halogen, hydroxy, —CN, —$CH_3$, —$CF_3$, —$OCH_3$, and —$OCF_3$, or
(9) $C_{3-6}$cycloalkyl, which is unsubstituted or substituted with 1-3 groups which are independently selected from halogen, hydroxyl, $C_{1-3}$alkyl, —$OC_{1-3}$alkyl, and —CN, wherein $C_{1-3}$alkyl, and —$OC_{1-3}$alkyl are optionally substituted with 1-3 halogens.

In an embodiment of each previous embodiment of the invention that includes compounds of Formula I, Ia or Ib, including pharmaceutically acceptable salts thereof, $R^{1a}$ is attached to ring A in any open position on the ring.

In an embodiment of each previous embodiment of the invention that includes compounds of Formula I or Ia, including pharmaceutically acceptable salts thereof, $R^{1a}$ is attached to ring A in a position that is ortho to the carboxamide group connecting A to the rest of the compound.

In an embodiment of each previous embodiment of the invention that includes compounds of Formula I, Ia or Ib, including pharmaceutically acceptable salts thereof, $R^{1a}$ is
(1) heteroaryl which is triazolyl, pyrazolyl, tetrazolyl, or oxadiazolyl, wherein heteroaryl is optionally substituted with 1-3 groups which are independently $C_{1-3}$alkyl optionally substituted with 1-3 halogens, —$OC_{1-3}$alkyl optionally substituted with 1-3 halogens, or halogen, (2) cyclopropyl which is optionally substituted with 1-2 groups which are independently halogen, —CN, —C$_{1-2}$ alkyl, or —OC$_{1-2}$alkyl, wherein —C$_{1-2}$alkyl and —OC$_{1-2}$alkyl are optionally substituted with 1-3 halogens, (3) phenyl which is optionally substituted with 1-3 groups which are independently —CN, —CH$_3$, —OCH$_3$, —CF$_3$, or —OCF$_3$, (4) —C$_{1-3}$alkyl optionally substituted with 1-5 halogens, (5) —OC$_{1-3}$alkyl optionally substituted with 1-5 halogens, (6) —C(=O)OH, or (7) —C(=O)OC$_{1-2}$alkyl.

In embodiments of the invention that include compounds of Formula I, Ia, or Ib, including pharmaceutically acceptable salts thereof, R$^{1b}$ is H, halogen, —C$_{1-3}$alkyl optionally substituted with 1-3 F, or —OC$_{1-3}$alkyl optionally substituted with 1-3 F.

In embodiments of the invention that include compounds of Formula I or Ia, including pharmaceutically acceptable salts thereof, R$^{1c}$ is H.

In embodiments of the invention that include compounds of Formula I, Ia or Ib, including pharmaceutically acceptable salts thereof, R$^3$ is:

(1) C$_{1-3}$alkyl optionally substituted with 1-5 substituent groups, which are independently selected from halogen, —OH, —OCH$_3$, and C$_{3-6}$ cycloalkyl, (2) C$_{2-3}$alkenyl optionally substituted with 1-5 halogens, or (3) C$_{3-5}$ cycloalkyl.

In embodiments of the invention that include compounds of Formula I, Ia or Ib, including pharmaceutically acceptable salts thereof, R$^3$ is:

(1) C$_{1-3}$alkyl optionally substituted with 1-3 F and optionally one group C$_{3-4}$ cycloalkyl, —OH, or —OCH$_3$, (2) C$_{2-3}$alkenyl, or (3) C$_{3-4}$cycloalkyl.

In embodiments of the invention that include compounds of Formula I, Ia or Ib, including pharmaceutically acceptable salts thereof, R$^5$ is C$_{1-6}$alkyl or —OC$_{1-3}$alkyl, wherein R$^5$ is optionally substituted with 1-4 substituent groups which are independently halogen, —OH, or —OCH$_3$.

In embodiments of the invention that include compounds of Formula I, Ia or Ib, including pharmaceutically acceptable salts thereof, R$^5$ is —C(CH$_3$)(OH)C$_{1-3}$alkyl.

In an embodiment of each previous embodiment of the invention that includes compounds of Formula I, Ia or Ib, including pharmaceutically acceptable salts thereof, R$^6$ is C$_{1-3}$alkyl, which is optionally substituted with 1-3 substituent groups which are independently halogen, —OH, or —OCH$_3$.

In an embodiment of each previous embodiment of the invention that includes compounds of Formula I, Ia or Ib, including pharmaceutically acceptable salts thereof, R$^6$ is methyl.

In embodiments of the invention that include compounds of Formula I, Ia, or Ib, including pharmaceutically acceptable salts thereof, R$^{1a}$ is attached to A in a position that is ortho to the carboxamide group that connects A to the rest of the compound, wherein R$^{1a}$ is selected from the group consisting of:

(1) heteroaryl which is triazolyl, pyrazolyl, tetrazolyl, or oxadiazolyl, wherein heteroaryl is optionally substituted with 1-3 groups which are independently C$_{1-3}$alkyl optionally substituted with 1-3 halogens, —OC$_{1-3}$alkyl optionally substituted with 1-3 halogens, or halogen, (2) cyclopropyl which is optionally substituted with 1-2 groups which are independently halogen, —CN, —C$_{1-2}$ alkyl, or —OC$_{1-2}$alkyl, wherein —C$_{1-2}$alkyl and —OC$_{1-2}$alkyl are optionally substituted with 1-3 halogens, (3) phenyl which is optionally substituted with 1-3 groups which are independently —CN, —CH$_3$, —OCH$_3$, —CF$_3$, or —OCF$_3$, (4) —C$_{1-3}$alkyl optionally substituted with 1-5 halogens, (5) —OC$_{1-3}$alkyl optionally substituted with 1-5 halogens, (6) —C(=O)OH, and (7) —C(=O)OC$_{1-2}$alkyl;

R$^{1b}$ is H, halogen, —C$_{1-3}$alkyl optionally substituted with 1-3 F, or —OC$_{1-3}$alkyl optionally substituted with 1-3 F; and R$^{1c}$ is H.

In embodiments of the invention that include compounds of Formula I, Ia, or Ib, including pharmaceutically acceptable salts thereof, R$^{1a}$ is selected from the group consisting of:

(1) heteroaryl which is triazolyl, pyrazolyl, tetrazolyl, or oxadiazolyl, wherein heteroaryl is optionally substituted with 1-3 groups which are independently C$_{1-3}$alkyl optionally substituted with 1-3 halogens, —OC$_{1-3}$alkyl optionally substituted with 1-3 halogens, or halogen, (2) cyclopropyl which is optionally substituted with 1-2 groups which are independently halogen, —CN, —C$_{1-2}$ alkyl, or —OC$_{1-2}$alkyl, wherein —C$_{1-2}$alkyl and —OC$_{1-2}$alkyl are optionally substituted with 1-3 halogens, (3) phenyl which is optionally substituted with 1-3 groups which are independently —CN, —CH$_3$, —OCH$_3$, —CF$_3$, or —OCF$_3$, (4) —C$_{1-3}$alkyl optionally substituted with 1-5 halogens, (5) —OC$_{1-3}$alkyl optionally substituted with 1-5 halogens, (6) —C(=O)OH, and (7) —C(=O)OC$_{1-2}$alkyl, R$^{1b}$ is H, halogen, —C$_{1-3}$alkyl optionally substituted with 1-3 F, or —OC$_{1-3}$alkyl optionally substituted with 1-3 F, and R$^{1c}$ is H.

In embodiments of the invention, including pharmaceutically acceptable salts thereof, A is phenyl or heteroaryl.

In embodiments of the invention, including pharmaceutically acceptable salts thereof, A is phenyl or heteroaryl, wherein heteroaryl is thiazolyl, isothiazolyl, thiophenyl, triazolyl, tetrazolyl, oxazolyl, oxadiazolyl, pyrrolyl, pyrazolyl, thiadiazolyl, imidazolyl, indolyl, pyridyl, or pyrimidinyl.

In embodiments of the invention, including pharmaceutically acceptable salts thereof, A is phenyl, pyridyl, or thiophenyl.

In embodiments of the invention, including pharmaceutically acceptable salts thereof, A is phenyl.

In embodiments of the invention, including pharmaceutically acceptable salts thereof, A is pyridyl.

In embodiments of the invention, including pharmaceutically acceptable salts thereof, A is thiophenyl.

In embodiments of the invention, including pharmaceutically acceptable salts thereof, A is phenyl, and R$^{1c}$ is H.

An embodiment of the present invention includes compounds of Formula Ia, wherein A is phenyl or heteroaryl. An embodiment of the present invention includes compounds of Formula Ia, wherein A is phenyl, pyridyl, thiophenyl, thiazolyl, isothiazolyl, or pyrazolyl. An embodiment of the present invention includes compounds wherein A is thiazolyl. An embodiment of the present invention includes compounds wherein A is isothiazolyl. An embodiment of the present invention includes compounds wherein A is pyrazolyl.

Certain embodiments of the present invention include compounds which are selected from the group consisting of the subject compounds of the Examples herein and pharmaceutically acceptable salts thereof.

Certain embodiments of the present invention include compounds which are selected from the group consisting of the subject compounds of the Examples herein and do not include pharmaceutically acceptable salts of the subject compounds.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Formula I shows the structure of the class of compounds without specific stereochemistry.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl, and hexyl. A group which is designated as being independently substituted with substituents may be independently substituted with multiple numbers of such substituents.

The term "heterocycle" as used herein includes both unsaturated and saturated heterocyclic moieties. When the unsaturated heterocyclic moieties are fully unsaturated, they are aromatic and are referred to herein as "heteroaryl." Examples of unsaturated heterocycles include benzoimidazolyl, benzimidazolonyl, benzofuranyl, benzofurazanyl, benzopyrazolyl, benzothiazolyl, benzotriazolyl, benzothiophenyl, benzoxazepin, benzoxazolyl, carbazolyl, carbolinyl, cinnolinyl, furanyl, imidazolyl, indolinyl, indolyl, dihydroindolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydroquinoxalinyl, tetrazolyl, tetrazolopyridyl, thiadiazolyl, thiazolyl, thienyl, triazolyl, and N-oxides thereof. The saturated heterocyclic moieties include, for example, azetidinyl, 1,4-dioxanyl, oxetanyl, hexahydroazepinyl, piperidinyl, pyrrolidinyl, morpholinyl, tetrahydrofuranyl, thiomorpholinyl, and tetrahydrothienyl, and N-oxides thereof.

The present invention also includes all pharmaceutically acceptable isotopic variations of a compound of the Formula I in which one or more atoms is replaced by atoms having the same atomic number, but an atomic mass or mass number different from the atomic mass or mass number usually found in nature. Examples of isotopes suitable for inclusion in the compounds of the invention include isotopes of hydrogen such as $^2H$ and $^3H$, carbon such as $^{11}C$, $^{13}C$ and $^{14}C$, nitrogen such as $^{13}N$ and $^{15}N$, oxygen such as $^{15}O$, $^{17}O$ and $^{18}O$, phosphorus such as $^{32}P$, sulfur such as $^{35}S$, fluorine such as $^{18}F$, iodine such as $^{123}I$ and $^{125}I$, and chlorine such as $^{36}Cl$. Certain isotopically-labelled compounds of Formula I, for example those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection. Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labelled compounds of Formula I can generally be prepared by conventional techniques known to those skilled in the art or by processes analogous to those described in the accompanying Examples using appropriate isotopically-labelled reagents in place of the non-labelled reagent previously employed.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

Exemplifying the invention are the uses of the compounds, where the uses of the compounds are disclosed herein in the examples and/or in the remainder of the disclosure. Specific compounds of the present invention include specific compounds which are disclosed in the following Examples and pharmaceutically acceptable salts thereof and individual enantiomers or diastereomers thereof.

The present invention is directed to the use of the compounds disclosed herein as antagonists of orexin receptor activity. The subject compounds, and pharmaceutically acceptable salts thereof, are useful in a method of antagonizing orexin receptor activity in a subject, such as a mammal in need of such inhibition, comprising the administration of the compound. In addition to primates, especially humans, a variety of other mammals may be treated by administration of the compound of the present invention. The present invention is directed to a compound of the present invention or a pharmaceutically acceptable salt thereof that could be useful in therapy. The present invention may further be directed to a use of a compound of the present invention or a pharmaceutically acceptable salt thereof for the manufacture of a medicament for antagonizing orexin receptor activity or treating the disorders and diseases noted herein in humans and animals.

The subject being treated according to the present invention by administration of the compound of the invention is generally a mammal, such as a human being, male or female. The amount of the compound administered to the subject is an amount sufficient to antagonize the orexin receptor in the subject. In an embodiment, the amount of compound can be an "effective amount," wherein the subject compound is administered in an amount that will elicit the biological or medical response of a tissue, system, animal, or human that is being sought by the researcher, veterinarian, medical doctor or other clinician. An effective amount does not necessarily include considerations of toxicity or safety related to the administration of the compound. It is recognized that one skilled in the art may affect the neurological and psychiatric disorders associated with orexin receptor activation by treating a patient presently afflicted with the disorders or by prophylactically treating a patient afflicted with the disorders with an effective amount of the compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a patient who is predisposed to such disease or disorder. The terms "administration of" and or "administering a" compound should be understood to mean providing a compound of the invention or a prodrug of a compound of the invention to the individual in need thereof.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as orexin receptor OX1R and/or OX2R antagonists may be readily determined without undue experimentation by methodology well known in the art, including the "FLIPR $Ca^{2+}$ Flux Assay" (Okumura et al., Biochem. Biophys. Res. Comm. 280:976-981, 2001). In a typical experiment the OX1 and OX2 receptor antagonistic activity of the compounds of the present invention was determined in accordance with the following experimental method. For intracellular calcium measurements, Chinese hamster ovary (CHO) cells expressing the rat or human orexin-1 receptor or the human orexin-2 receptor, are grown in Iscove's modified DMEM containing 2 mM L-glutamine, 0.5 g/ml G418, 1% hypoxanthine-thymidine supplement, 100 U/ml penicillin, 100 µg/ml streptomycin and 10% heat-inactivated fetal calf serum (FCS). The cells are seeded at 20,000 cells/well into Becton-Dickinson black 384-well clear bottom sterile plates coated with poly-D-lysine. All reagents were from GIBCO-Invitrogen Corp. The seeded plates are incubated overnight at 37° C. and 5% CO2. Ala-6,12 human orexin-A as the agonist is prepared as a 1 mM stock solution in 1% bovine serum albumin (BSA) and diluted in assay buffer (HBSS containing 20 mM HEPES, 0.1% BSA and 2.5 mM probenecid, pH7.4) for use in the assay at a final concentration of 70 pM. Test compounds are prepared as 10 mM stock solution in DMSO, then diluted in 384-well plates, first in DMSO, then assay buffer. On the day of the assay, cells are washed 3 times with 100 µl assay buffer and then incubated for 60 min (37° C., 5% CO2) in 60 µl assay buffer containing 1 µM Fluo-4AM ester, 0.02% pluronic acid, and 1% BSA. The dye loading solution is then aspirated and cells are washed 3 times with 100 µl assay buffer. 30 µl of that same buffer is left in each well. Within the Fluorescent Imaging Plate Reader (FLIPR, Molecular Devices), test compounds are added to the plate in a volume of 25 µl, incubated for 5 min and finally 25 µl of agonist is added. Fluorescence is measured for each well at 1 second intervals for 5 minutes and the height of each fluorescence peak is compared to the height of the fluorescence peak induced by 70 pM Ala-6,12 orexin-A with buffer in place of antagonist. For each antagonist, IC50 value (the concentration of compound needed to inhibit 50% of the agonist response) is determined. Alternatively, compound potency can be assessed by a radioligand binding assay (described in Bergman et. al. Bioorg. Med. Chem. Lett. 2008, 18, 1425-1430) in which the inhibition constant ($K_i$) is determined in membranes prepared from CHO cells expressing either the OX1 or OX2 receptor. The intrinsic orexin receptor antagonist activity of a compound which may be used in the present invention may be determined by these assays.

All of the final compounds of the following examples had activity in the FLIPR assay with an IC50 of about 12 nM to about 630 nM against the orexin-2 receptor. Additional data is provided in the following Examples. Such a result is indicative of the intrinsic activity of the compounds in use as antagonists of the orexin receptors, particularly the orexin-2 receptor. In general, one of ordinary skill in the art would appreciate that a substance is considered to effectively antagonize the orexin receptor if it has an IC50 of less than about 50 µM, preferably less than about 1000 nM.

The orexin receptors have been implicated in a wide range of biological functions. This has suggested a potential role for these receptors in a variety of disease processes in humans or other species. The compounds of the present invention could therefore potentially have utility in treating, preventing, ameliorating, controlling or reducing the risk of a variety of neurological and psychiatric disorders associated with orexin receptors, including one or more of the following conditions or diseases: sleep disorders, sleep disturbances, including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent wakings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia, hypersomnia, idiopathic hypersomnia, repeatability hypersomnia, intrinsic hypersomnia, narcolepsy, interrupted sleep, sleep apnea, wakefulness, nocturnal myoclonus, REM sleep interruptions, jet-lag, shift workers' sleep disturbances, dyssomnias, night terror, insomnias associated with depression, emotional/mood disorders, Alzheimer's disease or cognitive impairment, as well as sleep walking and enuresis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; fibromyalgia; syndromes which are manifested by non-restorative sleep and muscle pain or sleep apnea which is associated with respiratory disturbances during sleep; conditions which result from a diminished quality of sleep; increasing learning; augmenting memory; increasing retention of memory; eating disorders associated with excessive food intake and complications associated therewith, compulsive eating disorders, obesity (due to any cause, whether genetic or environmental), obesity-related disorders overeating, anorexia, bulimia, cachexia, dysregulated appetite control, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, lung disease, abnormal heart rhythms and arrythmias, myocardial infarction, congestive heart failure, coronary heart disease, acute and congestive heart failure; hypotension; hypertension; urinary retention; osteoporosis; angina pectoris; myocardinal infarction; ischemic or haemorrhagic stroke; subarachnoid haemorrhage; ulcers; allergies; benign prostatic hypertrophy; chronic renal failure; renal disease; impaired glucose tolerance; sudden death, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia, metabolic syndrome, also known as syndrome X, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, intestinal motility dyskinesias, obesity-related gastro-esophageal reflux, hypothalmic diseases, hypophysis diseases, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, hyperuricaemia, lower back pain, gallbladder disease, gout, kidney cancer, increased anesthetic risk, reducing the risk of secondary outcomes of obesity, such as reducing the risk of left ventricular hypertrophy; diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function, including cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders; enhancing memory; increasing memory retention; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; affective neurosis; depressive neurosis; anxiety neurosis; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; Huntington's disease and Tourette syndrome; Cushing's syndrome/disease; basophile adenoma; prolactinoma; hyperprolactinemia; hypophysis tumor/adenoma; hypothalamic diseases; inflammatory bowel disease; gastric diskinesia; gastric ulcers; Froehlich's syndrome; adrenohypophysis disease; hypophysis disease; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions, seizure disorders, absence seisures, complex partial and generalized seizures; Lennox-Gastaut syndrome; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; dissociative disorders including multiple personality syndromes and psychogenic amnesias; substance-related disorders, substance use, substance abuse, substance seeking, substance reinstatement, all types of psychological and physical addictions and addictive behaviors, reward-related behaviors (including substance-induced delirium, persisting dementia, persisting amnestic disorder, psychotic disorder or anxiety disorder; tolerance, addictive feeding, addictive feeding behaviors, binge/purge feeding behaviors, dependence, withdrawal or relapse from substances including alcohol, amphetamines, cannabis, cocaine, hallucinogens, inhalants, morphine, nicotine, opioids, phencyclidine, sedatives, hypnotics or anxiolytics); appetite, taste, eating or drinking disorders; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); neurodegenerative disorders including nosological entities such as disinhibition-dementia-parkinsonism-amyotrophy complex; pallido-ponto-nigral degeneration; epilepsy; seizure disorders; attention deficit/hyperactivity disorder (ADHD); conduct disorder; migraine (including migraine headache); headache; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; gastric dyskinesia; gastric ulcers; Kallman's syndrome (anosmia); asthma; cancer; conditions associated with visceral pain such as irritable bowel syndrome, and angina; eating disorders; urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache and other diseases related to general orexin system dysfunction.

Thus, in certain embodiments the present invention may provide methods for: enhancing the quality of sleep; augmenting sleep maintenance; increasing REM sleep; increasing stage 2 sleep; decreasing fragmentation of sleep patterns; treating insomnia and all types of sleep disorders; treating or controlling sleep disturbances associated with diseases such as neurological disorders including neuropathic pain and restless leg syndrome; treating or controlling addiction disorders; treating or controlling psychoactive substance use and abuse; enhancing cognition; increasing memory retention; treating or controlling obesity; treating or controlling diabetes and appetite, taste, eating, or drinking disorders; treating or controlling hypothalamic diseases; treating or controlling depression; treating, controlling, ameliorating or reducing the risk of epilepsy, including absence epilepsy; treating or controlling pain, including neuropathic pain; treating or controlling Parkinson's disease; treating or controlling psychosis; treating or controlling dysthymic, mood, psychotic and anxiety disorders; treating or controlling depression, including major depression and major depression disorder; treating or controlling bipolar disorder; or treating, controlling, ameliorating or reducing the risk of schizophrenia, in a mammalian patient in need thereof which comprises administering to the patient a therapeutically effective amount of a compound of the present invention.

The subject compounds could further be of potential use in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Generally, dosage levels of between 0.0001 to 10 mg/kg. of body weight daily are administered to the patient, e.g., humans and elderly humans, to obtain effective antagonism of orexin receptors. The dosage range will generally be about 0.5 mg to 1.0 g. per patient per day which may be administered in single or multiple doses. In one embodiment, the dosage range will be about 0.5 mg to 500 mg per patient per day; in another embodiment about 0.5 mg to 200 mg per patient per day; and in yet another embodiment about 5 mg to 50 mg per patient per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 30 mg, 50 mg, 80 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, such as once or twice per day. The compounds may be administered before bedtime. For example, the compounds may be administered about 1 Hour prior to bedtime, about 30 minutes prior to bedtime or immediately before bedtime.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is contemplated. Accordingly, the pharmaceutical compositions of the present invention include those that also contain one or more other active ingredients, in addition to a compound of the present invention.

The weight ratio of the compound of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be administered in combination with other compounds which are known in the art to be useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, ornortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the subject compound may be employed in combination with other compounds which are known in the art, either administered separately or in the same pharmaceutical compositions, including, but are not limited to: insulin sensitizers including (i) PPARγ antagonists such as glitazones (e.g. ciglitazone; darglitazone; englitazone; isaglitazone (MCC-555); pioglitazone; rosiglitazone; troglitazone; tularik; BRL49653; CLX-0921; 5-BTZD), GW-0207, LG-100641, and LY-300512, and the like); (iii) biguanides such as metformin and phenformin; (b) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-NH$_2$); (c) sulfonylureas, such as acetohexamide; chlorpropamide; diabinese; glibenclamide; glipizide; glyburide; glimepiride; gliclazide; glipentide; gliquidone; glisolamide; tolazamide; and tolbutamide; (d) α-glucosidase inhibitors, such as acarbose, adiposine; camiglibose; emiglitate; miglitol; voglibose; pradimicin-Q; salbostatin; CKD-711; MDL-25,637; MDL-73,945; and MOR 14, and the like; (e) cholesterol lowering agents such as (i) HMG-CoA reductase inhibitors (atorvastatin, itavastatin, fluvastatin, lovastatin, pravastatin, rivastatin, rosuvastatin, simvastatin, and other statins), (ii) bile acid absorbers/sequestrants, such as cholestyramine, colestipol, dialkylaminoalkyl derivatives of a cross-linked dextran; Colestid®; LoCholest®, and the like, (ii) nicotinyl alcohol, nicotinic acid or a salt thereof, (iii) proliferator-activater receptor α agonists such as fenofibric acid derivatives (gemfibrozil, clofibrate, fenofibrate and benzafibrate), (iv) inhibitors of cholesterol absorption such as stanol esters, beta-sitosterol, sterol glycosides such as tiqueside; and azetidinones such as ezetimibe, and the like, and (acyl CoA: cholesterol acyltransferase (ACAT)) inhibitors such as avasimibe, and melinamide, (v) anti-oxidants, such as probucol, (vi) vitamin E, and (vii) thyromimetics; (f) PPARα agonists such as beclofibrate, benzafibrate, ciprofibrate, clofibrate, etofibrate, fenofibrate, and gemfibrozil; and other fibric acid derivatives, such as Atromid®, Lopid® and Tricor®, and the like, and PPARα agonists as described in WO 97/36579; (g) PPARδ agonists, such as those disclosed in WO97/28149; (h) PPAR α/δ agonists, such as muraglitazar, and the compounds disclosed in U.S. Pat. No. 6,414,002; (i) anti-obesity agents, such as (1) growth hormone secretagogues, growth hormone secretagogue receptor agonists/antagonists, such as NN703, hexarelin, MK-0677, SM-130686, CP-424,391, L-692,429, and L-163,255, and such as those disclosed in U.S. Pat. Nos. 5,536,716, and 6,358,951, U.S. Patent Application Nos. 2002/049196 and 2002/022637, and PCT Application Nos. WO 01/56592 and WO 02/32888; (2) protein tyrosine phosphatase-1B (PTP-1B) inhibitors; (3) cannabinoid receptor ligands, such as cannabinoid CB$_1$ receptor antagonists or inverse agonists, such as rimonabant, taranabant, AMT-251, and SR-14778 and SR 141716A (Sanofi Synthelabo), SLV-319 (Solvay), BAY 65-2520 (Bayer) and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, WO 01/64632, WO 01/64633, WO 01/64634, WO02/076949, WO 03/007887, WO 04/048317, and WO 05/000809; (4) anti-obesity serotonergic agents, such as fenfluramine, dexfenfluramine, phentermine, and sibutramine; (5) β3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A; (6) pancreatic lipase inhibitors, such as orlistat (Xenical®), Triton WR1339, RHC80267, lipstatin, tetrahydrolipstatin, teasaponin, diethylumbelliferyl phosphate, and those disclosed in PCT Application No. WO 01/77094; (7) neuropeptide Y1 antagonists, such as BIBP3226, J-115814, BIBO 3304, LY-357897, CP-671906, GI-264879A, and those disclosed in U.S. Pat. No. 6,001, 836, and PCT Patent Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,057,335; 6,043,246; 6,140,354; 6,166,038; 6,180,653; 6,191,160; 6,313,298; 6,335,345; 6,337,332; 6,326,375; 6,329,395; 6,340,683; 6,388,077; 6,462,053; 6,649,624; and 6,723,847, European Patent Nos. EP-01010691, and EP-01044970; and PCT International Patent Publication Nos. WO 97/19682, WO 97/20820, WO 97/20821, WO 97/20822, WO 97/20823, WO 98/24768; WO 98/25907; WO 98/25908; WO 98/27063, WO 98/47505; WO 98/40356; WO 99/15516; WO 99/27965; WO 00/64880, WO 00/68197, WO 00/69849, WO 01/09120, WO 01/14376; WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; WO 02/094825; WO 03/014083; WO 03/10191; WO 03/092889; WO 04/002986; and WO 04/031175; (9) melanin-concentrating hormone (MCH) receptor antagonists, such as those disclosed in WO 01/21577 and WO 01/21169; (10) melanin-concentrating hormone 1 receptor (MCH1R) antagonists, such as T-226296 (Takeda), and those disclosed in PCT Patent Application Nos. WO 01/82925, WO 01/87834, WO 02/051809, WO 02/06245, WO 02/076929, WO 02/076947, WO 02/04433, WO 02/51809, WO 02/083134, WO 02/094799, WO 03/004027; (11) melanin-concentrating hormone 2 receptor (MCH2R) agonist/antagonists; (12) orexin receptor antagonists, such as SB-334867-A, and those disclosed in patent publications herein; (13) serotonin reuptake inhibitors such as fluoxetine, paroxetine, and sertraline; (14) melanocortin agonists, such as Melanotan II; (15) Mc4r (melanocortin 4 receptor) agonists, such as CHIR86036

(Chiron), ME-10142, and ME-10145 (Melacure), CHIR86036 (Chiron); PT-141, and PT-14 (Palatin); (16) 5HT-2 agonists; (17) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (18) galanin antagonists; (19) CCK agonists; (20) CCK-A (cholecystokinin-A) agonists, such as AR-R 15849, GI 181771, JMV-180, A-71378, A-71623 and SR14613, and those described in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and O-[3-(1H-imidazol-4-yl)propanol]-carbamates; (25) β-hydroxy steroid dehydrogenase-1 inhibitors (β-HSD-1); (26) PDE (phosphodiesterase) inhibitors, such as theophylline, pentoxifylline, zaprinast, sildenafil, amrinone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists, such as those disclosed in PCT Application Nos. WO 01/87335, and WO 02/08250; (30) leptin, including recombinant human leptin (PEG-OB, Hoffman La Roche) and recombinant methionyl human leptin (Amgen); (31) leptin derivatives; (32) BRS3 (bombesin receptor subtype 3) agonists such as [D-Phe6, beta-Ala11,Phe13,Nle14]Bn(6-14) and [D-Phe6,Phe13]Bn (6-13)propylamide, and those compounds disclosed in Pept. Sci. 2002 August; 8(8): 461-75); (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron); (35) monoamine reuptake inhibitors, such as sibutramine; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl] benzoic acid (TTNPB), retinoic acid; (37) thyroid hormone β agonists, such as KB-2611 (KaroBioBMS); (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoylestrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444, sitagliptin; and the compounds disclosed in U.S. Pat. No. 6,699,871, WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (46) dicarboxylate transporter inhibitors; (47) glucose transporter inhibitors; (48) phosphate transporter inhibitors; (49) Metformin (Glucophage®); (50) Topiramate (Topimax®); (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)); (51) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (52) Neuropeptide Y4 (NPY4) agonists such as pancreatic peptide (PP), and other Y4 agonists such as 1229U91; (54) cyclooxygenase-2 inhibitors such as etoricoxib, celecoxib, valdecoxib, parecoxib, lumiracoxib, BMS347070, tiracoxib or JTE522, ABT963, CS502 and GW406381; (55) Neuropeptide Y1 (NPY1) antagonists such as BIBP3226, J-115814, BIBO 3304, LY-357897, CP-671906, GI-264879A; (56) Opioid antagonists such as nalmefene (Revex®), 3-methoxynaltrexone, naloxone, naltrexone; (57) 11β HSD-1 (11-beta hydroxy steroid dehydrogenase type 1) inhibitors such as BVT 3498, BVT 2733, and those disclosed in WO 01/90091, WO 01/90090, WO 01/90092, U.S. Pat. No. 6,730,690 and US 2004-0133011; (58) aminorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phenmetrazine; (86) picilorex; (87) phytopharm 57; and (88) zonisamide, (89) neuromedin U and analogs or derivatives thereof, (90) oxyntomodulin and analogs or derivatives thereof, and (91) Neurokinin-1 receptor antagonists (NK-1 antagonists) such as the compounds disclosed in: U.S. Pat. Nos. 5,162,339, 5,232,929, 5,242,930, 5,373,003, 5,387, 595, 5,459,270, 5,494,926, 5,496,833, and 5,637,699.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, $5\text{-HT}_{1A}$ agonists or antagonists, especially $5\text{-HT}_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; citalopram, duloxetine, fluoxetine, fluvoxamine, paroxetine and sertraline; isocarboxazid, phenelzine, tranylcypromine and selegiline; moclobemide: venlafaxine, aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the subject compound may be employed in combination with anti-Alzheimer's agents; beta-secretase inhibitors; gamma-secretase inhibitors; growth hormone secretagogues; recombinant growth hormone; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine $H_3$ antagonists; AMPA agonists; PDE IV inhibitors; GABAA inverse agonists; or neuronal nicotinic agonists.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, clonazepam, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, venlafaxine, zaleplon, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole.

In another embodiment, the subject compound may be employed in combination with acetophenazine, alentemol, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene or trifluoperazine.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone.

In another embodiment, the subject compound may be employed in combination with a nicotine agonist or a nicotine receptor partial agonist such as varenicline, opioid antagonists (e.g., naltrexone (including naltrexone depot), antabuse, and nalmefene), dopaminergic agents (e.g., apomorphine), ADD/ADHD agents (e.g., methylphenidate hydrochloride (e.g., Ritalin® and Concerta®), atomoxetine (e.g., Strattera®), a monoamine oxidase inhibitor (MAOI), amphetamines (e.g., Adderall®)) and anti-obesity agents, such as apo-B/MTP inhibitors, 11Beta-hydroxy steroid dehydrogenase-1 (11Beta-HSD type 1) inhibitors, peptide YY3-36 or analogs thereof, MCR-4 agonists, CCK-A agonists, monoamine reuptake inhibitors, sympathomimetic agents, β3 adrenergic receptor agonists, dopamine receptor agonists, melanocyte-stimulating hormone receptor analogs, 5-HT2c receptor agonists, melanin concentrating hormone receptor antagonists, leptin, leptin analogs, leptin receptor agonists, galanin receptor antagonists, lipase inhibitors, bombesin receptor agonists, neuropeptide-Y receptor antagonists (e.g., NPY Y5 receptor antagonists), thyromimetic agents, dehydroepiandrosterone or analogs thereof, glucocorticoid receptor antagonists, other orexin receptor antagonists, glucagon-like peptide-1 receptor agonists, ciliary neurotrophic factors, human agouti-related protein antagonists, ghrelin receptor antagonists, histamine 3 receptor antagonists or inverse agonists, and neuromedin U receptor agonists, and pharmaceutically acceptble salts thereof.

In another embodiment, the subject compound may be employed in combination with an anoretic agent such as aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; selective serotonin reuptake inhibitor (SSRI); halogenated amphetamine derivatives, including chlorphentermine, cloforex, clortermine, dexfenfluramine, fenfluramine, picilorex and sibutramine; and pharmaceutically acceptble salts thereof.

In another embodiment, the subject compound may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a nonsteroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention may be effective for use in humans.

The compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art (e.g. PCT Patent Publications WO2001/68609, WO2004/085403, WO2005/118548, WO2008/147518, WO2009/143033 and WO2010/048012) or as illustrated herein. The following abbreviations are used herein: Me: methyl; Et: ethyl; t-Bu: tert-butyl; Ar: aryl; Ph: phenyl; Bn: benzyl; Ac: acetyl; Boc: tert-butyloxy carbonyl; BSA: bovine serum albumin; CbzCl: benzylchloroformate; CDI: carbonyl diimidazole; Celite®: a trade name for diatomaceous earth that is used as a filter aid; DCM: dichloromethane; DCE: dichloroethane; DEAD: diethylazodicarboxylate; DIPEA: N,N-diisopropylethylamine; DMF: N,N-dimethylformamide; DMSO: dimethylsulfoxide; dppf: 1,1'-bis(diphenylphosphino)ferrocene; EDC: N-(3-Dimethylaminopropyl)-N'-ethylcarbodiimide; EtMgBr: ethylmagnesium bromide; Et$_3$N: triethylamine; EtI: iodoethane; Et$_2$O: diethyl ether; EtOAc: ethyl acetate; EtOH: ethanol; HCl: hydrogen chloride; HATU: (O-(7-azabenzotriazol-1-yl)-N,N,N',N'-tetramethyluronium hexafluorophosphate); HOAt: 1-hydroxy-7-aza-benzotriazole; HOBT: hydroxybenzotriazole hydrate; HPLC: high performance liquid chromatography; Hunig's base: N,N-diisopropylethylamine; LRMS: low resolution mass spectrometry; MeMgBr: methylmagnesium bromide; MeMgCl: methylmagnesium chloride; MeOH: methanol; MgSO$_4$: magnesium sulfate; MTBE: methyl tert-butyl ether; NaHCO$_3$: sodium bicarbonate; NaOH: sodium hydroxide; NMM: N-methylmorpholine; PPh$_3$: triphenyl phosphine; iPrMgCl: isopropyl magnesium chloride; rt or RT: room temperature; SOCl$_2$: thionyl chloride; T3P: 2,4,6-tripropyl-1,3,5,2,4,6-trioxatriphosphorinane-2,4,6-trioxide; TBAF: tetrabutylammonium fluoride; TBSCl: tert-butyldimethylsilyl chloride; TBSO: tert-butyldimethylsilyl ether; TEA: triethylamine; THF: tetrahydrofuran; TFA: trifluoracetic acid; TMSCHN$_2$: trimethylsilyldiazomethane.

The compounds of the present invention can be prepared in a variety of fashions. In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

While the invention is described and illustrated with reference to certain particular embodiments thereof, those skilled in the art will appreciate that various adaptations, changes, modifications, substitutions, deletions, or additions of procedures and protocols may be made without departing from the spirit and scope of the invention.

Intermediates

Intermediate A 2-(1-Cyanocyclopropyl)benzoic Acid

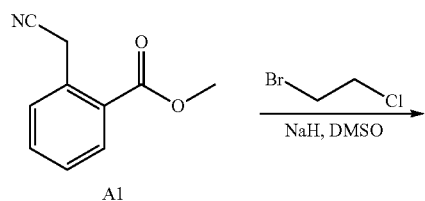

A1

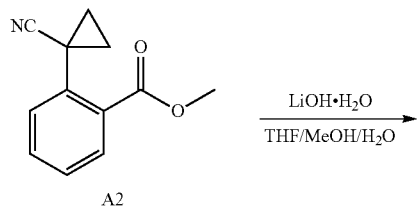

A2

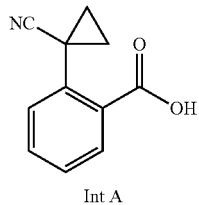

Int A

Step 1: Methyl 2-(1-cyanocyclopropyl)benzoate (A2)

To a solution of NaH (1.10 g, 26.2 mmol) in DMSO (20 mL) was added compound A1 (2.00 g, 11.4 mmol); after stirring at RT under nitrogen for 1 h, 1-bromo-2-chloroethane (1.8 g, 12.6 mmol) was added and the mixture was stirred at RT for 2 h. The mixture was quenched with ice water (10 mL) and extracted with EtOAc (10 mL×3). The organic layers were combined, dried, and concentrated in vacuo to give the crude compound, which was purified by silica gel column chromatography (petroleum ether/EtOAc 20:1) to give the title compound as a solid. MS (ESI) m/e (M+H+) was detected.

Step 2: 2-(1-Cyanocyclopropyl)benzoic Acid

A solution of compound A2 in THF/MeOH/H$_2$O (3:1:1, 16 mL) was treated with lithium hydroxide in water (3 mL). The mixture was stirred overnight at RT. The THF and MeOH were removed in vacuo and the resulting solution acidified to pH ~1 with 1 N HCl to give a crystalline precipitate. The crystals were isolated by filtration, washed with water, and dried in vacuo affording intermediate A as a solid. MS (ESI) m/e (M+H$^+$): 187.9.

Intermediate B 2-(1-Cyanocyclobutyl)benzoic Acid

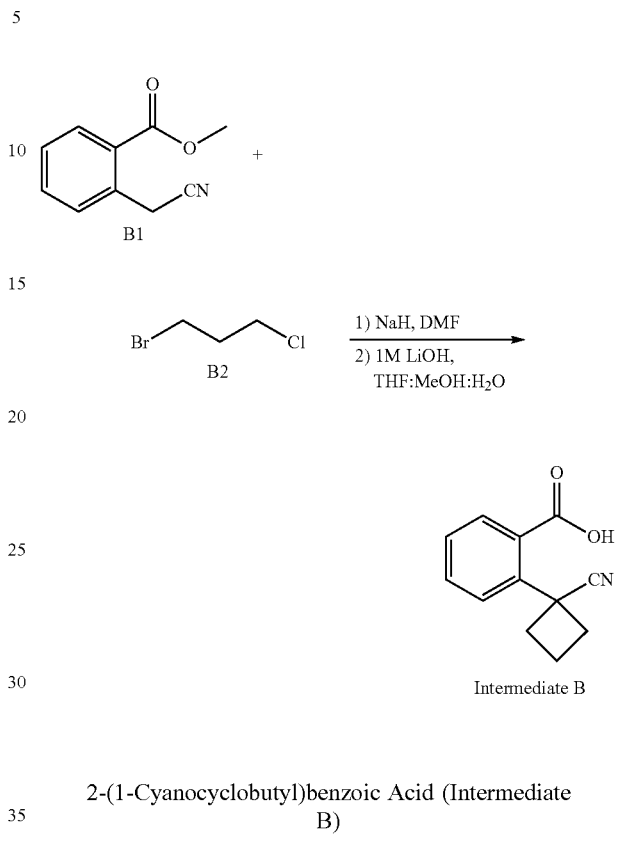

2-(1-Cyanocyclobutyl)benzoic Acid (Intermediate B)

A solution of methyl 2-(cyanomethyl)benzoate (1.07 g, 6.11 mmol) in DMSO (10 mL) was treated with NaH (60 wt % in mineral oil, 0.537 g, 13.44 mmol) at RT. The mixture was stirred for 30 mins, then 1-bromo-3-chloropropane (1.06 g, 6.72 mmol) was added and the reaction mixture was stirred at RT until the reaction was complete. Et$_2$O (10 mL) was added, the mixture was cooled to 0° C., quenched with water, and extracted with Et$_2$O (75 mL×2). The combined organic fractions were washed with brine (40 mL), dried over Na$_2$SO$_4$, filtered, and concentrated in vacuo. The crude material was purified by silica gel column chromatography (0-20% EtOAc in hexanes), providing methyl 2-(1-cyanocyclobutyl)benzoate as an oil.

Methyl 2-(1-cyanocyclobutyl)-benzoate (210 mg, 0.976 mmol) was dissolved in THF (2 mL), MeOH (0.7 mL), and H$_2$O (0.7 mL) and treated with aqueous 2 M LiOH (1.0 mL). The mixture was stirred at RT overnight. Additional 2 M LiOH (0.5 mL) and MeOH (0.5 mL) were added and stirring was continued for 8 h, followed by a further addition of 2 M LiOH (0.5 mL) and stirring for 16 h. The reaction was concentrated in vacuo, and the pH of the resulting aqueous solution was adjusted to ~6 with 1 N HCl. The solution was extracted with EtOAc (75 mL×3). The combined organic fractions were washed with brine, dried over Na$_2$SO$_4$, filtered, and concentrated in vacuo to give the title compound which was used without further purification. LRMS m/z (M+H) 202.1 found, 202.2 required.

Intermediate C

2-(2H-Tetrazol-2-yl)benzoic Acid

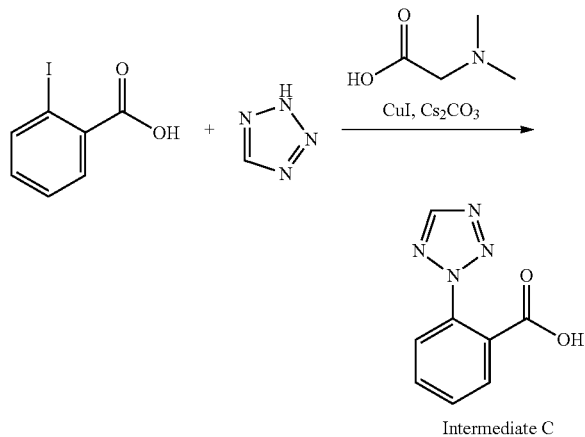

Intermediate C

A mixture of 2-iodobenzoic acid (1.85 g, 7.46 mmol), cesium carbonate (4.06 g, 12.5 mmol), and copper(I) iodide (0.128 g, 0.671 mmol) in DMA (8.0 mL) was treated with N,N'-dimethylglycine (0.131 g, 1.27 mmol) and tetrazole (1.29 g, 18.4 mmol). The reaction was irradiated at 100° C. for 1 h. The reaction was diluted with water and 1 N aqueous NaOH and washed with EtOAc. The aqueous fraction was acidified with concentrated HCl and extracted 2× with EtOAc. The combined organic fractions were washed with brine, dried over MgSO$_4$, filtered, and concentrated in vacuo. The residue was purified by silica gel column chromatography [0-85% (1% acetic acid in EtOAc) in hexanes], providing the title compound. $^1$H NMR (400 MHz, CD$_3$OD): δ7.72-7.84 (m, 3H), 8.07 (dd, J=7.6, 1.6 Hz, 1H), 8.90 (s, 1H) ppm. LRMS m/z (M+H) 191.1 found, 191.2.

Intermediate D

2-(2H)-1,2,3-Triazol-2-yl)thiophene-3-carboxylic Acid

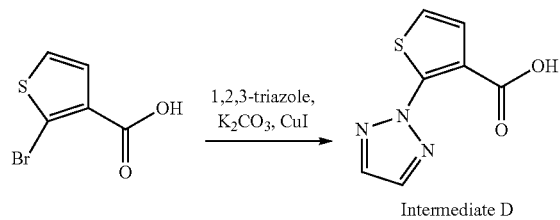 [SMILES: O=C(O)c1ccsc1Br ; O=C(O)c1ccsc1-n1nccn1]

Intermediate D

A solution of 2-bromo-3-thiophene carboxylic acid (1.50 g, 7.24 mmol), 1H-1,2,3-triazole (0.600 g, 8.69 mmol), potassium carbonate (2.00 g, 14.5 mmol), and copper(I) iodide (0.138 g, 0.724 mmol) in DMF (36.2 mL) was purged subsurface with nitrogen and heated at 75° C. for 96 h. The reaction was diluted with water, washed with ether, and acidified with concentrated HCl. The acidic aqueous solution was extracted 3× with EtOAc and the combined organic fractions were washed with brine, dried over MgSO$_4$, filtered, and concentrated in vacuo. The crude material was purified by silica gel column chromatography [0-70% (1% acetic acid in EtOAc) in hexanes], providing the title compound as a solid. LRMS m/z (M+H) 196.2 found, 196.1 required.

Intermediate E

Potassium 2-(pyrimidin-2-yl)thiophene-3-carboxylate

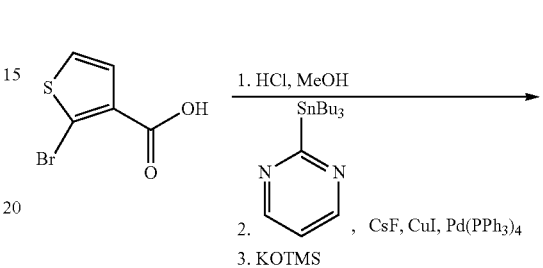

Intermediate E

A solution of 2-bromo-3-thiophene carboxylic acid (3.35 g, 16.2 mmol) in methanol (50 mL) was cooled to 0° C. and saturated with gaseous HCl. The solution was heated at 60° C. overnight, then concentrated in vacuo. The residue was redissolved in EtOAc, washed with saturated aqueous NaHCO$_3$ and brine, dried over Na$_2$SO$_4$, filtered, and concentrated in vacuo, providing methyl 2-bromothiophene-3-carboxylate as an oil. LRMS m/z (M+H) 221.1 found, 221.0 required.

A solution of methyl 2-bromothiophene-3-carboxylate (1.74 g, 7.87 mmol), 2-(tributylstannyl)pyrimidine (4.36 g, 11.81 mmol), cesium fluoride (4.78 g, 31.5 mmol), and copper(I) iodide (0.450 g, 2.36 mmol) in DMF (16 mL) was purged subsurface with nitrogen and treated with tetrakis(triphenylphosphine)palladium(0) (0.455 g, 0.394 mmol). The mixture was sealed and heated at 120° C. overnight. The reaction was partitioned between EtOAc and water and filtered through Celite®. The organic layer was washed with saturated aqueous NaHCO$_3$ and brine, dried over MgSO$_4$, filtered, and concentrated in vacuo. The residue was purified by silica gel column chromatography (0-30% EtOAc in hexanes), providing methyl 2-(pyrimidin-2-yl)thiophene-3-carboxylate as a solid. LRMS m/z (M+H) 221.2 found, 221.1 required.

A solution of methyl 2-(pyrimidin-2-yl)thiophene-3-carboxylate (0.695 g, 3.16 mmol) and potassium trimethylsilanolate (0.506 g, 3.94 mmol) in THF (16 mL) was stirred at RT overnight, then diluted with ether and filtered through a glass frit. The solids were washed with ether, and the filtrate was concentrated in vacuo, providing the title compound as a solid. LRMS m/z (M+H) 207.3 found, 207.1 required.

Intermediate F

4-[1,2,3]Triazol-2-yl-thiophene-3-carboxylic Acid

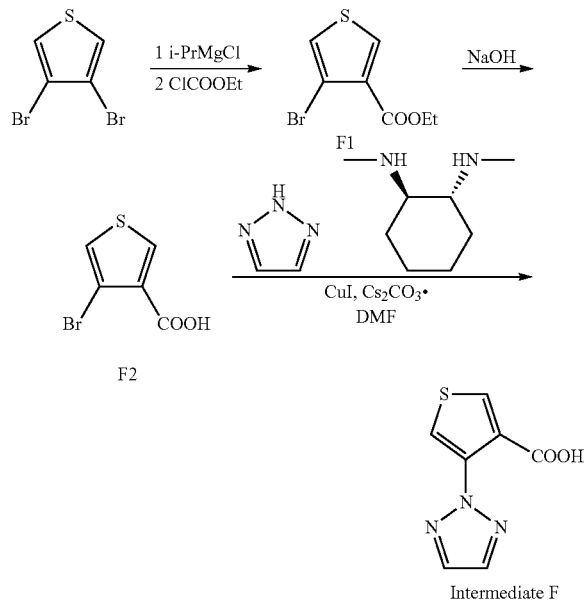

Intermediate F

Step 1: 4-Bromo-thiophene-3-carboxylic Acid Ethyl Ester (F1)

To a solution of 3,4-dibromothiophene (30 g, 0.12 mol) in THF (200 mL) at 0° C. was added i-PrMgCl (2.0 M in THF, 77 mL, 0.15 mol), keeping the temperature below 5° C. The resulting mixture was stirred at 0-5° C. for 5 h, then ethyl chloroformate (14.4 mL, 0.15 mol) was added dropwise at <10° C. The resulting mixture was warmed to RT, stirred overnight, and quenched with saturated, aqueous $NH_4Cl$. Most of the THF was then removed in vacuo, water was added, and the mixture was extracted with EtOAc (80 mL×4). The combined organic layers were dried over $Na_2SO_4$, filtered, and concentrated in vacuo. The crude product was purified by silica gel column chromatography (petroleum ether:EtOAc=300:1) to provide the title compound as an oil.

Step 2: 4-Bromo-thiophene-3-carboxylic Acid (F2)

To a solution of the product from Step 1 (10 g, 43 mmol) in methanol (60 mL) was added NaOH (3.4 g, 86 mmol) and water (1 mL), and the mixture was stirred at RT overnight. The mixture was concentrated in vacuo and the residue was diluted with water (30 mL) and extracted with EtOAc (25 mL×4). The pH of the aqueous layer was adjusted to ~3 with 1 N HCl and the aqueous phase was extracted with EtOAc (25 mL×4). The combined extracts were dried over $Na_2SO_4$, filtered, and concentrated in vacuo to provide the title compound as a solid. LRMS m/z (M+H) 206.9, 208.9 found, 206.9, 208.9 required.

Step 3: 4-[1,2,3]Triazol-2-yl-thiophene-3-carboxylic Acid (Intermediate F)

To a mixture of the product from Step 2 (7.9 g, 38 mmol), $Cs_2CO_3$ (24.8 g, 76 mmol), and copper(I) iodide (2.88 g, 7.6 mmol) in DMF (200 mL) were added 2H-[1,2,3]triazole (5.24 g, 76 mmol) and N,N'-dimethyl-cyclohexane-1,2-diamine (0.9 g, 6.5 mmol), and the mixture was stirred at 110° C. overnight. The cooled mixture was adjusted to ~pH 12 with 1 N NaOH and extracted with EtOAc (50 mL×3). The aqueous layer was adjusted to ~pH 4 with 1 N HCl and extracted with EtOAc (50 mL×4). The extracts were dried over $Na_2SO_4$, filtered, and concentrated in vacuo. The residue was purified by silica gel column chromatography (petroleum ether:EtOAc=10:1) to provide the title compound. LRMS m/z (M+H) 196.0 found, 196.0 required.

Intermediate G

4-Fluoro-2-(2H-1,2,3-triazol-2-yl)benzoic Acid

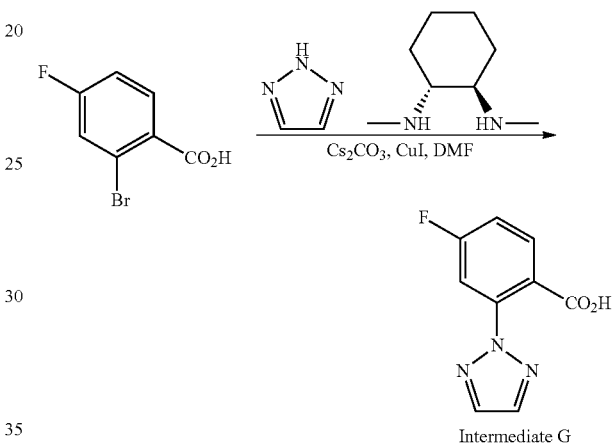

Intermediate G

To a mixture of 2-bromo-4-fluorobenzoic acid (30 g, 137 mmol), cesium carbonate (89.26 g, 274 mmol), and copper (I) iodide (5.27 g, 27.4 mmol) in DMF (200 mL) were added N,N'-dimethylcyclohexane-1,2-diamine (3.7 mL, 23.3 mmol) and 1H-1,2,3-triazole (18.92 g, 274 mmol). The resulting mixture was stirred at 110° C. overnight, cooled, concentrated in vacuo, and diluted with water (150 mL). The aqueous layer was extracted with EtOAc (300 mL×3). The aqueous layer was acidified with 2 N HCl and extracted with EtOAc (300 mL×4). The combined organic layers were washed with brine (150 mL×3), dried over $Na_2SO_4$, filtered, and concentrated in vacuo. The residue was purified by silica gel column chromatography (petroleum ether:EtOAc=100:1~5:1) to provide the title compound as a solid. LRMS m/z (M+H) 208.0 found, 208.0 required.

Intermediates H, I, J

3-Fluoro-2-(2H-1,2,3-triazol-2-yl)benzoic Acid

5-Fluoro-2-(2H-1,2,3-triazol-2-yl)benzoic Acid

6-Fluoro-2-(2H-1,2,3-triazol-2-yl)benzoic Acid

Intermediates H, I, and J were prepared in a similar manner to that described for Intermediate G, replacing 2-bromo-4-fluorobenzoic acid with the appropriate bromo or iodo substituted fluorobenzoic acids.

Intermediate H

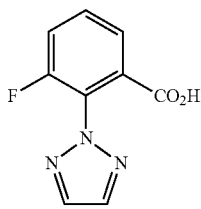

Intermediate I

Intermediate J

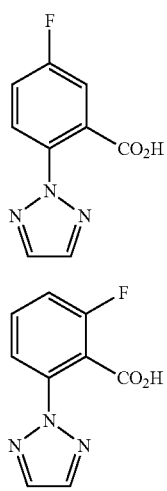

Intermediate K 3-(2H-1,2,3-triazol-2-yl)picolinic Acid

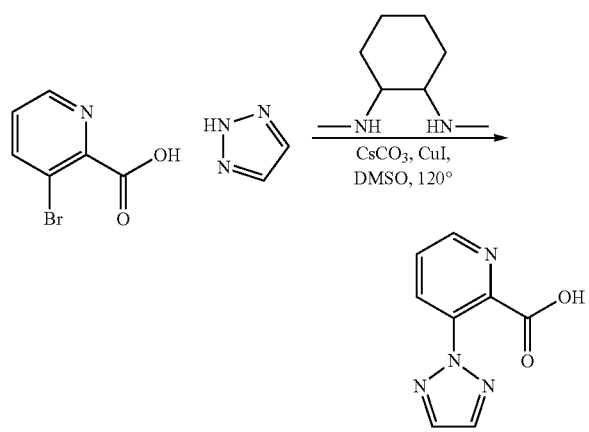

Step 1: 3-(2H-1,2,3-triazol-2-yl)picolinic Acid

To a solution of 3-bromonicotinic acid (1.4 g, 6.93 mmol) in DMSO (14 mL) was added 2H-1,2,3-triazole (0.718 g, 10.40 mmol), cesium carbonate (4.74 g, 14.55 mmol), copper(I) iodide (0.132 g, 0.693 mmol), and N1,N2-dimethylcyclohexane-1,2-diamine (0.099 g, 0.693 mmol). The reaction mixture was sparged with nitrogen and stirred at 120° C. overnight. The cooled reaction mixture was diluted with 1 N NaOH (15 mL) and washed with EtOAc (15 mL). The aqueous layer was acidified with 12 N HCl and extracted with EtOAc (4×20 mL). The combined organic layers were washed with brine, dried over NaSO$_4$, filtered, and concentrated in vacuo. The crude product was purified by silica gel column chromatography (0-100% (EtOAc: 5% AcOH in EtOAc). The purified fractions were combined and azeotroped with toluene (3×100 mL) to give the title compound as a solid. LRMS m/z (M+H) 191.05 found, 191.05 required.

Intermediate L 2-(4-Methyl-1H-pyrazol-1-yl)nicotinic Acid

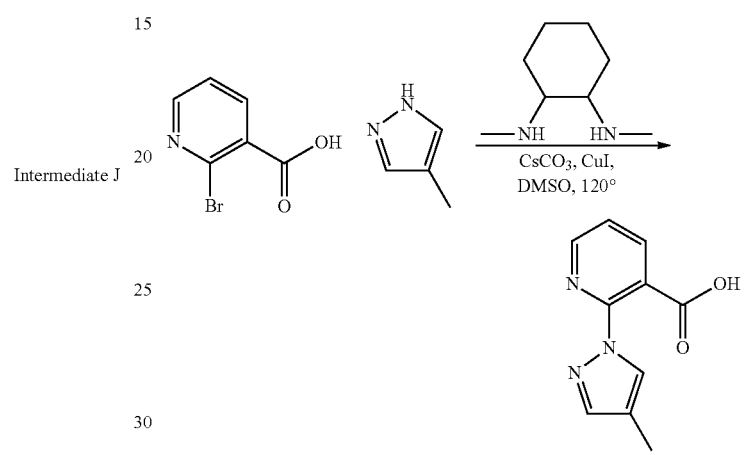

Step 1: 2-(4-Methyl-1H-pyrazol-1-yl)nicotinic Acid

To a solution of 2-bromonicotinic acid (1.4 g, 6.93 mmol) in DMSO (14 mL) was added 4-methyl-1H-pyrazole (0.852 g, 10.40 mmol), cesium carbonate (4.74 g, 14.55 mmol), copper(I) iodide (0.132 g, 0.693 mmol), and N1,N2-dimethylcyclohexane-1,2-diamine (0.099 g, 0.693 mmol). The reaction was sparged with nitrogen and heated at 120° C. overnight. The cooled reaction mixture was diluted with 1 N NaOH (15 mL) and washed with EtOAc (15 mL). The aqueous layer was acidified with 12 N HCl and extracted with EtOAc (4×20 mL). The combined organic layers were washed with brine, dried over NaSO$_4$, filtered, and concentrated in vacuo. The crude material was purified by silica gel column chromatography [0-100% (5% AcOH in EtOAc)/hexanes]. The purified fractions were combined and azeotroped with toluene (3×100 mL) to give the title compound as a solid. LRMS m/z (M+H) 204.07 found, 204.07 required.

Intermediate M 2-(1H-Pyrazol-1-yl)nicotinic Acid

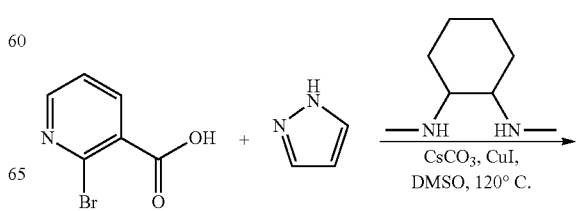

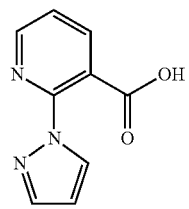

Step 1: 2-(1H-Pyrazol-1-yl)nicotinic Acid

To a solution of 2-bromonicotinic acid (1.4 g, 6.93 mmol) in DMSO (14 mL) was added 1H-pyrazole (0.707 g, 10.40 mmol), cesium carbonate (4.74 g, 14.55 mmol), copper(I) iodide (0.132 g, 0.693 mmol), and N1,N2-dimethylcyclohexane-1,2-diamine (0.099 g, 0.693 mmol). The mixture was sparged with nitrogen and heated at 120° C. overnight. The cooled reaction mixture was diluted with 1 N NaOH (15 mL) and washed with EtOAc (15 mL). The aqueous layer was acidified with 12 N HCl and extracted with EtOAc (4×20 mL). The combined organic layers were washed with brine, dried over NaSO₄, filtered, and concentrated in vacuo. The crude material was purified by silica gel column chromatography [0-100% (5% AcOH in EtOAc)/hexanes]. The purified fractions were combined and azeotroped with toluene (3×100 mL) to give the title compound as a solid. LRMS m/z (M+H) found as required.

Intermediate P 3-(1H-Pyrazol-1-yl)pyrazine-2-carboxylic Acid

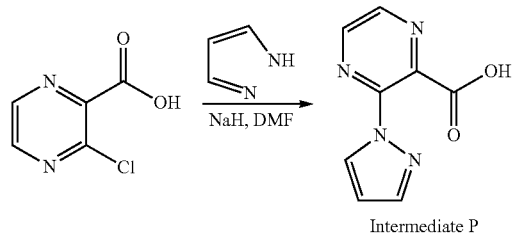

Step 1: 3-(1H-Pyrazol-1-yl)pyrazine-2-carboxylic Acid (Intermediate P)

To a suspension of sodium hydride (60 wt % in mineral oil, 278 mg, 6.95 mmol) in DMF (10 mL) was added 1H-pyrazole (279 mg, 4.11 mmol) at RT and the resulting mixture was stirred at RT for 30 mins. 3-Chloropyrazine-2-carboxylic acid (500 mg, 3.16 mmol) was added and the mixture was heated at 60° C. for 2 h. After cooling to RT, water (20 mL) was added and the mixture was extracted with 5% MeOH in DCM (20 mL×3). The combined organic layers were washed with brine, dried over Na₂SO₄, filtered, and concentrated in vacuo to give the title compound as a solid. LRMS m/z (M+H) 191.0 found, 191.0 required.

Intermediate Q 3-(Pyridin-2-yl)pyrazine-2-carboxylic Acid

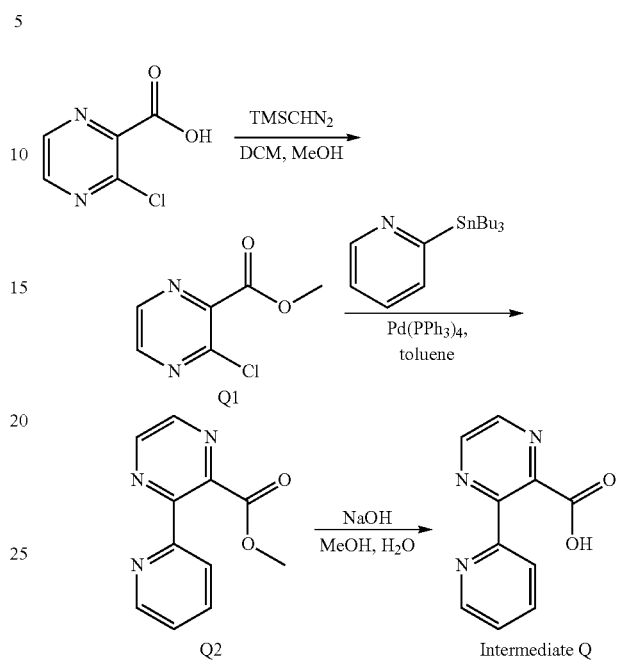

Step 1: Methyl 3-chloropyrazine-2-carboxylate (Q1)

To a solution of 3-chloropyrazine-2-carboxylic acid (100 mg, 0.63 mmol) in DCM/MeOH (2 mL: 0.2 mL) was added TMSCHN₂ (0.47 mL, 0.95 mmol) at RT and the resulting mixture was stirred at RT for 2 h. Acetic acid (0.2 mL) was added and the mixture was diluted with water (2 mL) and extracted with DCM (4 mL×3). The combined organic layers were washed with brine, dried over Na₂SO₄, filtered, and concentrated in vacuo to give the title compound as a colorless oil. LRMS m/z (M+H) 173.0 found, 173.0 required.

Step 2: Methyl 3-(pyridin-2-yl)pyrazine-2-carboxylate (Q2)

To a solution of the product from Step 1 (100 mg, 0.58 mmol) in toluene (2 mL) was added Pd(PPh₃)₄ (134 mg, 0.12 mmol) and 2-(tributylstannyl)pyridine (213 mg, 0.58 mmol). The resulting mixture was heated at 100° C. overnight. After cooling to RT, the mixture was filtered and 5 mL of aqueous KF solution was added to the filtrate. The resulting mixture was stirred for 30 mins and extracted with EtOAc (5 mL×3). The combined organic layers were washed with brine, dried over Na₂SO₄, filtered, and concentrated in vacuo. The residue was purified by chromatography (30% EtOAc in petroleum ether) to provide the title compound as an oil. LRMS m/z (M+H) 216.1 found, 216.1 required.

Step 3: 3-(Pyridin-2-yl)pyrazine-2-carboxylic Acid (Intermediate Q)

A solution of the product from Step 2 (50 mg, 0.23 mmol) and NaOH (27.8 mg, 0.69 mmol) in 2 mL of methanol and 0.1 mL of water was stirred at RT overnight. After adjusting to pH=5 with 1 N HCl, the mixture was concentrated in vacuo. The residue was dissolved in EtOAc (8 mL), stirred for 10 mins, and filtered. The filtrate was concentrated in vacuo to give the title compound as a solid. LRMS m/z (M+H) 202.1 found, 202.1 required.

Intermediate R 2-(3-Methyl-1,2,4-oxadiazol-5-yl)benzoic Acid

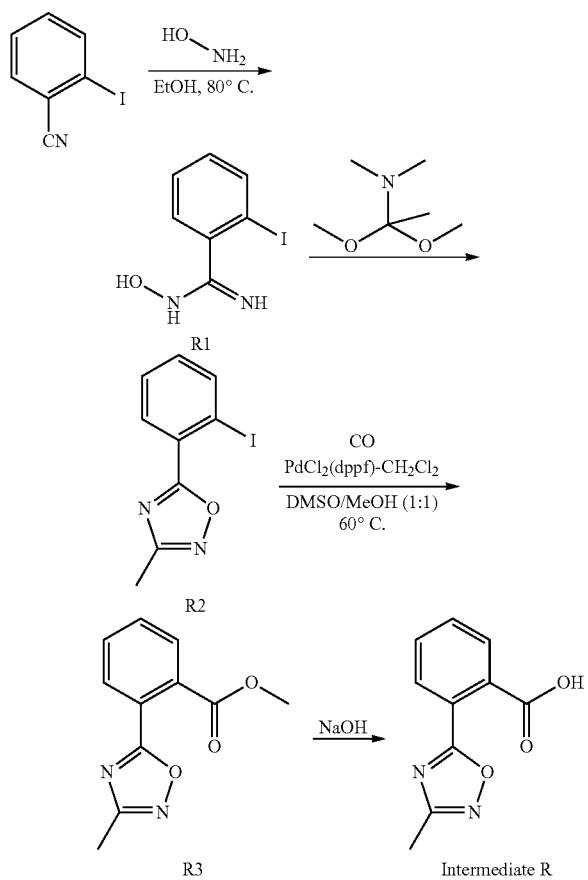

Step 1: N-Hydroxy-2-iodobenzimidamide (R1)

To a solution of 2-iodobenzonitrile (15 g, 65.5 mmol) in EtOH (262 mL) was added hydroxylamine (12.98 g, 196 mmol) and the mixture was heated at 80° C. overnight, cooled, and concentrated in vacuo. The crude mixture was diluted with EtOAc (300 mL) and washed with water (300 mL) and brine (300 mL). The organic layer was dried over NaSO₄, filtered, and concentrated in vacuo to give the product, which was used without further purification. LRMS m/z (M+H) 263.0 found, 263.0 required.

Step 2: 5-(2-Iodophenyl)-3-methyl-1,2,4-oxadiazole (R2)

To 1,1-dimethoxy-N,N-dimethylethanamine (26.4 g, 198 mmol) was added the product from Step 1 (26 g, 99 mmol), and the mixture was stirred at RT for 1 h. The mixture was diluted with EtOAc (30 mL) and washed with water (30 mL) and brine (30 mL). The organic layer was dried over NaSO₄, filtered, and concentrated in vacuo. The crude material was purified by silica gel column chromatography (0-20% EtOAc in hexanes), providing the title compound as an oil.

Step 3: Methyl 2-(3-methyl-1,2,4-oxadiazol-5-yl)benzoate (R3)

A solution of the product from Step 2 (19 g, 66.4 mmol) in MeOH (133 mL) and DMSO (133 mL) was treated with triethylamine (23.1 mL, 166 mmol) and the mixture was sparged with nitrogen. PdCl₂(dppf)-CH₂Cl₂ (2.71 g, 3.32 mmol) was added, the mixture was evacuated and placed under an atmosphere of carbon monoxide, and was stirred overnight at 60° C. The cooled reaction mixture was concentrated in vacuo and diluted with EtOAc (150 mL) and saturated aqueous NaHCO₃. The mixture was filtered over a pad of Celite®. The filtrate was extracted with EtOAc (3×100 mL). The combined organic layers were washed with brine (200 mL), dried over NaSO₄, and concentrated in vacuo. The crude material was purified by silica gel column chromatography (0-60% EtOAc in hexanes), providing the title compound as an oil. LRMS m/z (M+H) 219.1 found, 219.1 required.

Step 4: 2-(3-Methyl-1,2,4-oxadiazol-5-yl)benzoic Acid (Intermediate R)

To a solution of the product from Step 3 (10.2 g, 46.8 mmol) in MeOH (187 mL) was added 1 M NaOH (140 mL, 140 mmol), and the mixture was stirred at 50° C. overnight. The solution was acidified with 12 N HCl to pH ~3 and concentrated in vacuo to remove MeOH. The mixture was redissolved in EtOAc (200 mL) and washed with water (100 mL) and brine (100 mL). The organic layer was dried over NaSO₄, filtered, and concentrated in vacuo to provide the title compound as a solid. LRMS m/z (M+H) 205.1 found, 205.1 required.

Intermediate S

2-Propylnicotinic Acid

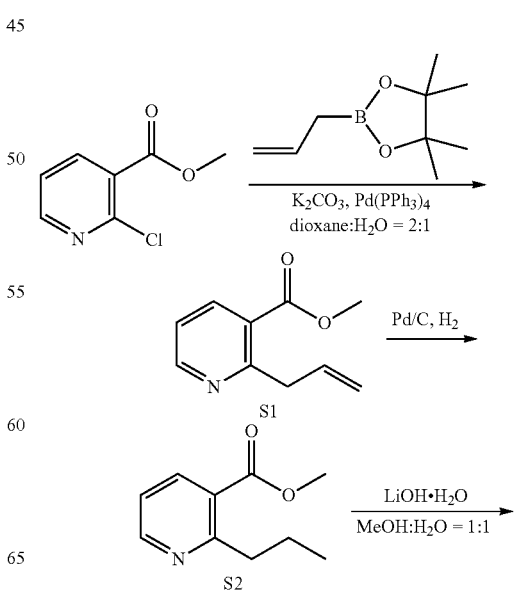

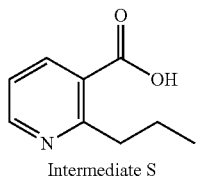

Intermediate S

Step 1: Methyl 2-allylnicotinate (S1)

To a solution of methyl 2-chloronicotinate (300 mg, 1.75 mmol) in dioxane/H$_2$O (2 mL/1 mL) was added 2-allyl-4,5-dimethyl-1,3,2-dioxaborolane (354 mg, 2.11 mmol), K$_2$CO$_3$ (605 mg, 4.39 mmol) and Pd(PPh$_3$)$_4$ (203 mg, 0.175 mmol). The resulting mixture was stirred at 100° C. for 3 hours. After cooling to RT, the mixture was diluted with water (10 mL) and extracted with EtOAc (20 mL×3). The combined organic layers were washed with brine, dried over Na$_2$SO$_4$, filtered, and concentrated in vacuo. The residue was purified by preparative TLC (9% EtOAc in petroleum ether) to give the title compound as an oil. LRMS m/z (M+H) 178.2 found, 178.1 required.

Step 2: Methyl 2-propylnicotinate (S2)

To a solution of the product from Step 1 (4.8 g, 27.1 mmol) in EtOAc (200 mL) was added Pd/C (10 wt %, 500 mg). The resulting mixture was stirred under an atmosphere of H$_2$ at RT overnight. The mixture was filtered and the filtrate was concentrated in vacuo to give the title compound as an oil which was used directly without further purification. LRMS m/z (M+H) 180.2 found, 180.1 required.

Step 3: 2-Propylnicotinic Acid (Intermediate S)

To a solution of the product from Step 2 (4.7 g, 26.3 mmol) in MeOH/H$_2$O (40 mL/40 mL) was added LiOH monohydrate (1.65 g, 39.4 mmol). The resulting mixture was stirred at RT overnight. The mixture was diluted with water (50 mL) and extracted with EtOAc (70 mL×4). The aqueous layer was acidified with 2 N HCl to pH=2 and extracted with EtOAc (200 mL×7). The combined organic layers were dried over Na$_2$SO$_4$, filtered, and concentrated in vacuo. The residue was purified by chromatography (50% EtOAc in petroleum ether) to provide the title compound as a solid. LRMS m/z (M+H) 166.1 found, 166.1 required.

Intermediate T 2-(2,2-Difluoroethoxy)nicotinic Acid

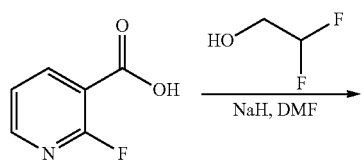

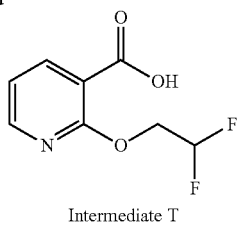

Intermediate T

To a suspension of 2,2-difluoroethanol (492 mg, 6.0 mmol) in DMF (10 mL) at 0° C. was added NaH (180 mg, 4.5 mmol), and the mixture was stirred at 0° C. for 0.5 h. A suspension of 2-fluoronicotinic acid (423 mg, 3.0 mmol) and NaH (180 mg, 4.5 mmol) in DMF (5 mL) was added dropwise at 0° C. and the resulting mixture was stirred at RT overnight. The mixture was diluted with water, acidified to pH~3 with 1 N HCl and extracted with EtOAc (50 mL×3). The combined organic layers were washed with brine, dried over MgSO$_4$, filtered, and concentrated in vacuo to give the crude product which was used without further purification. LRMS m/z (M+H) 204.1 found, 204.0 required.

The following intermediates were made as described above, replacing 2,2-difluoroethanol with the appropriate alcohol.

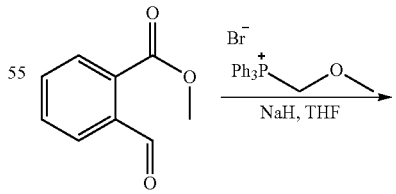

Intermediate Z 2-(2-Methoxyethyl)benzoic Acid

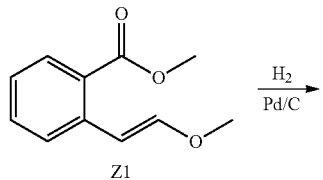

Z1

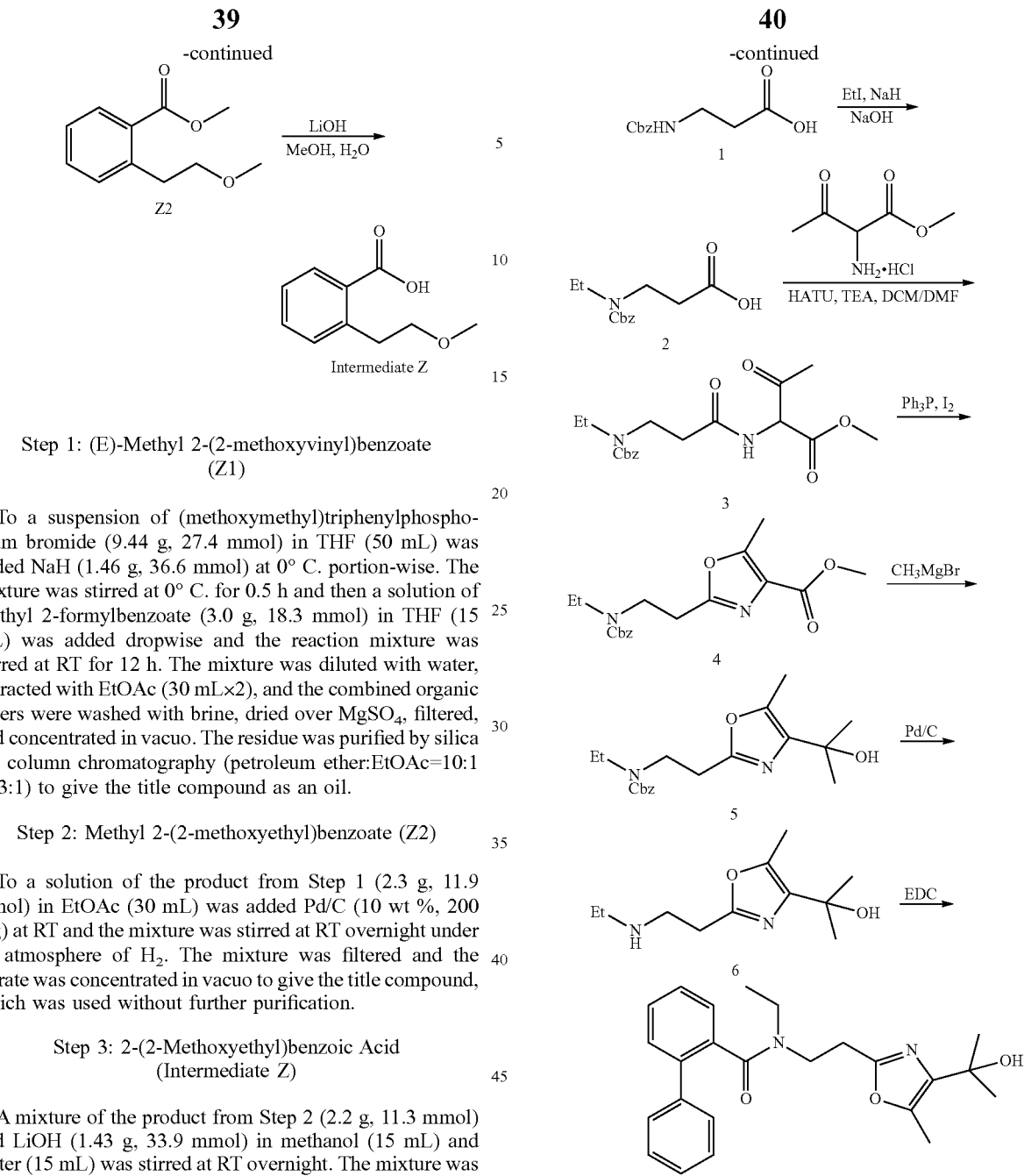

Step 1: (E)-Methyl 2-(2-methoxyvinyl)benzoate (Z1)

To a suspension of (methoxymethyl)triphenylphosphonium bromide (9.44 g, 27.4 mmol) in THF (50 mL) was added NaH (1.46 g, 36.6 mmol) at 0° C. portion-wise. The mixture was stirred at 0° C. for 0.5 h and then a solution of methyl 2-formylbenzoate (3.0 g, 18.3 mmol) in THF (15 mL) was added dropwise and the reaction mixture was stirred at RT for 12 h. The mixture was diluted with water, extracted with EtOAc (30 mL×2), and the combined organic layers were washed with brine, dried over MgSO$_4$, filtered, and concentrated in vacuo. The residue was purified by silica gel column chromatography (petroleum ether:EtOAc=10:1 to 3:1) to give the title compound as an oil.

Step 2: Methyl 2-(2-methoxyethyl)benzoate (Z2)

To a solution of the product from Step 1 (2.3 g, 11.9 mmol) in EtOAc (30 mL) was added Pd/C (10 wt %, 200 mg) at RT and the mixture was stirred at RT overnight under an atmosphere of H$_2$. The mixture was filtered and the filtrate was concentrated in vacuo to give the title compound, which was used without further purification.

Step 3: 2-(2-Methoxyethyl)benzoic Acid (Intermediate Z)

A mixture of the product from Step 2 (2.2 g, 11.3 mmol) and LiOH (1.43 g, 33.9 mmol) in methanol (15 mL) and water (15 mL) was stirred at RT overnight. The mixture was adjusted to ~pH 3 with 1 N HCl and concentrated in vacuo. The residue was extracted with EtOAc (30 mL×3), and the combined organic layers were dried over Na$_2$SO$_4$, filtered, and the filtrate was concentrated in vacuo to give the title compound as a solid, which was used without further purification.

Example 1

N-Ethyl-N-(2-(4-(2-hydroxypropan-2-yl)-5-methyl-oxazol-2-yl)ethyl)-[1,1'-biphenyl]-2-carboxamide

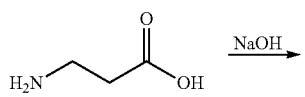

Step 1: 3-(((Benzyloxy)carbonyl)amino)propanoic Acid (1)

To a solution of 3-aminopropanoic acid (50.0 g, 561 mmol) in 2 N NaOH (300 mL) at 0° C. was added Cbz-Cl (115 g, 673 mmol) dropwise. The mixture was adjusted to pH 9-10 with 2 N NaOH and the resulting mixture was stirred at RT overnight, then was extracted with EtOAc (200 mL×3). The aqueous layer was adjusted to pH 2 with 2 N HCl and extracted with EtOAc (200 mL×3) again. The combined organic layers were dried over Na$_2$SO$_4$, filtered, and the filtrate concentrated in vacuo to give the title compound as a solid which was used directly in the next step. LRMS m/z (M+H) 224.1 found, 224.2 required.

Step 2: 3-(((Benzyloxy)carbonyl)(ethyl)amino)propanoic Acid (2)

To a solution of the product from Step 1 (50.0 g, 224 mmol) in DMF (800 mL) at 0° C. was added NaH (22.4 g, 560 mmol). The reaction mixture was stirred at 0° C. for 30 mins, then iodoethane (105 g, 671 mmol) was added and the mixture was stirred at RT for 2 h. Water (100 mL) and NaOH (26.9 g, 672 mmol) were added carefully and the mixture was stirred at RT overnight. The mixture was extracted with EtOAc (300 mL×3). The aqueous phase was adjusted to pH 3 with 2 N HCl, then extracted with EtOAc (400 mL×3). The combined organic layers were dried over $Na_2SO_4$, filtered, and concentrated in vacuo to give the title compound as an oil which was used directly in the next Step. LRMS m/z (M+H) 252.1 found, 252.2 required.

Step 3: Methyl 2-(3-(((benzyloxy)carbonyl)(ethyl)amino)propanamido)-3-oxobutanoate (3)

To a solution of the product from Step 2 (56 g, 223 mmol) in DCM (600 mL) at 0° C. was added HATU (101 g, 267 mmol) and TEA (125 mL, 891 mmol). The mixture was stirred at RT for 30 mins, then a solution of methyl 2-amino-3-oxobutanoate hydrochloride (52.3 g, 312 mmol) in DMF (600 mL) was added dropwise. The reaction mixture was stirred at RT overnight, water (800 mL) was added, and the mixture was extracted with DCM (300 mL×4). The organic layers were combined, washed with brine (200 mL×4), dried over $Na_2SO_4$, filtered, and the filtrate was concentrated in vacuo. The residue was purified by silica gel column chromatography (33% EtOAc in petroleum ether) to give the title compound as an oil. LRMS m/z (M+H) 365.1 found, 365.2 required.

Step 4: Methyl 2-(2-(((benzyloxy)carbonyl)(ethyl)amino)ethyl)-5-methyloxazole-4-carboxylate (4)

To a solution of $I_2$ (68.2 g, 43.9 mmol), $PPh_3$ (70.5 g, 268 mmol), and TEA (56.2 mL, 403 mmol) in DCM (600 mL) at 0° C. was added a solution of the product from Step 3 (49.0 g, 135 mmol) in DCM (200 mL). The resulting mixture was stirred at RT overnight, concentrated in vacuo, and the residue was purified by silica gel column chromatography (33% EtOAc in petroleum ether) to give the title compound as an oil. LRMS m/z (M+H) 347.1 found, 347.2 required.

Step 5: Benzyl ethyl(2-(4-(2-hydroxypropan-2-yl)-5-methyloxazol-2-yl)ethyl)carbamate (5)

To a solution of MeMgBr (34.6 mL, 104 mmol) in dry THF (80 mL) at 0° C. under nitrogen was added a solution of the product from Step 4 (12.0 g, 34.6 mmol) in THF (80 mL) dropwise and the resulting mixture was stirred at 0° C. for 1 h. Saturated, aqueous $NH_4Cl$ was added and the mixture was extracted with EtOAc (40 mL×3). The combined organic layers were dried over $Na_2SO_4$, filtered, and the filtrate was concentrated in vacuo. The residue was purified by silica gel column chromatography (50% EtOAc in petroleum ether) to give the title compound as an oil. LRMS m/z (M+H) 347.1 found, 347.2 required.

Step 6: 2-(2-(2-(Ethylamino)ethyl)-5-methyloxazol-4-yl)propan-2-ol (6)

To a solution of the product from Step 5 (11.6 g, 33.5 mol) in methanol (110 mL) was added Pd/C (10 wt %, 1.16 g). The mixture was stirred at RT under an atmosphere of $H_2$ (15 psi) for 5 hrs. The mixture was filtered and the filtrate was concentrated in vacuo to give the title compound as an oil. LRMS m/z (M+H) 213.1 found, 213.2 required.

Step 7: N-Ethyl-N-(2-(4-(2-hydroxypropan-2-yl)-5-methyloxazol-2-yl)ethyl)-[1,1'-biphenyl]-2-carboxamide (Example 1)

To a solution of the product from Step 6 (25 mg, 0.118 mmol) in DMF (500 µL) was added [1,1'-biphenyl]-2-carboxylic acid (28 mg, 0.141 mmol), followed by EDC hydrochloride (45 mg, 0.24 mmol), Hunig's base (31 mg, 0.24 mmol), and HOAt (16 mg, 0.12 mmol). The solution was stirred at 50° C. overnight. The cooled mixture was diluted with water (2 mL) and extracted with ethyl acetate (3×5 mL). The combined organic layers were washed with brine (15 mL), dried over $NaSO_4$, filtered, and the filtrate was then concentrated in vacuo. The crude product was purified by silica gel column chromatography (0-60% ethyl acetate hexane) to give the title compound as a solid. LRMS m/z (M+H) 393.2 found, 393.2 required.

The following compounds were prepared according to the general procedure provided in Example 1. The starting materials are either prepared as described in the intermediates section, commercially available or may be prepared from commercially available reagents using conventional reactions well known in the art.

| Example | Structure | IUPAC Name | LRMS or HRMS (M + H⁺) |
|---|---|---|---|
| 2 | 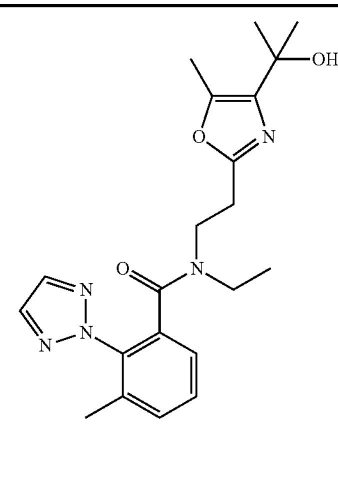 | N-Ethyl-N-{2-[4-(1-hydroxy-1-methylethyl)-5-methyl-1,3-oxazol-2-yl]ethyl}-3-methyl-2-(2H-1,2,3-triazol-2-yl)benzamide | Calc'd 398.0, found 398.2 |

-continued

| Example | Structure | IUPAC Name | LRMS or HRMS (M + H⁺) |
|---|---|---|---|
| 3 | 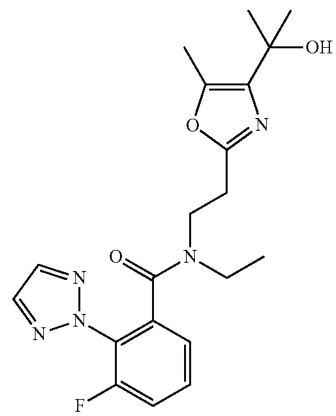 [SMILES: CCN(CCc1nc(C(C)(C)O)c(C)o1)C(=O)c1cccc(F)c1-n1nccn1] | N-Ethyl-3-fluoro-N-{2-[4-(1-hydroxy-1-methylethyl)-5-methyl-1,3-oxazol-2-yl]ethyl}-2-(2H-1,2,3-triazol-2-yl)benzamide | Calc'd 402.0, found 402.2 |
| 4 | 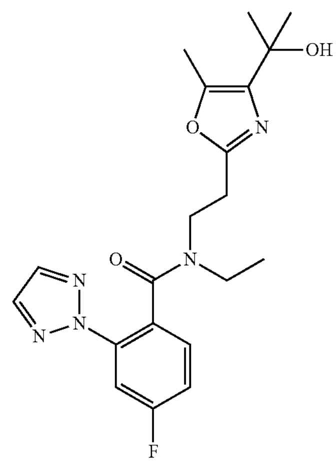 [SMILES: CCN(CCc1nc(C(C)(C)O)c(C)o1)C(=O)c1ccc(F)cc1-n1nccn1] | N-Ethyl-4-fluoro-N-{2-[4-(1-hydroxy-1-methylethyl)-5-methyl-1,3-oxazol-2-yl]ethyl}-2-(2H-1,2,3-triazol-2-yl)benzamide | Calc'd 402.0, found 402.2 |
| 5 | 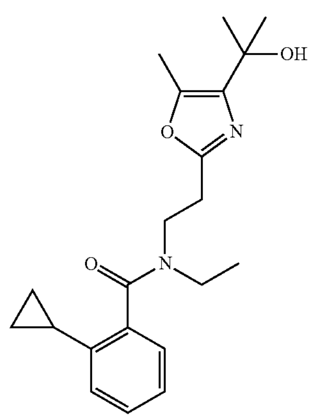 [SMILES: CCN(CCc1nc(C(C)(C)O)c(C)o1)C(=O)c1ccccc1C1CC1] | 2-Cyclopropyl-N-ethyl-N-{2-[4-(1-hydroxy-1-methylethyl)-5-methyl-1,3-oxazol-2-yl]ethyl}benzamide | Calc'd 357.0, found 357.2 |
| 6 | 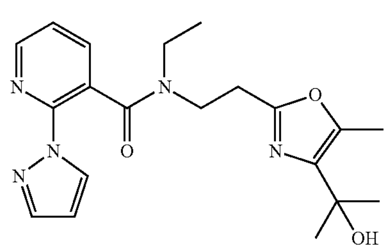 [SMILES: CCN(CCc1nc(C(C)(C)O)c(C)o1)C(=O)c1cccnc1-n1cccn1] | N-Ethyl-N-{2-[4-(1-hydroxy-1-methylethyl)-5-methyl-1,3-oxazol-2-yl]ethyl}-2-(1H-pyrazol-1-yl)pyridine-3-carboxamide | Calc'd 384.0, found 384.2 |

-continued

| Example | Structure | IUPAC Name | LRMS or HRMS (M + H+) |
|---|---|---|---|
| 7 | 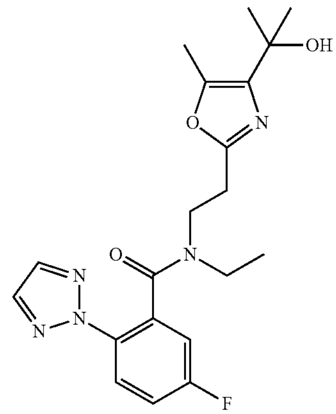 [SMILES: CCN(CCc1nc(C(C)(C)O)c(C)o1)C(=O)c1cc(F)ccc1-n1nccn1] | N-Ethyl-5-fluoro-N-{2-[4-(1-hydroxy-1-methylethyl)-5-methyl-1,3-oxazol-2-yl]ethyl}-2-(2H-1,2,3-triazol-2-yl)benzamide | Calc'd 402.0, found 402.2 |
| 8 | 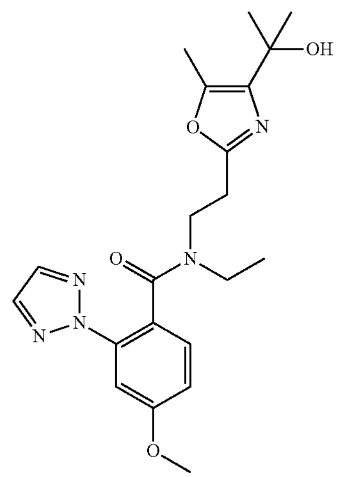 [SMILES: CCN(CCc1nc(C(C)(C)O)c(C)o1)C(=O)c1ccc(OC)cc1-n1nccn1] | N-Ethyl-N-{2-[4-(1-hydroxy-1-methylethyl)-5-methyl-1,3-oxazol-2-yl]ethyl}-4-methoxy-2-(2H-1,2,3-triazol-2-yl)benzamide | Calc'd 414.0, found 414.2 |
| 9 | 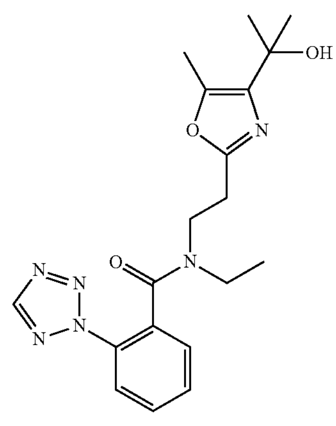 [SMILES: CCN(CCc1nc(C(C)(C)O)c(C)o1)C(=O)c1ccccc1-n1ncnn1] | N-ethyl-N-{2-[4-(1-hydroxy-1-methylethyl)-5-methyl-1,3-oxazol-2-yl]ethyl}-2-(2H-tetrazol-2-yl)benzamide | Calc'd 385.0, found 385.2 |
| 10 | 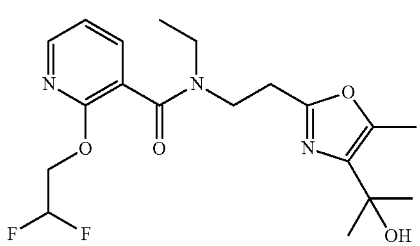 [SMILES: CCN(CCc1nc(C(C)(C)O)c(C)o1)C(=O)c1cccnc1OCC(F)F] | 2-(2,2-difluoroethoxy)-N-ethyl-N-{2-[4-(1-hydroxy-1-methylethyl)-5-methyl-1,3-oxazol-2-yl]ethyl}pyridine-3-carboxamide | Calc'd 398.0, found 398.2 |

| Example | Structure | IUPAC Name | LRMS or HRMS (M + H+) |
|---|---|---|---|
| 10b | 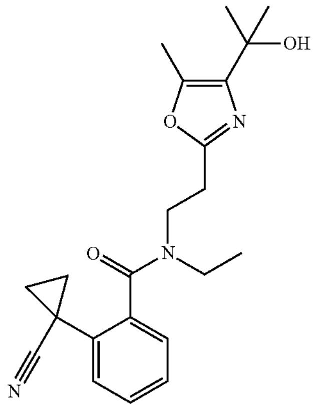 [SMILES: CCN(CCc1nc(C(C)(C)O)c(C)o1)C(=O)c1ccccc1C1(C#N)CC1] | 2-(1-cyanocyclopropyl)-N-ethyl-N-{2-[4-(1-hydroxy-1-methylethyl)-5-methyl-1,3-oxazol-2-yl]ethyl}benzamide | Calc'd 382.2, found 382.3 |
| 10c | 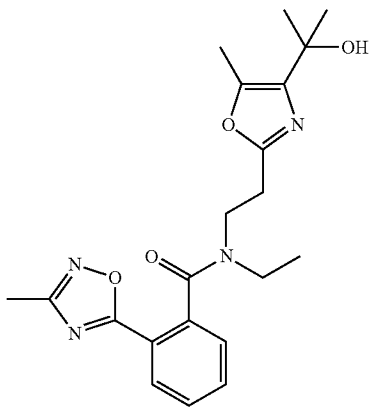 [SMILES: CCN(CCc1nc(C(C)(C)O)c(C)o1)C(=O)c1ccccc1-c1nc(C)no1] | N-ethyl-N-{2-[4-(1-hydroxy-1-methylethyl)-5-methyl-1,3-oxazol-2-yl]ethyl}-2-(3-methyl-1,2,4-oxadiazol-5-yl)benzamide | Calc'd 399.2, found 399.1 |
| 10d | 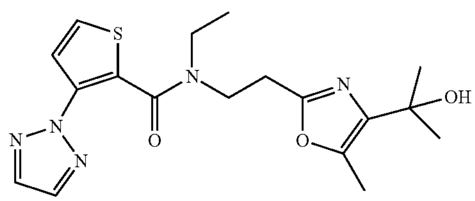 [SMILES: CCN(CCc1nc(C(C)(C)O)c(C)o1)C(=O)c1sccc1-n1nccn1] | N-ethyl-N-{2-[4-(1-hydroxy-1-methylethyl)-5-methyl-1,3-oxazol-2-yl]ethyl}-3-(2H-1,2,3-triazol-2-yl)thiophene-2-carboxamide | Calc'd 390.2, found 390.2 |

Example 11

N-Ethyl-N-{2-[4-(1-hydroxy-1-methylethyl)-5-methyl-1,3-oxazol-2-yl]ethyl}-2-(2H-1,2,3-triazol-2-yl)benzamide

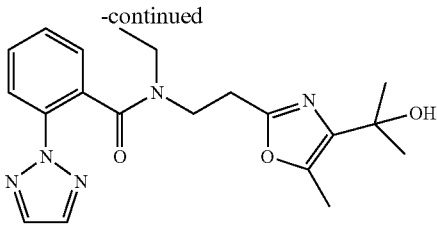

Example 11

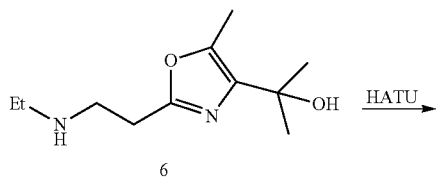

Step 1: N-Ethyl-N-{2-[4-(1-hydroxy-1-methylethyl)-5-methyl-1,3-oxazol-2-yl]ethyl}-2-(2H-1,2,3-triazol-2-yl)benzamide (Example 11)

To a solution of 2-(2H-1,2,3-triazol-2-yl)benzoic acid (40 mg, 0.21 mmol) in 2 mL of DMF was added HATU (96.5 mg, 0.25 mmol) and the mixture was stirred at RT for 10 mins 2-(2-(2-(Ethylamino)ethyl)-5-methyloxazol-4-yl)propan-2-ol (Example 1, Step 6) (45 mg, 0.21 mmol) and TEA (0.08 mL, 0.63 mmol) were added and the mixture was stirred at RT for 1 h and then purified directly by preparative HPLC to give the title compound as an oil. LRMS m/z (M+H) 384.2 found, 384.2 required.

The following compounds were prepared according to the general procedures provided in Examples 1 and 11. The starting materials are either commercially available or may be prepared from commercially available reagents using conventional reactions well known in the art.

| Example | Structure | IUPAC Name | LRMS or HRMS (M + H+) |
|---|---|---|---|
| 12 | 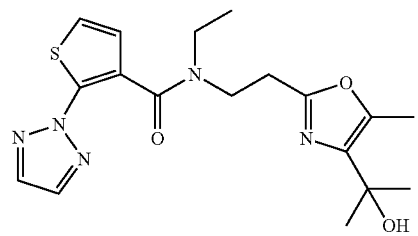 [SMILES: CCN(CCc1nc(C(C)(C)O)c(C)o1)C(=O)c1ccsc1-n1nccn1] | N-Ethyl-N-{2-[4-(1-hydroxy-1-methylethyl)-5-methyl-1,3-oxazol-2-yl]ethyl}-2-(2H-1,2,3-triazol-2-yl)thiophene-3-carboxamide | Calc'd 390.2, found 390.2 |
| 13 | 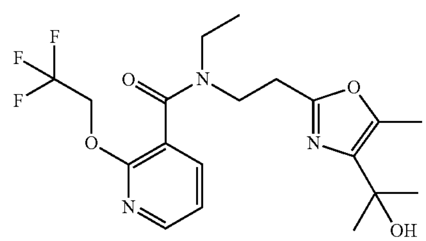 [SMILES: CCN(CCc1nc(C(C)(C)O)c(C)o1)C(=O)c1cccnc1OCC(F)(F)F] | N-Ethyl-N-{2-[4-(1-hydroxy-1-methylethyl)-5-methyl-1,3-oxazol-2-yl]ethyl}-2-(2,2,2-trifluoroethoxy)pyridine-3-carboxamide | Calc'd 416.2, found 416.1 |
| 14 | 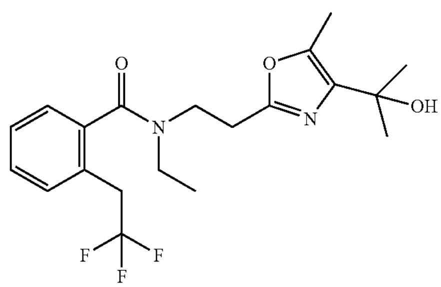 [SMILES: CCN(CCc1nc(C(C)(C)O)c(C)o1)C(=O)c1ccccc1CC(F)(F)F] | N-Ethyl-N-{2-[4-(1-hydroxy-1-methylethyl)-5-methyl-1,3-oxazol-2-yl]ethyl}-2-(2,2,2-trifluoroethyl)benzamide | Calc'd 399.2, found 399.1 |
| 15 | 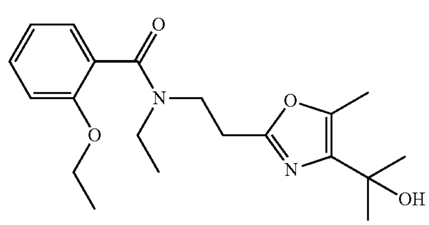 [SMILES: CCOc1ccccc1C(=O)N(CC)CCc1nc(C(C)(C)O)c(C)o1] | 2-Ethoxy-N-ethyl-N-{2-[4-(1-hydroxy-1-methylethyl)-5-methyl-1,3-oxazol-2-yl]ethyl}benzamide | Calc'd 361.2, found 361.1 |
| 16 | 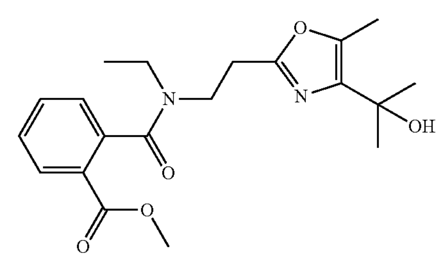 [SMILES: CCN(CCc1nc(C(C)(C)O)c(C)o1)C(=O)c1ccccc1C(=O)OC] | Methyl 2-(ethyl{2-[4-(1-hydroxy-1-methylethyl)-5-methyl-1,3-oxazol-2-yl]ethyl}carbamoyl)benzoate | Calc'd 375.2, found 375.1 |

| Example | Structure | IUPAC Name | LRMS or HRMS (M + H⁺) |
|---|---|---|---|
| 17 | 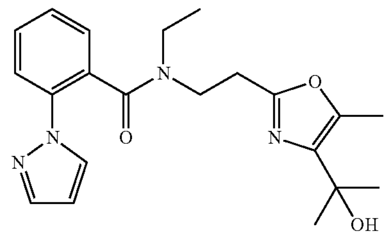 [SMILES: CCN(CCc1nc(C(C)(C)O)c(C)o1)C(=O)c1ccccc1-n1cccn1] | N-Ethyl-N-{2-[4-(1-hydroxy-1-methylethyl)-5-methyl-1,3-oxazol-2-yl]ethyl}-2-(1H-pyrazol-1-yl)benzamide | Calc'd 383.0, found 383.1 |
| 18b | 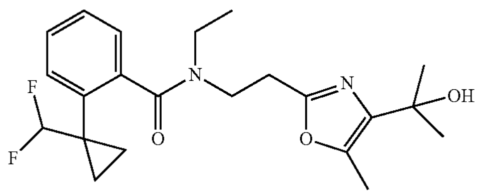 [SMILES: CCN(CCc1nc(C(C)(C)O)c(C)o1)C(=O)c1ccccc1C1(C(F)F)CC1] | 2-(1-(difluoromethyl)cyclopropyl)-N-ethyl-N-(2-(4-(2-hydroxypropan-2-yl)-5-methyloxazol-2-yl)ethyl)benzamide | Calc'd 407.2, found 407.1 |

Example 19

N-Ethyl-N-{2-[4-(1-hydroxy-1-methylpropyl)-5-methyl-1,3-oxazol-2-yl]ethyl}-2-(2H-1,2,3-triazol-2-yl)benzamide

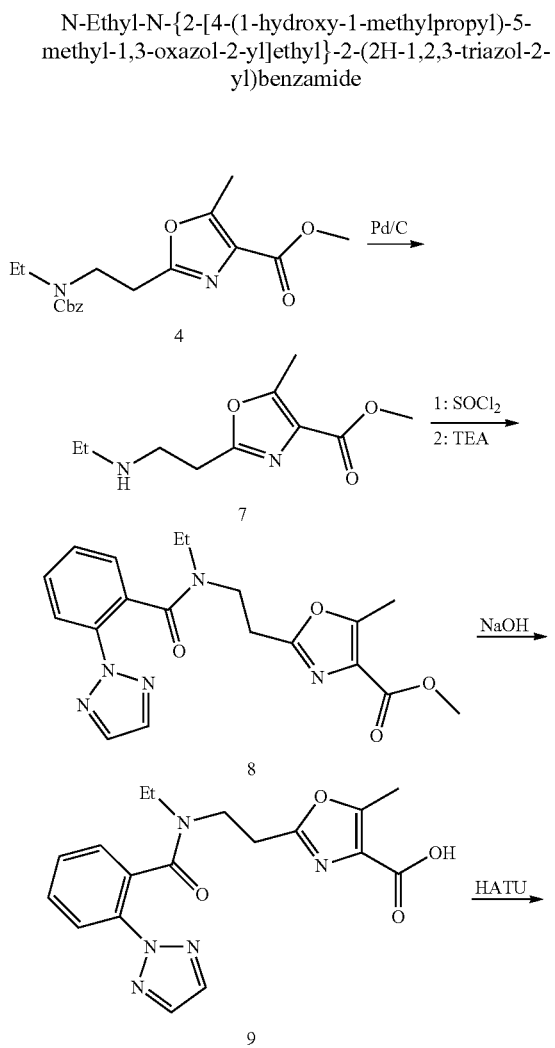

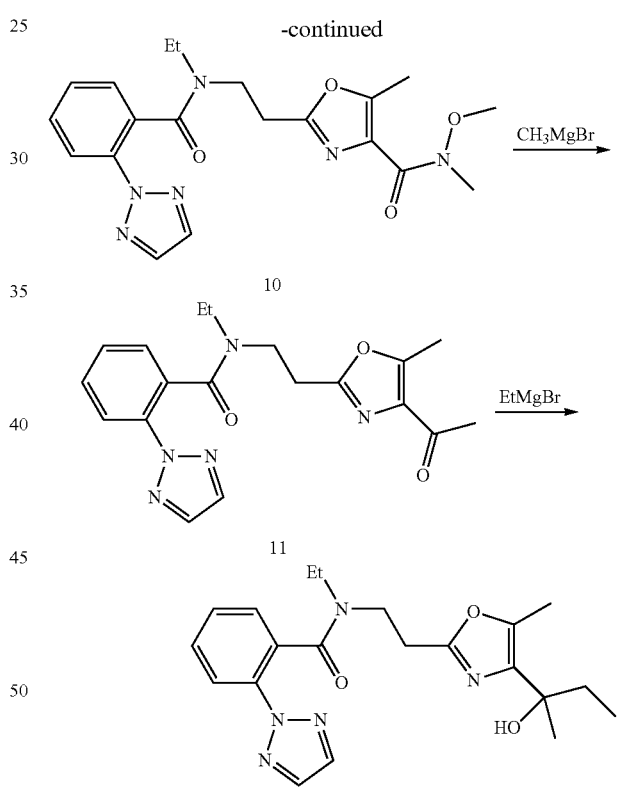

Example 19

Step 1: Methyl 2-(2-(ethylamino)ethyl)-5-methyloxazole-4-carboxylate (7)

To a solution of methyl 2-(2-(((benzyloxy)carbonyl)(ethyl)amino)ethyl)-5-methyloxazole-4-carboxylate (Example 1, Step 4) (1.90 g, 5.49 mol) in MeOH (20 mL) was added Pd/C (10 wt %, 190 mg) at RT. The resulting mixture was stirred for 1 h under an atmosphere of H₂ (15 psi) and then filtered. The filtrate was concentrated in vacuo to give the title compound as an oil which was used in the next step without further purification. LRMS m/z (M+H) 213.1 found, 213.2 required.

Step 2: Methyl 2-(2-((2-(2H-1,2,3-triazol-2-yl)benzyl)(ethyl)amino)ethyl)-5-methyloxazole-4-carboxylate (8)

To a solution of 2-(2H-1,2,3-triazol-2-yl)benzoic acid (600 mg, 3.17 mmol) in toluene (6 mL) was added $SOCl_2$ (0.46 mL, 6.34 mmol) and the resulting mixture was heated at 80° C. for 1 h. The cooled mixture was concentrated in vacuo, dissolved in DCM (5 mL), and added dropwise to a solution of the product from Step 1 (470 mg, 2.21 mmol) and TEA (0.93 mL, 6.64 mmol) in DCM (10 mL). The resulting mixture was stirred at RT for 30 mins and then concentrated in vacuo. The residue was purified by silica gel column chromatography (50% EtOAc in petroleum ether) to give the title compound as an oil. LRMS m/z (M+H) 384.1 found, 384.2 required.

Step 3: 2-(2-(N-Ethyl-2-(2H-1,2,3-triazol-2-yl)benzamido)ethyl)-5-methyloxazole-4-carboxylic Acid (9)

To a solution of the product from Step 2 (750 mg, 1.96 mmol) in MeOH (10 mL) were added NaOH (156 mg, 3.91 mmol) and water (0.1 mL) and the mixture was stirred at RT overnight. The mixture was adjusted to pH 2 with 2 N HCl, and then was extracted with EtOAc (5 mL×3); the combined organic layers were dried over $Na_2SO_4$, filtered, and the filtrate was concentrated in vacuo to give the title compound as an oil. LRMS m/z (M+H) 370.1 found, 370.2 required.

Step 4: 2-(2-(N-Ethyl-2-(2H-1,2,3-triazol-2-yl)benzamido)ethyl)-N-methoxy-N,5-dimethyloxazole-4-carboxamide (10)

To a solution of the product from Step 3 (710 mg, 1.92 mmol) in DCM (15 mL) were added HATU (877 mg, 2.31 mmol), N,O-dimethylhydroxylamine hydrochloride (281 mg, 2.88 mmol), and TEA (0.80 mL, 5.77 mmol), and the resulting mixture was stirred at RT overnight. The mixture was concentrated in vacuo and purified by silica gel column chromatography (50% EtOAc in petroleum ether) to give the title compound as an oil. LRMS m/z (M+H) 413.1 found, 413.2 required.

Step 5: N-(2-(4-Acetyl-5-methyloxazol-2-yl)ethyl)-N-ethyl-2-(2H-1,2,3-triazol-2-yl)benzamide (11)

To a solution of MeMgBr (3 M, 0.67 mL, 2 mmol) in dry THF (5 mL) at 0° C. under nitrogen was added dropwise a solution of the product from Step 4 (750 mg, 1.82 mmol) in THF (5 mL). The resulting mixture was stirred at RT for 2 h, and then saturated, aqueous $NH_4Cl$ was added and the mixture was extracted with EtOAc (5 mL×3). The combined organic layers were dried over $Na_2SO_4$, filtered, and the filtrate was concentrated in vacuo. The residue was purified by silica gel column chromatography (50% EtOAc in petroleum ether) to give the title compound as an oil. LRMS m/z (M+H) 368.2 found, 368.2 required.

Step 6: N-Ethyl-N-{2-[4-(1-hydroxy-1-methylpropyl)-5-methyl-1,3-oxazol-2-yl]ethyl}-2-(2H-1,2,3-triazol-2-yl)benzamide (Example 19)

To a solution of EtMgBr (3 M, 0.53 mL, 1.59 mmol) in dry THF (1 mL) at 0° C. under nitrogen was added dropwise a solution of the product from Step 5 (195 mg, 0.53 mmol) in THF (2 mL) and the resulting mixture was stirred at RT for 1.5 h. Saturated, aqueous $NH_4Cl$ was added and the mixture was extracted with EtOAc (5 mL×3). The combined organic layers were dried over $Na_2SO_4$, filtered, and the filtrate was concentrated in vacuo. The residue was purified by preparative HPLC to give the title compound as an oil. LRMS m/z (M+H) 398.2 found, 398.0 required.

Example 20

N-Ethyl-N-{2-[4-(1-hydroxy-1,2-dimethylpropyl)-5-methyl-1,3-oxazol-2-yl]ethyl}-2-(2H-1,2,3-triazol-2-yl)benzamide

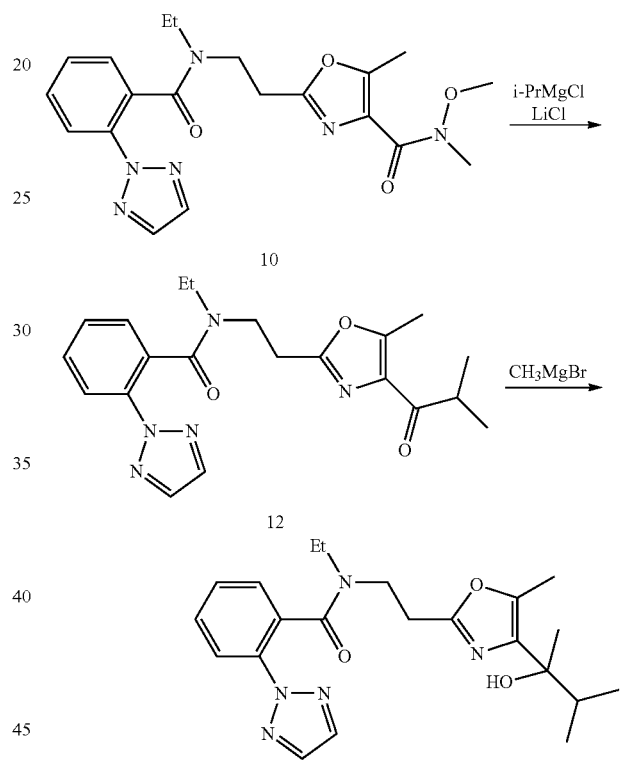

Example 20

Step 1: N-ethyl-N-(2-(4-isobutyryl-5-methyloxazol-2-yl)ethyl)-2-(2H-1,2,3-triazol-2-yl)benzamide (12)

To a solution of 2-(2-(N-ethyl-2-(2H-1,2,3-triazol-2-yl)benzamido)ethyl)-N-methoxy-N,5-dimethyloxazole-4-carboxamide (Example 19, Step 4) (130 mg, 0.32 mmol) in THF (2 mL) at −78° C. was added dropwise i-PrMgCl LiCl (0.27 mL, 0.35 mmol). The resulting mixture was allowed to warm to RT and stirred overnight. Additional i-PrMgCl LiCl (0.54 mL, 0.70 mmol) was added at RT and the resulting mixture was stirred at RT overnight. Saturated, aqueous $NH_4Cl$ was added and the mixture was extracted with EtOAc (5 mL×3). The organic layers were combined, dried over $Na_2SO_4$, filtered, and the filtrate was concentrated in vacuo. The residue was purified by preparative TLC (33% EtOAc in petroleum ether) to give the desired product as an oil. LRMS m/z (M+H) 396.2 found, 396.2 required.

Step 2: N-Ethyl-N-{2-[4-(1-hydroxy-1,2-dimethyl-propyl)-5-methyl-1,3-oxazol-2-yl]ethyl}-2-(2H-1,2,3-triazol-2-yl)benzamide (Example 20)

To a solution of the product from Step 1 (50 mg, 0.13 mmol) in THF (2 mL) at −78° C. was added dropwise MeMgBr (0.3 M, 0.46 mL, 0.14 mmol) and the resulting mixture was stirred at RT for 1 h. Additional MeMgBr (0.3 M, 0.46 mL, 0.14 mmol) was added and the mixture was stirred at RT overnight. Saturated, aqueous NH$_4$Cl was added and the mixture was extracted with EtOAc (5 mL×3). The combined organic layers were dried over Na$_2$SO$_4$, filtered, and the filtrate concentrated in vacuo. The residue was purified by preparative TLC (33% EtOAc in petroleum ether) to give the desired product as an oil. LRMS m/z (M+H) 412.4 found, 412.0 required.

Example 21

N-{2-[4-(1-Hydroxy-1-methylethyl)-5-methyl-1,3-oxazol-2-yl]ethyl}-N-prop-2-en-1-yl-2-(2H-1,2,3-triazol-2-yl)benzamide

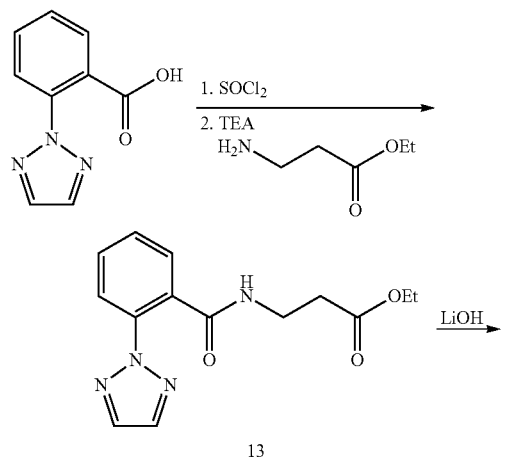

13

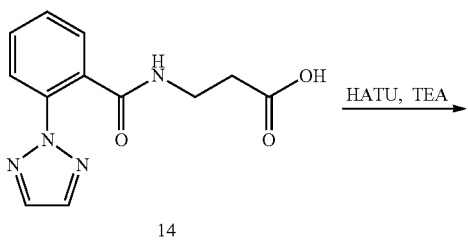

14

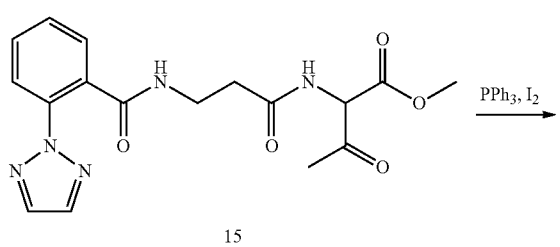

15

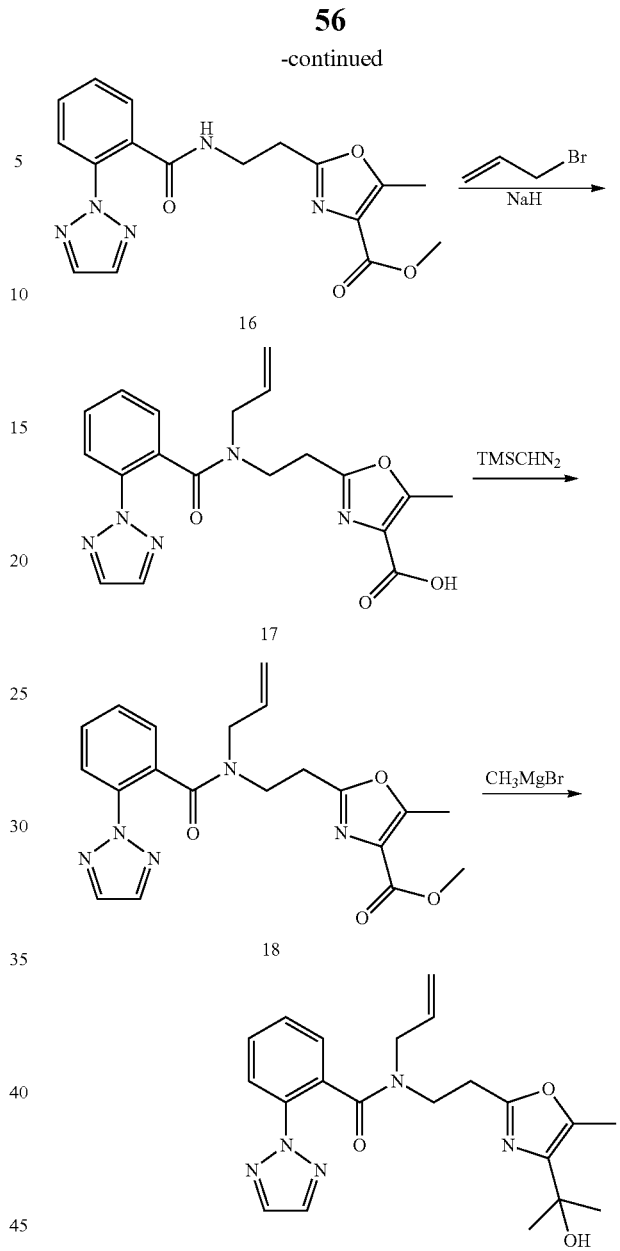

16

17

18

Example 21

Step 1: Ethyl 3-(2-(2H-1,2,3-triazol-2-yl)benzamido)propanoate (13)

To a solution of 2-(2H-1,2,3-triazol-2-yl)benzoic acid (5.0 g, 26.5 mmol) in dry DCM (50 mL) was added SOCl$_2$ (6 mL). The mixture was stirred at 50° C. for 2 h and the cooled mixture was concentrated in vacuo and dissolved in DCM (50 mL) to form solution A. To a solution of ethyl 3-amino-propanoate (4.0 g, 26.5 mmol) in dry DCM (20 mL) at 0° C. was added TEA (12 mL) and then solution A was added at 0° C. The mixture was stirred at RT for 30 mins, then was poured into water and extracted with EtOAc (3×100 mL). The combined organic layers were dried over MgSO$_4$, filtered, and concentrated in vacuo to give the title compound as a solid. LRMS m/z (M+H) 289.1 found, 289.2 required.

Step 2: 3-(2-(2H-1,2,3-Triazol-2-yl)benzamido)propanoic Acid (14)

To a solution of the product from Step 1 (5.0 g, 17.4 mmol) in EtOH/H$_2$O (50 mL/5 mL) was added LiOH (2.1 g, 86.8 mmol) and the mixture was stirred at RT for 6 h. The mixture was extracted with EtOAc (50 mL×3). The pH of the aqueous layer was adjusted to ~3-4 by addition of 2 N HCl and then extracted with EtOAc (50 mL×3). The combined organic layers were dried over MgSO$_4$, filtered, and concentrated in vacuo to give the title compound as a solid. LRMS m/z (M+H) 261.1 found, 261.2 required.

Step 3: Methyl 2-(3-(2-(2H-1,2,3-triazol-2-yl)benzamido)propanamido)-3-oxobutanoate (15)

A solution of the product from Step 2 (2.0 g, 6.94 mmol), methyl 2-amino-3-oxobutanoate hydrochloride (2.0 g, 12.0 mmol), HATU (2.9 g, 7.6 mmol), and TEA (3.0 mL) in DCM (40 mL) was stirred at RT overnight. The mixture was filtered and the filtrate was concentrated in vacuo. The residue was purified by silica gel column chromatography (10-33% EtOAc in petroleum ether) to give the title compound as an oil. LRMS m/z (M+H) 374.1 found, 374.2 required.

Step 4: Methyl 2-(2-(2-(2H-1,2,3-triazol-2-yl)benzamido)ethyl)-5-methyloxazole-4-carboxylate (16)

To a solution of I$_2$ (2.70 g, 10.6 mmol), Ph$_3$P (2.80 g, 10.6 mmol), and TEA (3.0 mL, 21.2 mmol) in DCM (30 mL) was added a solution of the product from Step 3 (2.0 g, 5.3 mmol) in DCM (15 mL). The resulting mixture was stirred at RT for 3 h, poured into water, and extracted with DCM (30 mL×3). The combined organic layers were washed with brine, dried over MgSO$_4$, filtered, and concentrated in vacuo. The residue was purified by silica gel column chromatography (10-50% EtOAc in petroleum ether) to give the title compound as an oil. LRMS m/z (M+H) 356.1 found, 356.2 required.

Step 5: 2-(2-(N-Allyl-2-(2H-1,2,3-triazol-2-yl)benzamido)ethyl)-5-methyloxazole-4-carboxylic Acid (17)

To a solution of the product from Step 4 (100 mg, 0.28 mmol) in THF (5 mL) at 0° C. was added NaH (13 mg, 0.31 mmol). After 30 mins, allyl bromide (0.3 mL) was added dropwise. The resulting mixture was stirred at RT overnight, diluted with 10 mL of water, and extracted with EtOAc (10 mL×2). The aqueous layer was adjusted to pH ~4 with 4 N HCl, then extracted with EtOAc (10 mL×3). The combined organic layers were dried over MgSO$_4$, filtered, and concentrated in vacuo to give the title compound as an oil. LRMS m/z (M+H) 382.1 found, 382.2 required.

Step 6: Methyl 2-(2-(N-allyl-2-(2H-1,2,3-triazol-2-yl)benzamido)ethyl)-5-methyloxazole-4-carboxylate (18)

To a solution of the product from Step 5 (100 mg, 0.26 mmol) in DCM/methanol (5.0 mL/1.0 mL) at 0° C. was added dropwise TMSCHN$_2$ (0.3 mL, 0.55 mmol). The resulting mixture was stirred at 0° C. for 15 mins. Acetic acid was added, the mixture was concentrated in vacuo, and the crude product was purified by preparative TLC to give the title compound as an oil. LRMS m/z (M+H) 396.1 found, 396.2 required.

Step 7: N-{2-[4-(1-hydroxy-1-methylethyl)-5-methyl-1,3-oxazol-2-yl]ethyl}-N-prop-2-en-1-yl-2-(2H-1,2,3-triazol-2-yl)benzamide (Example 21)

To a solution of the product from Step 6 (60 mg, 0.15 mmol) in THF (5.0 mL) was added MeMgBr solution (3.0 M, 0.5 mL, 1.5 mmol) and the mixture was stirred at RT overnight. Water was added and the mixture was extracted with EtOAc (10.0 mL×3). The combined organic layers were washed with brine, dried over Na$_2$SO$_4$, filtered, and concentrated in vacuo. The residue was purified by preparative HPLC to give the title compound as a solid. LRMS m/z (M+H) 396.1 found, 396.2 required.

Example 22

N-{2-[4-(1-Hydroxy-1-methylethyl)-5-methyl-1,3-oxazol-2-yl]ethyl}-N-propyl-2-(2H-1,2,3-triazol-2-yl)benzamide

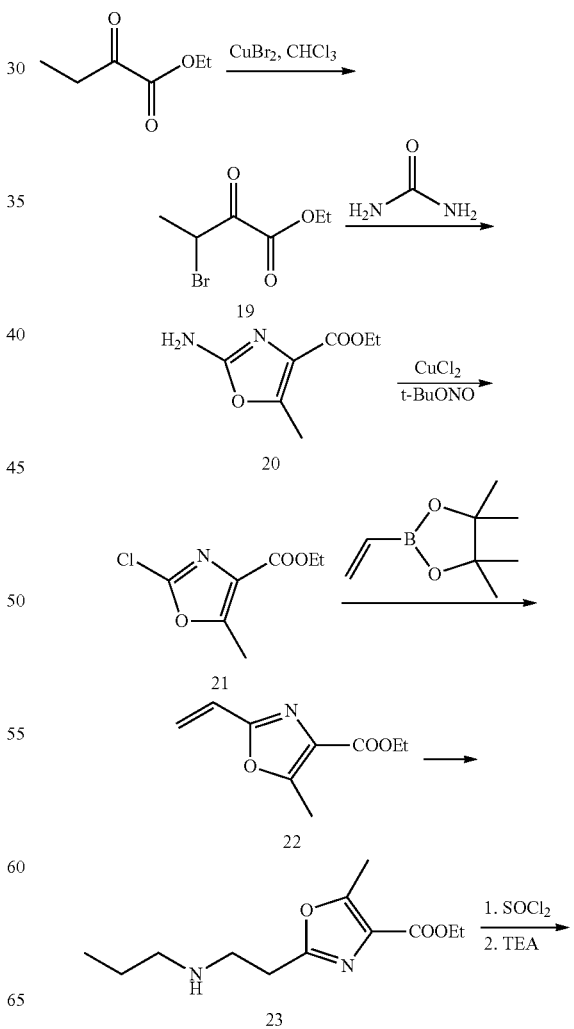

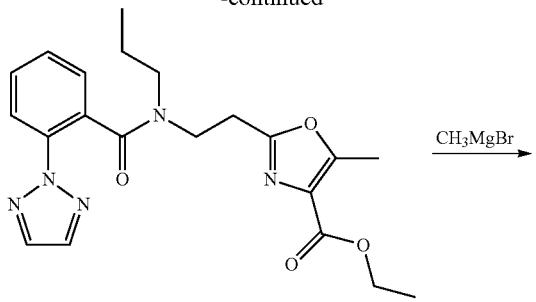

24

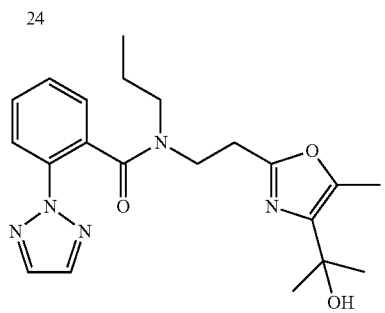

Example 22

Step 1: Ethyl 3-bromo-2-oxobutanoate (19)

To a suspension of CuBr₂ (25.76 g, 115 mmol) in EtOAc (350 mL) was added a solution of ethyl 2-oxobutanoate (5 g, 38.5 mmol) in CHCl₃ (150 mL), and the mixture was heated at 80° C. overnight. After cooling to RT, the mixture was filtered and the filtrate was concentrated in vacuo to give the title compound as an oil which was used directly in the next step. LRMS m/z (M+H) 209.1, 211.1 found, 209.2, 211.2 required.

Step 2: Ethyl 2-amino-5-methyloxazole-4-carboxylate (20)

To a solution of the product from Step 1 (8.0 g, 38 mmol) in EtOH (100 mL) was added urea (9.24 g, 154 mmol) at RT and the reaction mixture was heated at 80° C. overnight. The cooled mixture was concentrated in vacuo, diluted with water (50 mL), and extracted with DCM (50 mL×4). The combined organic layers were dried over Na₂SO₄ and filtered. The filtrate was concentrated in vacuo to give the title compound as a solid which was used directly in the next step. LRMS m/z (M+H) 171.1 found, 171.2 required.

Step 3: Ethyl 2-chloro-5-methyloxazole-4-carboxylate (21)

To a mixture of tert-butyl nitrite (1.82 g, 17.6 mmol) and copper(II) chloride (2.37 g, 17.6 mmol) in acetonitrile (50 mL) at 60° C. was added the product from Step 2 (2.0 g, 11.8 mmol) in portions. The mixture was then heated at 80° C. for 2 h, cooled to RT, and concentrated in vacuo. The residue was purified by column silica gel column chromatography (0-20% EtOAc in petroleum ether) to give the title compound as an oil. LRMS m/z (M+H) 190.1, 192.1 found, 190.2, 192.1 required.

Step 4: Ethyl 5-methyl-2-vinyloxazole-4-carboxylate (22)

To a mixture of 4,4,5,5-tetramethyl-2-vinyl-1,3,2-dioxaborolane (650 mg, 4.22 mmol), the product from Step 3 (400 mg, 2.110 mmol), and K₂CO₃ (583 mg, 4.22 mmol) in 1,4-dioxane (4 mL) and water (0.8 mL) was added Pd(dppf)Cl₂ (86 mg, 0.105 mmol). The mixture was heated at 100° C. overnight. The cooled mixture was filtered and the filtrate was concentrated in vacuo. The residue was purified by preparative TLC (20% EtOAc in petroleum ether) to give the title compound as an oil. LRMS m/z (M+H) 182.1 found, 182.1 required.

Step 5: Ethyl 5-methyl-2-(2-(propylamino)ethyl)oxazole-4-carboxylate (23)

To a solution of the product from Step 4 (100 mg, 0.552 mmol) in ethanol (5 mL) was added propan-1-amine (36 mg, 0.607 mmol), and the mixture was heated to reflux for 18 h. The cooled mixture was concentrated in vacuo and purified by preparative TLC (67% EtOAc in petroleum ether) to give the title compound as an oil. LRMS m/z (M+H) 241.1 found, 241.2 required.

Step 6: Ethyl 5-methyl-2-(2-(N-propyl-2-(2H-1,2,3-triazol-2-yl)benzamido)ethyl)oxazole-4-carboxylate (24)

To a solution of 2-(2H-1,2,3-triazol-2-yl)benzoic acid (63.0 mg, 0.333 mmol) in DCM (5 mL) at RT was added SOCl₂ (0.049 mL, 0.67 mmol) and the mixture was heated at 50° C. for 2 h. The reaction was cooled and concentrated in vacuo, dissolved in 5 mL of DCM, and the product from Step 5 (80 mg, 0.333 mmol) was added. The resulting mixture was cooled at 0° C., TEA (0.093 mL, 0.666 mmol) was added slowly, and the mixture was stirred at 0° C. for 20 mins. Water (5 mL) was added and the mixture was extracted with DCM (5 mL×3). The combined organic layers were dried with Na₂SO₄ and filtered, and the filtrate was concentrated in vacuo to give the title compound as an oil. LRMS m/z (M+H) 412.1 found, 412.2 required.

Step 7: N-{2-[4-(1-Hydroxy-1-methylethyl)-5-methyl-1,3-oxazol-2-yl]ethyl}-N-propyl-2-(2H-1,2,3-triazol-2-yl)benzamide (Example 22)

MeMgBr (3.0 M, 0.405 mL, 1.21 mmol) was added slowly to a solution of the product from Step 6 (100 g, 0.24 mmol) in THF (5 mL) at 0° C. The resulting mixture was stirred at 0° C. for 1 h. Saturated, aqueous NH₄Cl (2 mL) was added and the mixture was extracted with EtOAc (10 mL×3). The combined organic layers were dried over Na₂SO₄ and filtered, and the filtrate was concentrated in vacuo. The residue was purified by preparative HPLC to give the title compound as an oil. LRMS m/z (M+H) 398.4 found, 398.2 required.

Example 23

N-(Cyclopropylmethyl)-N-{2-[4-(1-hydroxy-1-methylethyl)-5-methyl-1,3-oxazol-2-yl]ethyl}-2-(2H-1,2,3-triazol-2-yl)benzamide

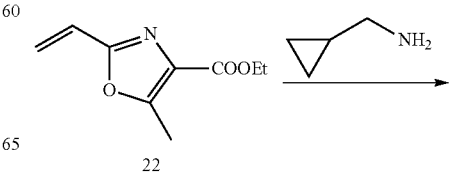

22

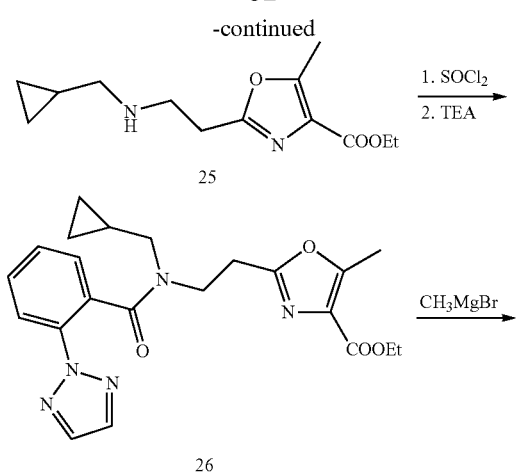

Example 23

Step 1: Ethyl 2-(2-((cyclopropylmethyl)amino)ethyl)-5-methyloxazole-4-carboxylate (25)

To a solution of ethyl 5-methyl-2-vinyloxazole-4-carboxylate (Example 22, Step 4) (150 mg, 0.828 mmol) in EtOH (5 mL) was added cyclopropylmethanamine (65 mg, 0.99 mmol) and the resulting mixture was heated at reflux for 18 h. The cooled mixture was concentrated in vacuo and the residue purified by preparative TLC (67% EtOAc in petroleum ether) to give the title compound as an oil. LRMS m/z (M+H) 253.1 found, 253.2 required.

Step 2: Ethyl 2-(2-(N-(cyclopropylmethyl)-2-(2H-1,2,3-triazol-2-yl)benzamido)ethyl)-5-methyloxazole-4-carboxylate (26)

To a solution of 2-(2H-1,2,3-triazol-2-yl)benzoic acid (100 mg, 0.53 mmol) in DCM (5 mL) was added SOCl₂ (314 mg, 2.64 mmol) at RT. The mixture was heated at 50° C. for 2 h, cooled, and concentrated in vacuo. The residue was dissolved in DCM (5 mL) and the product from Step 1 (160 mg, 0.634 mmol) was added. The resulting mixture was cooled at 0° C. and TEA (0.147 mL, 1.057 mmol) was added slowly. After addition, the mixture was stirred at 0° C. for 20 mins. Water (5 mL) was added and the mixture was extracted with DCM (5 mL×3). The combined organic layers were dried over Na₂SO₄, filtered, and the filtrate was concentrated in vacuo. The residue was purified by preparative TLC (50% EtOAc in petroleum ether) to give the title compound as an oil. LRMS m/z (M+H) 424.2 found, 424.2 required.

Step 3: N-(Cyclopropylmethyl)-N-{2-[4-(1-hydroxy-1-methylethyl)-5-methyl-1,3-oxazol-2-yl]ethyl}-2-(2H-1,2,3-triazol-2-yl)benzamide (Example 23)

MeMgBr (3.0 M, 0.163 mL, 0.488 mmol) was added dropwise to a solution of the product from Step 2 (40 mg, 0.098 mmol) in THF (3 mL) at 0° C. The resulting mixture was stirred at 0° C. for 1 h. Saturated, aqueous NH₄Cl (2 mL) was added and the mixture was extracted with EtOAc (10 mL×3). The combined organic layers were dried over Na₂SO₄, filtered, and the filtrate was concentrated in vacuo. The residue was purified by preparative HPLC to give the title compound as a solid. LRMS m/z (M+H) 410.1 found, 410.0 required.

Example 24

N-(2,2-Difluoroethyl)-N-{2-[4-(1-hydroxy-1-methylethyl)-5-methyl-1,3-oxazol-2-yl]ethyl}-2-(2H-1,2,3-triazol-2-yl)benzamide

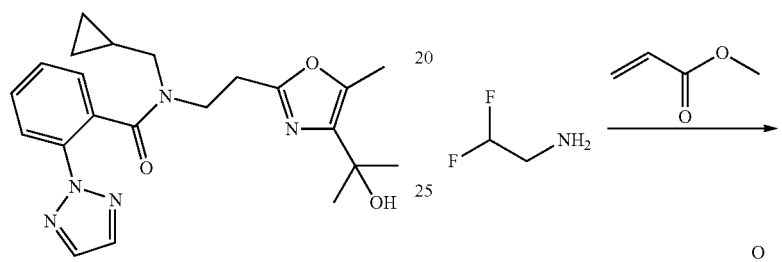

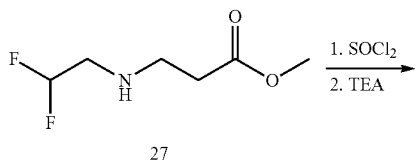

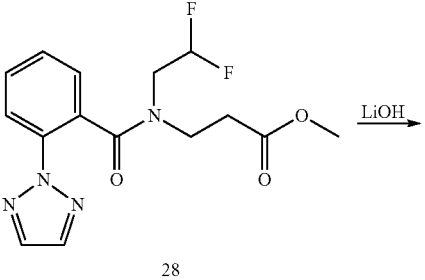

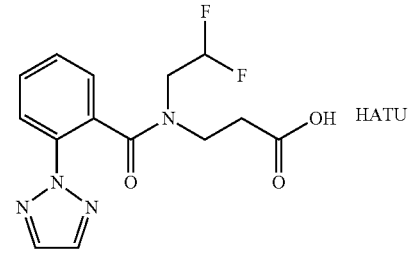

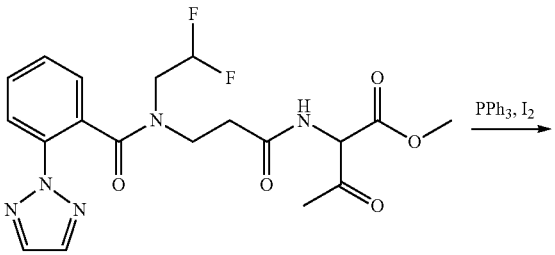

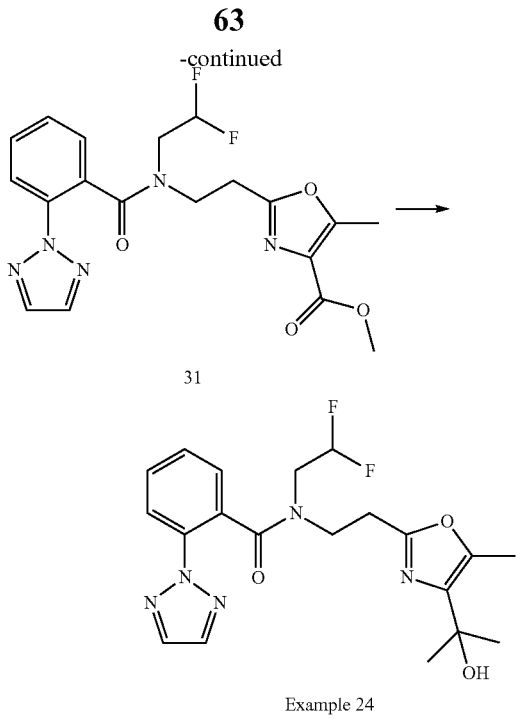

Example 24

Step 1: Methyl 3-((2,2-difluoroethyl)amino)propanoate (27)

To a solution of 2,2-difluoroethanamine (3.53 g, 43.6 mmol) in methanol (10 mL) at RT was added methyl acrylate (2.5 g, 29.0 mmol). The reaction was stirred at RT overnight and concentrated in vacuo to give the title compound as an oil. LRMS m/z (M+H) 168.1 found, 168.2 required.

Step 2: Methyl 3-(N-(2,2-difluoroethyl)-2-(2H-1,2,3-triazol-2-yl)benzamido)propanoate (28)

To a solution of 2-(2H-1,2,3-triazol-2-yl)benzoic acid (450 mg, 2.38 mmol) in DCM (5 mL) was added $SOCl_2$ (1.42 g, 11.89 mmol) at RT and the mixture was heated at 50° C. for 2 h. The cooled mixture was then concentrated in vacuo and dissolved in DCM (5 mL), and the product from Step 1 (477 mg, 2.85 mmol) was added. The mixture was cooled at 0° C. and TEA (0.66 mL, 4.76 mmol) was added slowly. The mixture was stirred at 0° C. for 20 mins. Water (10 mL) was added and the mixture was extracted with DCM (20 mL×3). The combined organic layers were dried over $Na_2SO_4$, filtered, and the filtrate was concentrated in vacuo to give the title compound as an oil. LRMS m/z (M+H) 339.1 found, 339.2 required.

Step 3: 3-(N-(2,2-Difluoroethyl)-2-(2H-1,2,3-triazol-2-yl)benzamido)propanoic Acid (29)

To a solution of the product from Step 2 (750 mg, 2.217 mmol) in methanol/$H_2O$ (10 mL/1 mL) at RT was added lithium hydroxide (265 mg, 11.1 mmol). The resulting mixture was stirred at RT for 12 h, diluted with water (10 mL), and washed with EtOAc (10 mL×2). The pH was adjusted to ~3 with HCl, and the solution was extracted with DCM (20 mL×3). The combined organic layers were washed with brine (20 mL), dried over $Na_2SO_4$ and filtered, and the filtrate was concentrated in vacuo to give the title compound as an oil. LRMS m/z (M+H) 325.1 found, 325.2 required.

Step 4: Methyl 2-(3-(N-(2,2-difluoroethyl)-2-(2H-1,2,3-triazol-2-yl)benzamido)propanamido)-3-oxobutanoate (30)

A solution of the product from Step 3 (300 mg, 0.925 mmol), HATU (422 mg, 1.11 mmol), and methyl 2-amino-3-oxobutanoate hydrochloride (233 mg, 1.388 mmol) in DCM (15 mL) was stirred at RT for 20 mins. TEA (0.387 mL, 2.78 mmol) was added and the mixture was stirred at RT for 2 h, poured into water, and extracted with DCM (20 mL×3). The combined organic layers were washed with brine, dried over $MgSO_4$, and filtered, and the filtrate was concentrated in vacuo. The residue was purified by preparative TLC (67% EtOAc in petroleum ether) to give the title compound as an oil. LRMS m/z (M+H) 438.1 found, 438.2 required.

Step 5: Methyl 2-(2-(N-(2,2-difluoroethyl)-2-(2H-1,2,3-triazol-2-yl)benzamido)ethyl)-5-methyloxazole-4-carboxylate (31)

To a solution of $I_2$ (348 mg, 1.372 mmol), triphenylphosphine (360 mg, 1.372 mmol), and TEA (0.382 mL, 2.74 mmol) in DCM (20 mL) was added a solution of the product from Step 4 (300 mg, 0.686 mmol) in DCM (10 mL). The resulting mixture was stirred at RT overnight and concentrated in vacuo. The residue was purified by silica gel column chromatography (67% EtOAc in petroleum ether) to give the title compound as an oil. LRMS m/z (M+H) 420.1 found, 420.2 required.

Step 6: N-(2,2-Difluoroethyl)-N-{2-[4-(1-hydroxy-1-methylethyl)-5-methyl-1,3-oxazol-2-yl]ethyl}-2-(2H-1,2,3-triazol-2-yl)benzamide (Example 24)

MeMgBr (3.0 M, 0.795 mL, 2.38 mmol) was added slowly to a solution of the product from Step 5 (200 mg, 0.477 mmol) in THF (10 mL) at 0° C. The reaction mixture was stirred at 0° C. for 1 h, then saturated aqueous $NH_4Cl$ (2 mL) was added, and the mixture was extracted with EtOAc (10 mL×3). The combined organic layers were dried over $Na_2SO_4$ and filtered, and the filtrate was concentrated in vacuo. The crude product was purified by preparative HPLC to give the title compound as an oil. LRMS m/z (M+H) 420.3 found, 420.2 required.

Example 25

N-{2-[4-(1-Hydroxy-1-methylethyl)-5-methyl-1,3-oxazol-2-yl]ethyl}-N-(1-methylethyl)-2-(2H-1,2,3-triazol-2-yl)benzamide

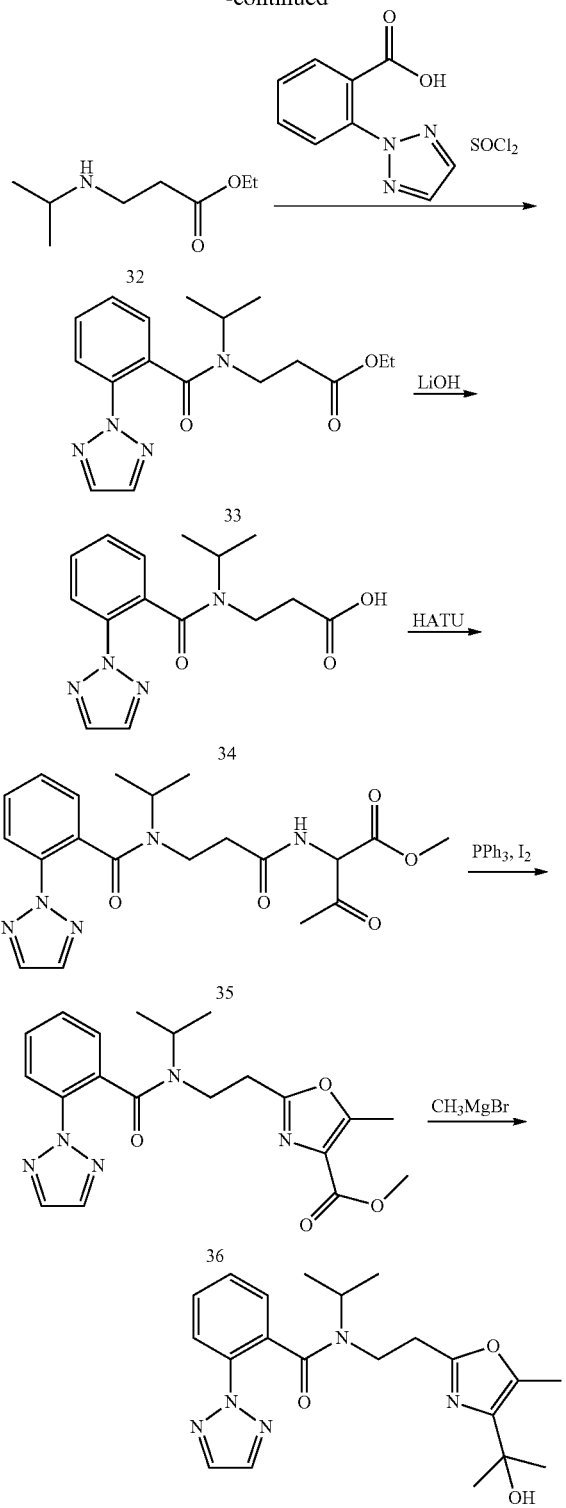

Example 25

Step 1: Ethyl 3-(isopropylamino)propanoate (32)

To a solution of propan-2-amine (8.26 g, 0.14 mol) in EtOH (20 mL) at RT was added ethyl acrylate (10 g, 0.1 mol). The mixture was stirred at RT overnight and concentrated in vacuo to give the title compound as an oil. LRMS m/z (M+H) 160.1 found, 160.2 required.

Step 2: Ethyl 3-(N-isopropyl-2-(2H-1,2,3-triazol-2-yl)benzamido)propanoate (33)

To a solution of 2-(2H-1,2,3-triazol-2-yl)benzoic acid (1.0 g, 5.3 mmol) in dry DCM (10 mL) was added $SOCl_2$ (1 mL) and the mixture was heated at 50° C. for 2 hours. The cooled mixture was concentrated in vacuo. The residue and the product from Step 1 (1.27 g, 8.0 mmol) were dissolved in dry DCM (10 mL) at 0° C. and TEA (2 mL) was added dropwise. The resulting mixture was stirred at RT for 30 mins and concentrated in vacuo to give the title compound as a solid. LRMS m/z (M+H) 331.1 found, 331.2 required.

Step 3: 3-(N-Isopropyl-2-(2H-1,2,3-triazol-2-yl)benzamido)propanoic Acid (34)

To a solution of the product from Step 2 (840 mg, 2.54 mmol) in EtOH/$H_2O$ (10 mL/1 mL) was added LiOH (254 mg, 10.6 mmol). The mixture was stirred at RT for 6 h and extracted with EtOAc (20 mL×3). The pH of the aqueous layer was adjusted to around ~3-4 by addition of 2N HCl and then extracted with EtOAc (10 mL×3). The combined organic layers were dried over $MgSO_4$, filtered, and concentrated in vacuo to give the title compound as an oil. LRMS m/z (M+H) 303.1 found, 303.2 required.

Step 4: Methyl 2-(3-(N-isopropyl-2-(2H-1,2,3-triazol-2-yl)benzamido)propanamido)-3-oxobutanoate (35)

A solution of the product from Step 3 (602 mg, 2.0 mmol), methyl 2-amino-3-oxobutanoate hydrochloride (500 mg, 3.0 mmol), HATU (912 mg, 2.4 mmol), and TEA (0.6 mL) in DCM (15 mL) was stirred at RT overnight. The mixture was filtered and the filtrate was purified by silica gel column chromatography (10-66% EtOAc in petroleum ether) to give the title compound as an oil. LRMS m/z (M+H) 416.1 found, 416.2 required.

Step 5: Methyl 2-(2-(N-isopropyl-2-(2H-1,2,3-triazol-2-yl)benzamido)ethyl)-5-methyloxazole-4-carboxylate (36)

To a solution of $I_2$ (462 mg, 1.82 mmol), $Ph_3P$ (479 mg, 1.82 mmol), and TEA (347 mg, 3.64 mmol) in DCM (15 mL) was added a solution of the product from Step 4 (380 mg, 0.91 mmol) in DCM (10 mL). The resulting mixture was stirred at RT for 3 h, poured into water, and extracted with DCM (100 mL×3). The combined organic layers were washed with brine, dried over $MgSO_4$, filtered, and concentrated in vacuo. The crude product was purified by silica gel column chromatography (10-50% EtOAc in petroleum ether) to give the title compound as an oil. LRMS m/z (M+H) 398.1 found, 398.2 required.

Step 6: N-{2-[4-(1-hydroxy-1-methylethyl)-5-methyl-1,3-oxazol-2-yl]ethyl}-N-(1-methylethyl)-2-(2H-1,2,3-triazol-2-yl)benzamide (Example 25)

To a solution of the product from Step 5 (99.5 mg, 0.25 mmol) in THF (5.0 mL) was added MeMgBr solution (3.0 M, 0.5 mL, 1.5 mmol). The mixture was stirred at RT overnight. Water was added and the mixture was extracted with EtOAc (10 mL×3). The combined organic layers were washed with brine, dried over Na₂SO₄, filtered, and the filtrate was concentrated in vacuo. The residue was purified by preparative HPLC to give the title compound as a solid. LRMS m/z (M+H) 398.2 found, 398.2 required.

Example 27

N-{2-[4-(1-Hydroxy-1-methylethyl)-5-methyl-1,3-oxazol-2-yl]ethyl}-N-(3-hydroxypropyl)-2-(2H-1,2,3-triazol-2-yl)benzamide

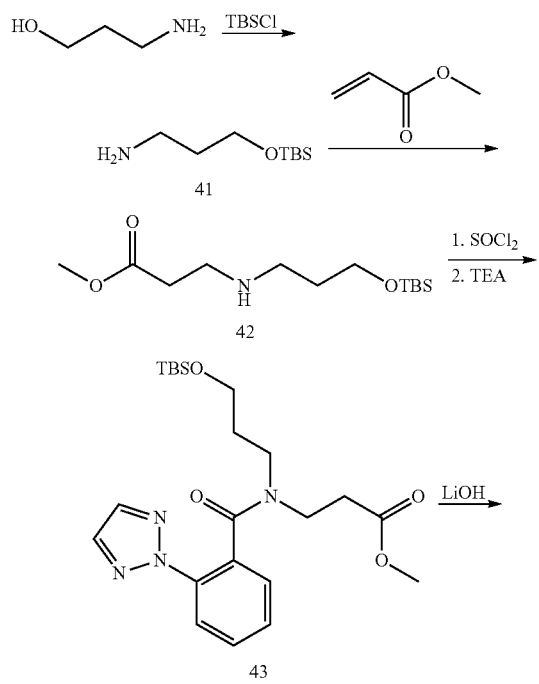

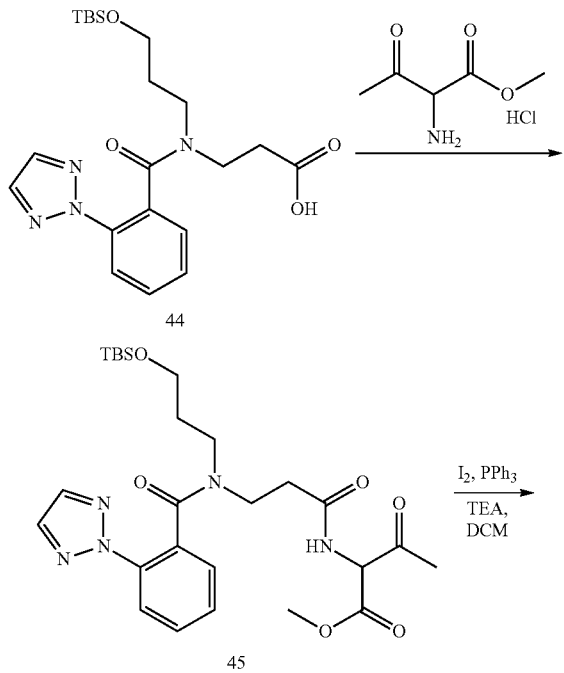

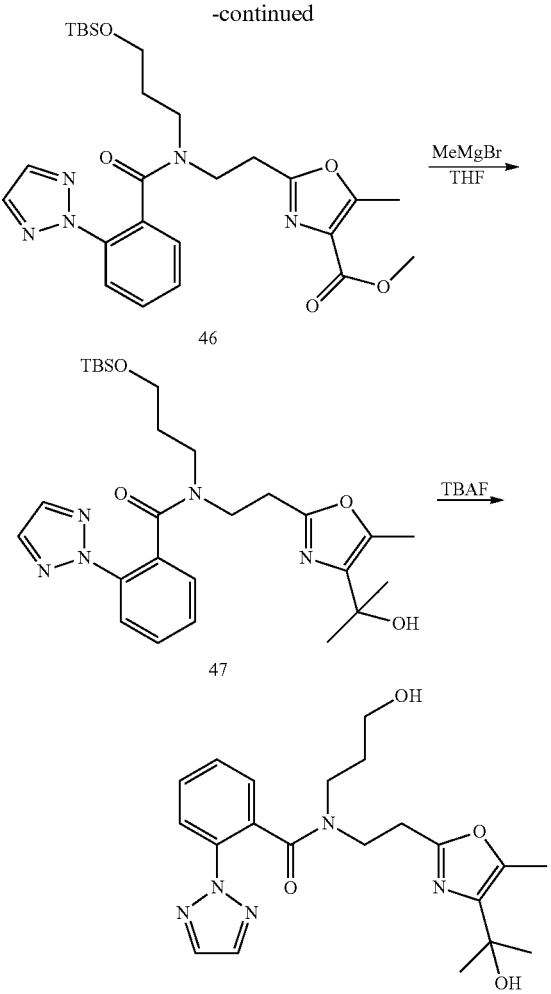

Example 27

Step 1: 3-((tert-Butyldimethylsilyl)oxy)propan-1-amine (41)

To a mixture of 3-aminopropan-1-ol (8.6 g, 0.12 mmol) and imidazole (8.7 mg, 0.13 mmol) in DCM (50 mL) at 0° C. was added TBSCl (17 g, 0.11 mmol). The resulting mixture was stirred at RT overnight, diluted with DCM, washed with water (50 mL×3), dried over Na₂SO₄, and filtered. The filtrate was concentrated in vacuo to give the title product as an oil which was used without further purification. LRMS m/z (M+H) 190.1 found, 190.2 required.

Step 2: Methyl 3-((3-((tert-butyldimethylsilyl)oxy)propyl)amino)propanoate (42)

To a solution of the product from Step 1 (5.4 g, 28.5 mmol) in EtOH (40 mL) was added methyl acrylate (2.8 g, 32.5 mmol) at RT. The resulting mixture was stirred at RT overnight and concentrated in vacuo to give the title compound as an oil. LRMS m/z (M+H) 276.1 found, 276.2 required.

Step 3: Methyl 3-(N-(3-((tert-butyldimethylsilyl)oxy)propyl)-2-(2H-1,2,3-triazol-2 yl)benzamido)propanoate (43)

To a solution of 2-(2H-1,2,3-triazol-2-yl)benzoic acid (0.6 g, 3.2 mmol) in dry DCM (5 mL) was added SOCl₂ (3 mL)

and the mixture was heated at 50° C. for 2 hours. The cooled mixture was concentrated in vacuo. To a solution of methyl 3-((3-(((tert-butyldimethylsilyl)oxy)propyl)amino)propanoate (1.0 g, 3.6 mmol) and TEA (1 mL, 5.94 mmol) in dry DCM (5 mL) at 0° C. was added dropwise a solution of the above residue in DCM (5 mL). The resulting mixture was stirred at RT for 30 mins and concentrated in vacuo. The residue was purified by column silica gel column chromatography (50% EtOAc in petroleum ether) to give the title compound as an oil. LRMS m/z (M+H) 447.1 found, 447.2 required.

Step 4: 3-(N-(3-((tert-Butyldimethylsilyl)oxy)propyl)-2-(2H-1,2,3-triazol-2-yl)benzamido)propanoic Acid (44)

To a solution of the product from Step 3 (200 mg, 0.45 mmol) in MeOH/H$_2$O (4 mL/1 mL) was added LiOH (90 mg, 2.25 mmol). The mixture was stirred at RT for 3 h and extracted with t-BuOMe (20 mL×4). The mixture was adjusted to pH 5-6 with aqueous KHSO$_4$ solution and then extracted with EtOAc (40 mL×3). The combined organic layers were dried over Na$_2$SO$_4$, filtered, and the filtrate concentrated in vacuo to give the title compound as an oil. LRMS m/z (M+H) 433.1 found, 433.2 required.

Step 5: Methyl 8-(2-(2H-1,2,3-triazol-2-yl)benzoyl)-13-acetyl-2,2,3,3-tetramethyl-11-oxo-4-oxa-8,12-diaza-3-silatetradecan-14-oate (45)

To a solution of the product from Step 4 (70 mg, 0.16 mmol) in DCM (4 mL) at 0° C. was added HATU (100 mg, 0.26 mmol) and TEA (57 mg, 0.57 mmol). After the mixture was stirred at RT for 30 mins, methyl 2-amino-3-oxobutanoate hydrochloride (50 mg, 0.3 mmol) was added. The resulting mixture was stirred at RT overnight. Water (10 mL) was added and the solution was extracted with DCM (10 mL×4). The organic layers were combined, washed with brine (10 mL×3), dried over Na$_2$SO$_4$, filtered, and the filtrate concentrated in vacuo to give the title compound as an oil. LRMS m/z (M+H) 546.1 found, 546.2 required.

Step 6: Methyl 2-(2-(N-(3-((tert-butyldimethylsilyl)oxy)propyl)-2-(2H-1,2,3-triazol-2-yl)benzamido)ethyl)-5-methyloxazole-4-carboxylate (46)

To a solution of I$_2$ (135 mg, 0.53 mmol), PPh$_3$ (140 mg, 0.53 mmol), and TEA (108 mg, 1.07 mmol) in DCM (2 mL) at 0° C. was added a solution of the product from Step 5 (140 mg, 0.26 mmol) in DCM (3 mL). The resulting mixture was stirred at RT overnight, concentrated in vacuo, and purified by silica gel column chromatography (33% EtOAc in petroleum ether) to give the title compound as an oil. LRMS m/z (M+H) 528.1 found, 528.2 required.

Step 7: N-(3-(((tert-Butyldimethylsilyl)oxy)propyl)-N-(2-(4-(2-hydroxypropan-2-yl)-5-methyloxazol-2-yl)ethyl)-2-(2H-1,2,3-triazol-2-yl)benzamide (47)

To a solution of MeMgBr (0.150 mL, 0.45 mmol) in dry THF (1 mL) at 0° C. under nitrogen was added dropwise a solution of the product from Step 6 (50 mg, 0.09 mmol) in THF (3 mL). The resulting mixture was stirred at 0° C. for 1 h, then saturated, aqueous NH$_4$Cl was added and the mixture was extracted with EtOAc (10 mL×3). The combined organic layers were dried over Na$_2$SO$_4$, filtered, and the filtrate was concentrated in vacuo to give the title compound as an oil. LRMS m/z (M+H) 528.1 found, 528.2 required.

Step 8: N-{2-[4-(1-Hydroxy-1-methylethyl)-5-methyl-1,3-oxazol-2-yl]ethyl}-N-(3-hydroxypropyl)-2-(2H-1,2,3-triazol-2-yl)benzamide (Example 27)

To a solution of the product from Step 7 (50 mg, 0.09 mol) in THF (4 mL) was added TBAF (100 mg, 0.45 mmol) at RT and the mixture was stirred at RT overnight. Water (5 mL) was added and the mixture was concentrated in vacuo to remove most of the THF. The mixture was extracted with EtOAc (10 mL×3), the combined organic phases were dried over Na$_2$SO$_4$, filtered, and the filtrate was concentrated in vacuo. The residue was purified by preparative HPLC to give the title compound as an oil. LRMS m/z (M+H) 414.1 found, 414.0 required.

Example 28

N-(2-hydroxyethyl)-N-(2-(4-(2-hydroxypropan-2-yl)-5-methyloxazol-2-yl)ethyl)-2-(2H-1,2,3-triazol-2-yl)benzamide

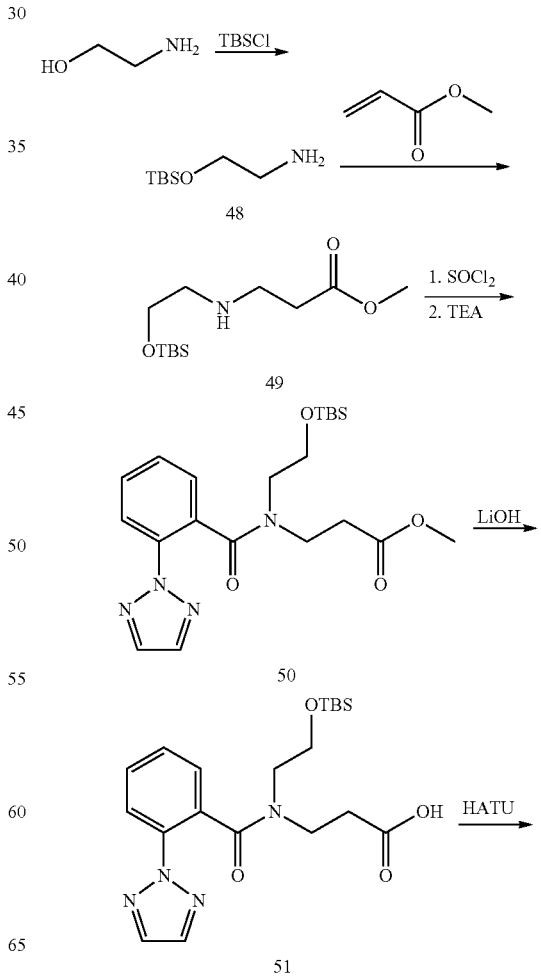

-continued

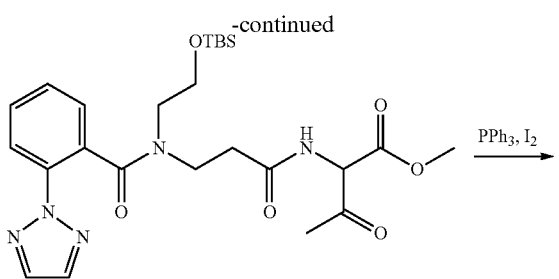

52

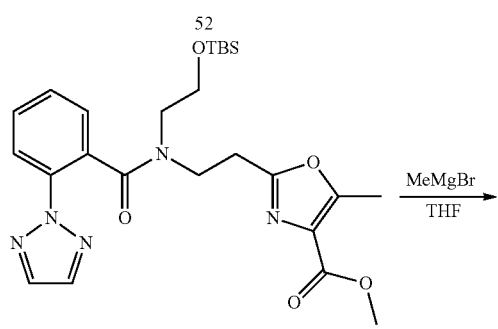

53

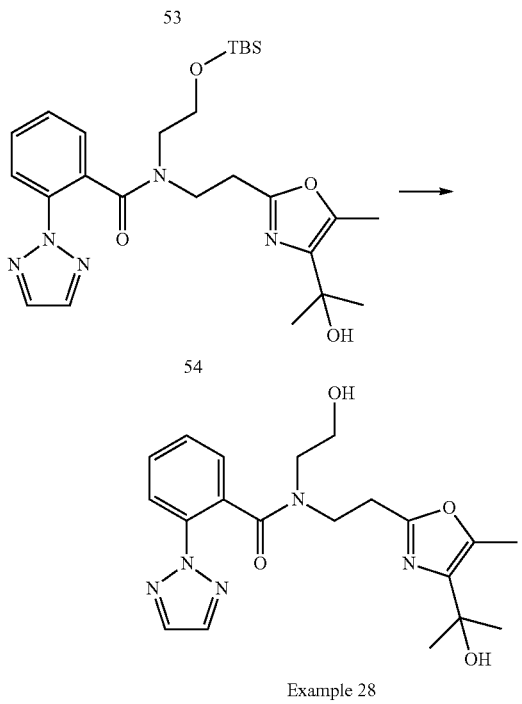

54

Example 28

Step 1: 2-((tert-Butyldimethylsilyl)oxy)ethanamine (48)

To a solution of 2-aminoethanol (12 g, 196 mmol) and imidazole (16.1 g, 236 mmol) in DCM (100 mL) was added TBSCl (32.6 g, 216 mmol) in DCM (50 mL) dropwise at 0° C. The resulting mixture was stirred at RT overnight, washed with water (50 mL×3), dried over Na$_2$SO$_4$, filtered, and the filtrate was concentrated in vacuo to give the title compound as an oil. LRMS m/z (M+H) 176.1 found, 176.2 required.

Step 2: Methyl 3-((2-((tert-butyldimethylsilyl)oxy)ethyl)amino)propanoate (49)

To a solution of methyl acrylate (4.9 g, 57.0 mmol) in ethanol (100 mL) was added the product from Step 1 (10 g, 57.0 mmol) at RT. The resulting mixture was stirred at RT overnight and concentrated in vacuo to give the title compound as an oil which was used without further purification. LRMS m/z (M+H) 262.1 found, 262.1 required.

Step 3: Methyl 3-(N-(2-((tert-butyldimethylsilyl)oxy)ethyl)-2-(2H-1,2,3-triazol-2 yl)benzamido)propanoate (50)

To a solution of 2-(2H-1,2,3-triazol-2-yl)benzoic acid (0.72 g, 3.8 mmol) in dry DCM (3 mL) was added SOCl$_2$ (1.34 g, 11.4 mmol) and the mixture was heated at 50° C. for 2 h. After cooling to RT, the mixture was concentrated in vacuo and dissolved in DCM (5 mL) to form solution A. To a solution of the product from Step 2 (1.0 g, 3.8 mmol) and TEA (0.77 g, 7.6 mmol) in dry DCM (5 mL) at 0° C. was added solution A dropwise. The resulting mixture was stirred at RT for 30 mins, concentrated in vacuo, and the residue was purified by silica gel column chromatography (50% EtOAc in petroleum ether) to give the title compound as an oil. LRMS m/z (M+H) 433.1 found, 433.2 required.

Step 4: 3-(N-(2-((tert-Butyldimethylsilyl)oxy)ethyl)-2-(2H-1,2,3-triazol-2-yl)benzamido)propanoic Acid (51)

To a solution of the product from Step 3 (700 mg, 1.6 mmol) in MeOH/H$_2$O (8 mL/2 mL) was added LiOH monohydrate (320 mg, 7.6 mmol). The resulting mixture was stirred at RT for 3 h and concentrated in vacuo. The residue was diluted with water (10 mL), the pH was adjusted to ~5-6 by addition of aqueous KHSO$_4$ solution, and the mixture was extracted with EtOAc (15 mL×5). The combined organic layers were dried over Na$_2$SO$_4$, filtered, and the filtrate was concentrated in vacuo to give the title compound as an oil. LRMS m/z (M+H) 419.1 found, 419.2 required.

Step 5: Methyl 7-(2-(2H-1,2,3-triazol-2-yl)benzoyl)-12-acetyl-2,2,3,3-tetramethyl-10-oxo-4-oxa-7,11-diaza-3-silatridecan-13-oate (52)

To a solution of the product from Step 4 (230 mg, 0.55 mmol) in DCM (4 mL) at 0° C. was added HATU (100 mg, 0.26 mmol) and TEA (57 mg, 0.57 mmol). The mixture was stirred at RT for 30 mins and a solution of methyl 2-amino-3-oxobutanoate hydrochloride (130 mg, 0.78 mmol) in DCM was added. The resulting mixture was stirred at RT overnight, water (10 mL) was added, and the mixture was extracted with DCM (10 mL×5). The organic layers were combined, washed with brine (20 mL×3), dried over Na$_2$SO$_4$, filtered, and the filtrate was concentrated in vacuo to give the title compound as an oil. LRMS m/z (M+H) 532.1 found, 532.2 required.

Step 6: Methyl 2-(2-(N-(2-((tert-butyldimethylsilyl)oxy)ethyl)-2-(2H-1,2,3-triazol-2-yl)benzamido)ethyl)-5-methyloxazole-4-carboxylate (53)

To a solution of I$_2$ (425 mg, 1.7 mmol), PPh$_3$ (440 mg, 1.7 mmol), and TEA (340 mg, 3.4 mmol) in DCM (5 mL) at 0° C. was added a solution of the product from Step 5 (440 mg, 0.8 mmol) in DCM (5 mL). The resulting mixture was stirred at RT overnight and then concentrated in vacuo. The residue was purified by silica gel column chromatography (50% EtOAc in petroleum ether) to give the title compound as an oil. LRMS m/z (M+H) 514.1 found, 514.2 required.

Step 7: N-(2-((tert-Butyldimethylsilyl)oxy)ethyl)-N-(2-(4-(2-hydroxypropan-2-yl)-5-methyloxazol-2-yl)ethyl)-2-(2H-1,2,3-triazol-2-yl)benzamide (54)

To a solution of MeMgBr (3.0 M, 1.0 mL, 3 mmol) in dry THF (1 mL) at −78° C. under nitrogen was added dropwise a solution of the product from Step 6 (40 mg, 0.08 mmol) in THF (2 mL). The resulting mixture was stirred at 0° C. for 1 h. Saturated, aqueous $NH_4Cl$ was added and the mixture was extracted with EtOAc (10 mL×5). The combined organic layers were dried over $Na_2SO_4$, filtered, and the filtrate was concentrated in vacuo to give the title compound as an oil. LRMS m/z (M+H) 514.1 found, 514.2 required.

Step 8: N-(2-((tert-Butyldimethylsilyl)oxy)ethyl)-N-(2-(4-(2-hydroxypropan-2-yl)-5-methyloxazol-2-yl)ethyl)-2-(2H-1,2,3-triazol-2-yl)benzamide (example 28)

To a solution of the product from Step 7 (20 mg, 0.04 mol) in DCM (2 mL) at RT was added $Et_3N.3HF$ (0.5 mL). The mixture was stirred at RT for 5 h, then saturated, aqueous $NaHCO_3$ was added and the mixture was extracted with DCM (5 mL×4). The combined organic layers were dried over $Na_2SO_4$, filtered, and the filtrate was concentrated in vacuo. The residue was purified by preparative HPLC to give the title compound as an oil. LRMS m/z (M+H) 400.2 found, 400.2 required.

Example 29

N-(2-(4-(2-Hydroxypropan-2-yl)-5-methyloxazol-2-yl)ethyl)-N-(2-methoxyethyl)-2-(2H-1,2,3-triazol-2-yl)benzamide

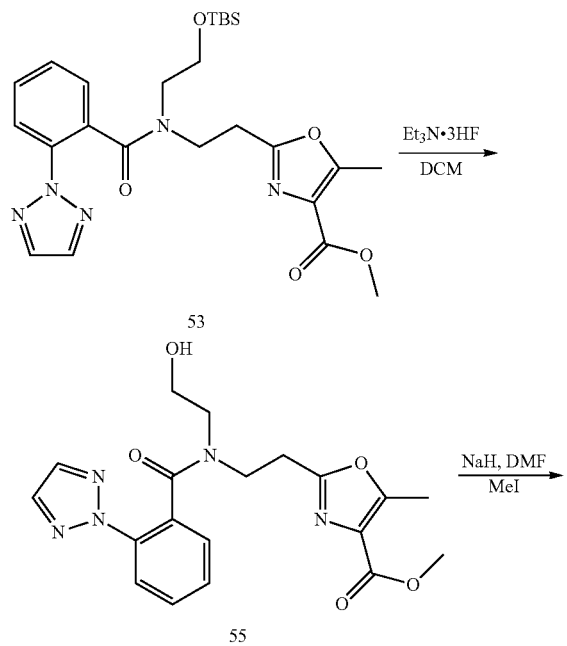

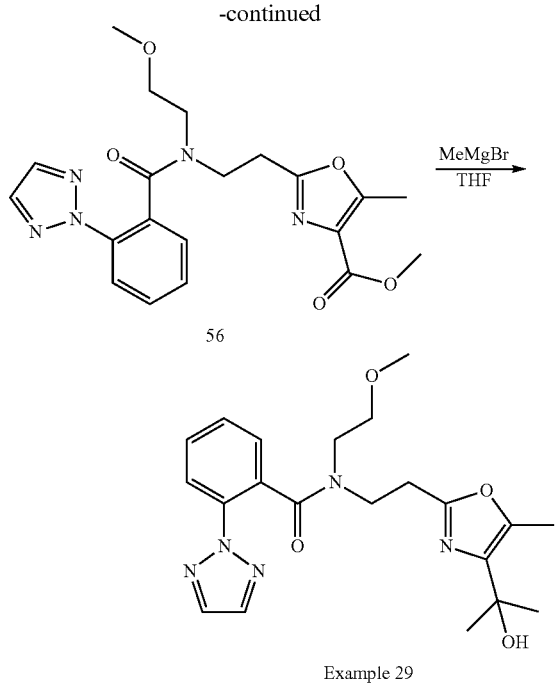

Example 29

Step 1: Methyl 2-(2-(N-(2-hydroxyethyl)-2-(2H-1,2,3-triazol-2-yl)benzamido)ethyl)-5-methyloxazole-4-carboxylate (55)

To a solution of compound 53 (Example 28, Step 7) (60 mg, 0.1 mmol) in DCM (2 mL) at RT was added $Et_3N.3HF$ (0.5 mL). The mixture was stirred at RT for 5 h, then saturated, aqueous $NaHCO_3$ was added and the mixture was extracted with DCM (5 mL×4). The combined organic layers were dried over $Na_2SO_4$, filtered, and the filtrate was concentrated in vacuo to give the title compound as an oil. LRMS m/z (M+H) 400.1 found, 400.2 required.

Step 2: Methyl 2-(2-(N-(2-methoxyethyl)-2-(2H-1,2,3-triazol-2-yl)benzamido)ethyl)-5-methyloxazole-4-carboxylate (56)

To a solution of the product from Step 1 (80 mg, 0.2 mmol) in DMF (2 mL) was added NaH (60 wt % in mineral oil, 25 mg, 0.63 mmol). The reaction mixture was stirred at RT for 20 mins, then MeI (150 mg, 0.63 mmol) was added and the resulting mixture was stirred at RT overnight. Water (10 mL) was added and the mixture was extracted with EtOAc (10 mL×4). The combined organic layers were washed with brine, dried over $Na_2SO_4$, filtered, and concentrated in vacuo. The residue was purified by preparative TLC (50% EtOAc in petroleum ether) to give the title compound as an oil. LRMS m/z (M+H) 414.1 found, 414.2 required.

Step 3: N-(2-(4-(2-hydroxypropan-2-yl)-5-methyl-oxazol-2-yl)ethyl)-N-(2-methoxyethyl)-2-(2H-1,2,3-triazol-2-yl)benzamide (Example 29)

To a solution of MeMgBr (1.0 mL, 3 mmol) in dry THF (1 mL) at −78° C. under nitrogen was added a solution of the product from Step 2 (60 mg, 0.15 mmol) in THF (2 mL) dropwise. The resulting mixture was stirred at 0° C. for 1 h, then quenched with saturated, aqueous NH₄Cl and extracted with EtOAc (10 mL×5). The combined organic layers were dried over anhydrous Na₂SO₄ and filtered, and the filtrate was concentrated in vacuo. The residue was purified by preparative HPLC to give the title compound as an oil. LRMS m/z (M+H) 414.2 found, 414.2 required.

Example 30

N-(2-(4-(2-Hydroxypropan-2-yl)-5-methyloxazol-2-yl)ethyl)-N-methyl-2-(2H-1,2,3-triazol-2-yl)benzamide

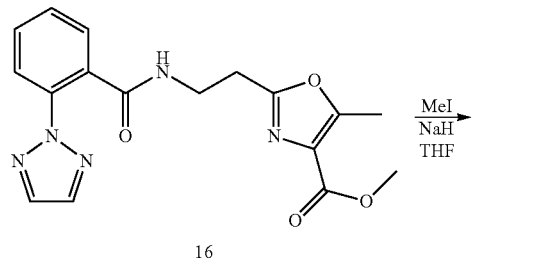

16

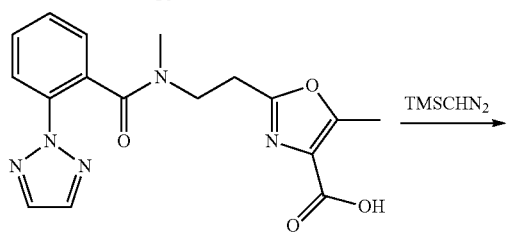

57

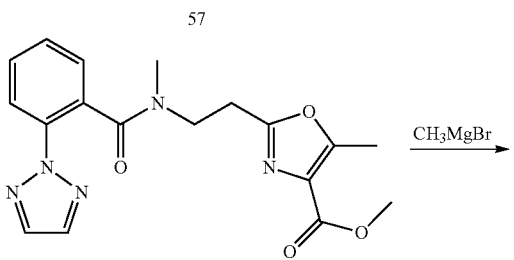

58

Example 30

Step 1: 5-Methyl-2-(2-(N-methyl-2-(2H-1,2,3-triazol-2-yl)benzamido)ethyl)oxazole-4-carboxylic Acid (57)

To a solution of methyl 2-(2-(2-(2H-1,2,3-triazol-2-yl)benzamido)ethyl)-5-methyloxazole-4-carboxylate (compound 16, Example 21, Step 4) (200 mg, 0.56 mmol) in THF (5 mL) was added NaH (60 wt % in oil, 24 mg, 0.85 mmol). The mixture was stirred at RT for 20 mins, then MeI (160 mg, 1.12 mmol) was added. The resulting mixture was stirred at RT overnight and then quenched with 10 mL of water and extracted with EtOAc (10 mL×2). The aqueous layer was adjusted to pH ~4 with 4 N HCl, then extracted with EtOAc (10 mL×3). The combined organic layers were dried over MgSO₄, filtered, and concentrated in vacuo to give the title compound as an oil. LRMS m/z (M+H) 356.1 found, 356.2 required.

Step 2: Methyl 5-methyl-2-(2-(N-methyl-2-(2H-1,2,3-triazol-2-yl)benzamido)ethyl)oxazole-4-carboxylate (58)

To a solution of the product from Step 1 (110 mg, 0.31 mmol) in DCM/MeOH (10.0 mL/1.0 mL) at 0° C. was added dropwise TMSCHN₂ (0.25 mL, 0.5 mmol). The resulting mixture was stirred at 0° C. for 20 mins, then was quenched with saturated, aqueous NH₄Cl and extracted with DCM (5 mL×3). The combined organic layers were dried over Na₂SO₄, filtered, and concentrated in vacuo to give the title compound as an oil. LRMS m/z (M+H) 370.1 found, 370.2 required.

Step 3: N-(2-(4-(2-Hydroxypropan-2-yl)-5-methyloxazol-2-yl)ethyl)-N-methyl-2-(2H-1,2,3-triazol-2-yl)benzamide (Example 30)

To a solution of the product from Step 2 (80 mg, 0.22 mmol) in THF (5 mL) at 0° C. was added MeMgBr solution (3 M in ether, 0.4 mL, 1.2 mmol). The resulting mixture was stirred at 0° C. for 2 h, quenched with MeOH, and purified by preparative HPLC to give the title compound as a solid. LRMS m/z (M+H) 370.2 found, 370.2 required.

Example 31

N-Cyclopropyl-N-(2-(4-(2-hydroxypropan-2-yl)-5-methyloxazol-2-yl)ethyl)-2-(2H-1,2,3-triazol-2-yl)benzamide

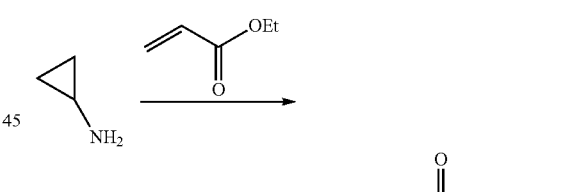

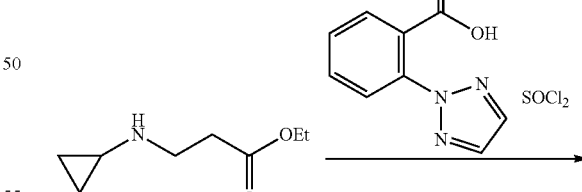

59

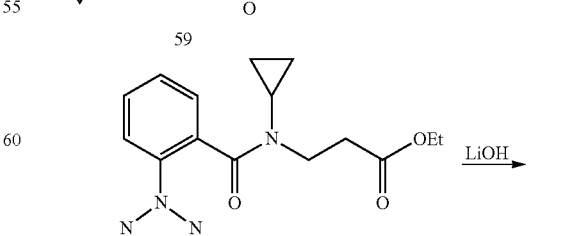

60

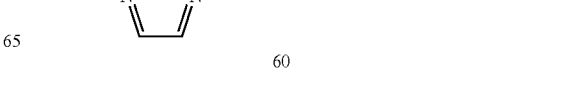

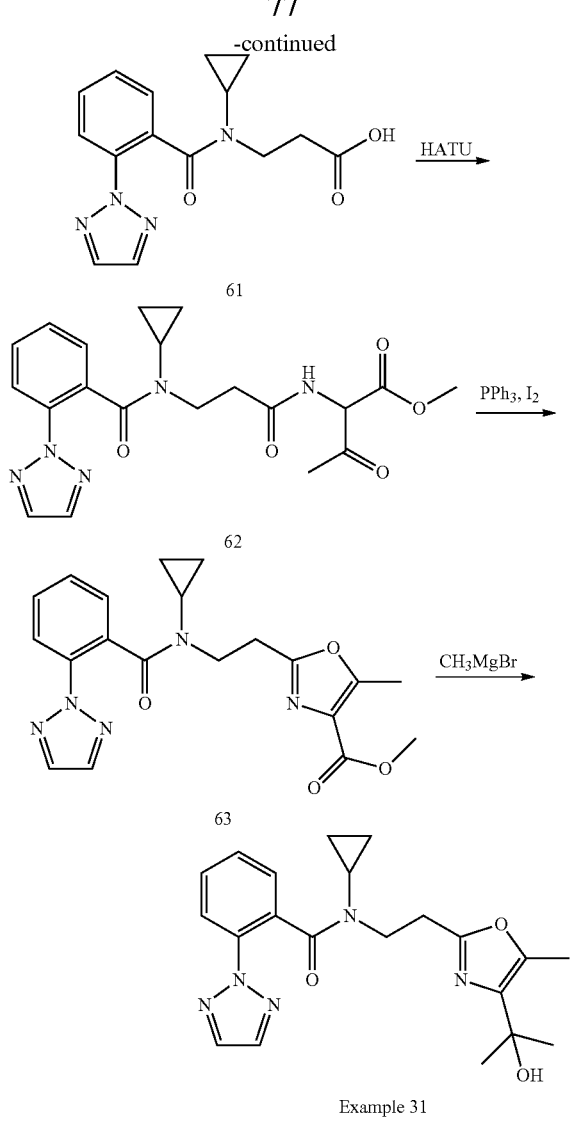

Example 31

Step 1: Ethyl 3-(cyclopropylamino)propanoate (59)

A solution of cyclopropanamine (8.0 g, 0.14 mol) and ethyl acrylate (10 g, 0.1 mol) in EtOH (20 mL) was stirred at RT overnight. The mixture was concentrated in vacuo to give the title compound as an oil, which was used for the next step without further purification. LRMS m/z (M+H) 158.2 found, 158.2 required.

Step 2: Ethyl 3-(N-cyclopropyl-2-(2H-1,2,3-triazol-2-yl)benzamido)propanoate (60)

To a solution of 2-(2H-1,2,3-triazol-2-yl)benzoic acid (1.0 g, 5.3 mmol) in DCM (10 mL) was added $SOCl_2$ (2 mL). The resulting mixture was stirred at 50° C. for 2 h. After cooling to RT, the mixture was concentrated in vacuo to remove the solvent. To a solution of the product from Step 1 (1.24 g, 8.0 mmol) and TEA (2.0 mL, 15.7 mmmol) in DCM (10 mL) at 0° C. was added a solution of the above residue in DCM (10 mL) dropwise. The resulting mixture was stirred at ° C. for 30 mins, then quenched with water (20 mL) and extracted with DCM (15 mL×3). The combined organic layers were washed with 0.5 N HCl, dried over $Na_2SO_4$, and concentrated in vacuo to give the title compound as an oil. LRMS m/z (M+H) 329.2 found, 329.2 required.

Step 3: 3-(N-Cyclopropyl-2-(2H-1,2,3-triazol-2-yl)benzamido)propanoic Acid (61)

To a solution of the product from Step 2 (2.0 g, 5.3 mmol) in EtOH (20 mL) was added LiOH (509 mg, 21.2 mmol) and water (2 mL). The resulting mixture was stirred at RT overnight, then concentrated in vacuo to remove most of the EtOH. The residue was diluted with water (10 mL) and extracted with EtOAc. The aqueous layer was adjusted to pH~2 with 2 N HCl and then extracted with DCM. The combined organic layers were dried over $MgSO_4$, filtered, and concentrated in vacuo to give the crude product as a solid, which was used without further purification. LRMS m/z (M+H) 301.0 found, 301.2 required.

Step 4: Methyl 2-(3-(N-cyclopropyl-2-(2H-1,2,3-triazol-2-yl)benzamido)propanamido)-3-oxobutanoate (62)

To a solution of the product from Step 3 (600 mg, 2.0 mmol) and methyl 2-amino-3-oxobutanoate hydrochloride (500 mg, 3.0 mmol) in DCM (12 mL) was added HATU (912 mg, 2.4 mmol) at RT. The resulting mixture was stirred at RT for 20 mins, then TEA (0.6 mL) was added slowly. The mixture was stirred at RT for 2 h. The mixture was concentrated in vacuo and the residue was purified by preparative TLC (67% EtOAc in petroleum ether) to give the title compound as an oil. LRMS m/z (M+H) 414.2 found, 414.2 required.

Step 5: Methyl 2-(2-(N-cyclopropyl-2-(2H-1,2,3-triazol-2-yl)benzamido)ethyl)-5-methyloxazole-4-carboxylate (63)

To a solution of $I_2$ (712 mg, 2.8 mmol), $PPh_3$ (734 mg, 2.8 mmol), and TEA (566 mg, 5.6 mmol) in DCM (15 mL) was added a solution of the product from Step 4 (580 mg, 1.4 mmol) in DCM (7 mL). The resulting mixture was stirred at RT for 1 h, then washed with aq. $Na_2SO_3$, dried over $Na_2SO_4$, filtered, and concentrated in vacuo. The residue was purified by preparative TLC (67% EtOAc in petroleum ether) to give the title compound as an oil. LRMS m/z (M+H) 396.1 found, 396.2 required.

Step 6: N-Cyclopropyl-N-(2-(4-(2-hydroxypropan-2-yl)-5-methyloxazol-2-yl)ethyl)-2-(2H-1,2,3-triazol-2-yl)benzamide (Example 31)

To a solution of the product from Step 5 (100 mg, 0.25 mmol) in THF (5.0 mL) was added MeMgBr solution (3 M in ether, 0.4 mL, 1.2 mmol) at 0° C. The resulting mixture was stirred at 0° C. for 1 h, then quenched with saturated, aqueous $NH_4Cl$ and extracted with EtOAc (5.0 mL×3). The combined organic layers were washed with brine, dried over $Na_2SO_4$, filtered, and concentrated in vacuo. The residue was purified by preparative HPLC to give the title compound as a solid. LRMS m/z (M+H) 396.2 found, 396.2 required.

Example 32

N-Cyclobutyl-N-(2-(4-(2-hydroxypropan-2-yl)-5-methyloxazol-2-yl)ethyl)-2-(2H-1,2,3-triazol-2-yl)benzamide

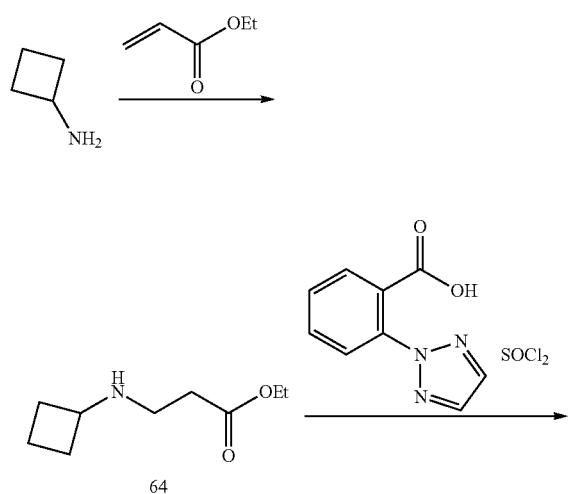

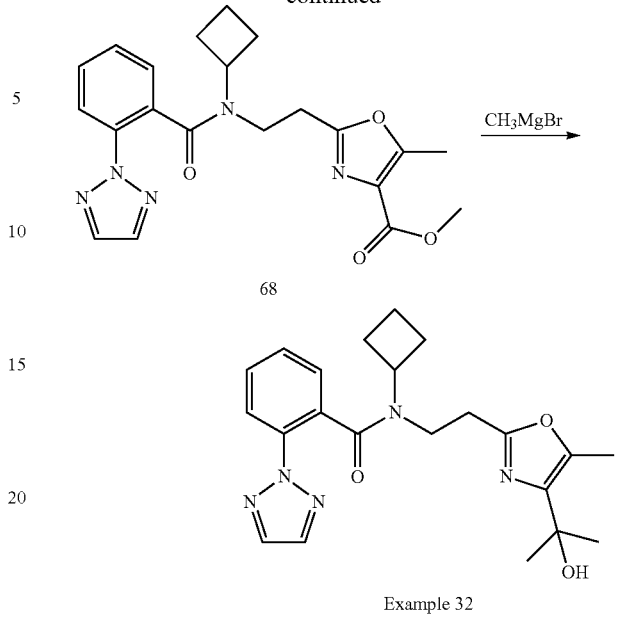

Example 32

Step 1: Ethyl 3-(cyclobutylamino)propanoate (64)

To a solution of cyclobutanamine (3.0 g, 42.2 mmol) in EtOH (10 mL) at RT was added ethyl acrylate (3.5 g, 35 mmol). The mixture was stirred at RT overnight and then concentrated in vacuo to give the title compound as an oil. LRMS m/z (M+H) 172.1 found, 172.2 required.

Step 2: Ethyl 3-(N-cyclobutyl-2-(2H-1,2,3-triazol-2-yl)benzamido)propanoate (65)

To a solution of 2-(2H-1,2,3-triazol-2-yl)benzoic acid (0.5 g, 2.65 mmol) in dry DCM (5 mL) was added $SOCl_2$ (1.0 mL). The resulting mixture was stirred at 50° C. for 2 hours. After cooling to RT, the mixture was concentrated in vacuo. To a solution of the product from Step 1 (678 mg, 3.9 mmol) and TEA (1.0 mL, 7.85 mmol) in DCM (10 mL) at 0° C. was added a solution of the above residue dropwise. The resulting mixture was stirred at 0° C. for 20 mins, then quenched with water (10 mL) and extracted with DCM (10 mL×3). The combined organic layers were dried over $Na_2SO_4$, filtered, and concentrated in vacuo to give the title compound as an oil. LRMS m/z (M+H) 343.2 found, 343.2 required.

Step 3: 3-(N-cyclobutyl-2-(2H-1,2,3-triazol-2-yl)benzamido)propanoic Acid (66)

To a solution of the product from step 2 (1.4 g, 4.09 mmol) in $EtOH/H_2O$ (10 mL/1 mL) was added LiOH (491 mg, 20.5 mmol). The mixture was stirred at RT overnight, then concentrated in vacuo. The residue was diluted with water (15 mL) and washed with EtOAc (10 mL×3). The aqueous layer was adjusted to pH~2 with conc. HCl, and then extracted with EtOAc (15 mL×3). The combined organic layers were dried over $Na_2SO_4$, filtered, and concentrated in vacuo to give the title compound as an oil. LRMS m/z (M+H) 315.2 found, 315.2 required.

Step 4: Methyl 2-(3-(N-cyclobutyl-2-(2H-1,2,3-triazol-2-yl)benzamido)propanamido)-3-oxobutanoate (67)

To a solution of the product from Step 3 (400 mg, 1.27 mmol) and methyl 2-amino-3-oxobutanoate hydrochloride (318 mg, 1.9 mmol) in DCM (10 mL) was added HATU (580 mg, 1.5 mmol) at RT. The resulting mixture was stirred at RT for 20 mins and then TEA (0.5 mL) was added slowly. The mixture was stirred at RT overnight and then concentrated in vacuo. The residue was purified by preparative TLC (50% EtOAc in petroleum ether) to give the title compound as an oil. LRMS m/z (M+H) 428.2 found, 428.2 required.

Step 5: Methyl 2-(2-(N-cyclobutyl-2-(2H-1,2,3-triazol-2-yl)benzamido)ethyl)-5-methyloxazole-4-carboxylate (68)

To a solution of I₂ (610 mg, 2.4 mmol) and PPh₃ (629 mg, 2.4 mmol) in DCM (10 mL) was added TEA (485 mg, 4.8 mmol) and a solution of the product from Step 4 (380 mg, 1.2 mmol) in DCM (5 mL) at RT. The resulting mixture was stirred at RT for 2 h. The mixture was washed with aqueous Na₂SO₃, dried over Na₂SO₄, filtered, and concentrated in vacuo. The residue was purified by preparative TLC (50% EtOAc in petroleum ether) to give the title compound as an oil. LRMS m/z (M+H) 410.2 found, 410.2 required.

Step 6: N-Cyclobutyl-N-(2-(4-(2-hydroxypropan-2-yl)-5-methyloxazol-2-yl)ethyl)-2-(2H-1,2,3-triazol-2-yl)benzamide (Example 32)

To a solution of the product from Step 5 (220 mg, 0.54 mmol) in THF (15.0 mL) was added MeMgBr (3 M in ether, 1 mL, 3 mmol) dropwise at 0° C. The mixture was warmed to RT for 2 h; the mixture was quenched with saturated, aqueous NH₄Cl solution and extracted with EtOAc (15.0 mL×3). The combined organic layers were washed with brine, dried over Na₂SO₄, filtered, and concentrated in vacuo. The residue was purified by preparative HPLC to give the title compound as a solid. LRMS m/z (M+H) 410.2 found, 410.2 required.

Example 33

N-(2-(4-(2-Hydroxypropan-2-yl)-5-methyloxazol-2-yl)ethyl)-N-(3-methoxypropyl)-2-(2H-1,2,3-triazol-2-yl)benzamide

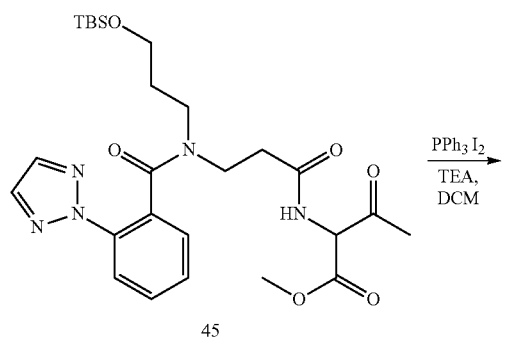

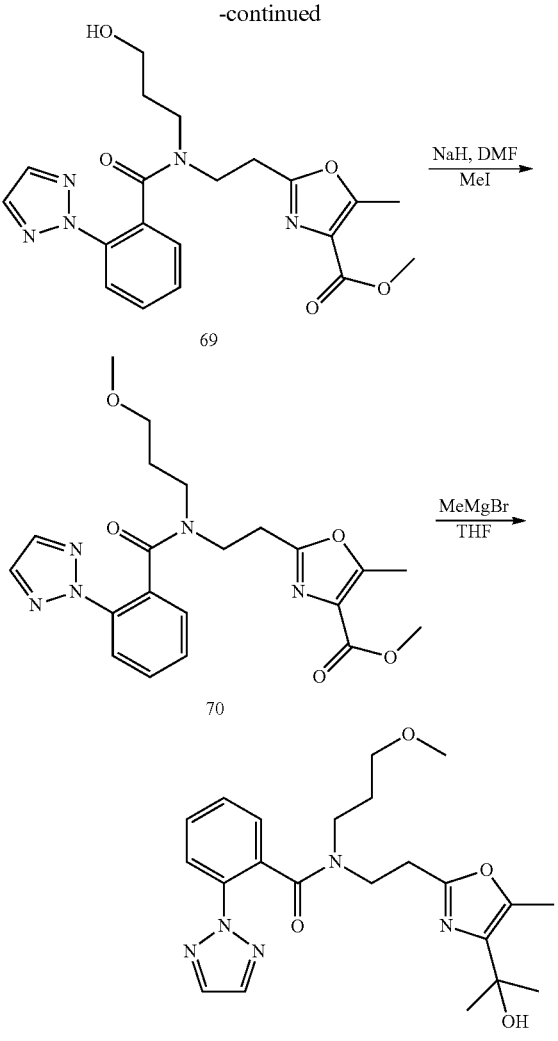

Example 33

Step 1: Methyl 2-(2-(N-(3-hydroxypropyl)-2-(2H-1,2,3-triazol-2-yl)benzamido)ethyl)-5-methyloxazole-4-carboxylate (69)

To a solution of I₂ (473 mg, 1.87 mmol), PPh₃ (490 mg, 1.87 mmol), and TEA (378 mg, 3.7 mmol) in DCM (4 mL) was added a solution of methyl 8-(2-(2H-1,2,3-triazol-2-yl)benzoyl)-13-acetyl-2,2,3,3-tetramethyl-11-oxo-4-oxa-8,12-diaza-3-silatetradecan-14-oate (Compound 45, Example 27, Step 5) (490 mg, 0.9 mmol) in DCM (6 mL) at 0° C. The resulting mixture was stirred at RT overnight and then concentrated in vacuo. The residue was purified by preparative TLC (50% EtOAc in petroleum ether) to give the title compound as an oil. LRMS m/z (M+H) 414.2 found, 414.2 required.

Step 2: Methyl 2-(2-(N-(3-methoxypropyl)-2-(2H-1,2,3-triazol-2-yl)benzamido)ethyl)-5-methyloxazole-4-carboxylate (70)

To a solution of the product from Step 1 (90 mg, 0.22 mmol) in DMF (2 mL) was added NaH (60 wt % in oil, 20 mg, 0.50 mmol). After the mixture was stirred at RT for 20 mins, MeI (61 mg, 0.44 mmol) was added. The resulting mixture was stirred at RT overnight, then was quenched with water (10 mL) and extracted with EtOAc (10 mL×4). The combined organic layers were washed with brine, dried over Na$_2$SO$_4$, filtered, and concentrated in vacuo. The residue was purified by preparative TLC (50% EtOAc in petroleum ether) to give the title compound as an oil. LRMS m/z (M+H) 428.2 found, 428.2 required.

Step 3: N-(2-(4-(2-Hydroxypropan-2-yl)-5-methyl-oxazol-2-yl)ethyl)-N-(3-methoxypropyl)-2-(2H-1,2,3-triazol-2-yl)benzamide (Example 33)

To a solution of MeMgBr solution (3 M in ether, 0.5 mL, 1.5 mmol) in dry THF (1 mL) at 0° C. under nitrogen atmosphere was added a solution of the product from Step 2 (40 mg, 0.09 mmol) in THF (2 mL) dropwise. The resulting mixture was stirred at 0° C. for 1 h, then quenched with saturated, aqueous NH$_4$Cl and extracted with EtOAc (5 mL×5). The combined organic layer was dried over anhydrous Na$_2$SO$_4$, filtered, and concentrated in vacuo. The residue was purified by preparative HPLC to give the title compound as an oil. LRMS m/z (M+H) 428.1 found, 428.2 required.

The following table shows representative data for the compounds of the Examples as orexin receptor antagonists as determined by the assays described herein.

| Example | hOX2R FLIPR IC$_{50}$ (nM) | hOX1R FLIPR IC$_{50}$ (nM) |
|---|---|---|
| 1 | 29 | 1827 |
| 2 | 54 | >10,000 |
| 3 | 44 | >10,000 |
| 4 | 48 | >10,000 |
| 5 | 387 | >10,000 |
| 6 | 101 | >10,000 |
| 7 | 62 | >10,000 |
| 8 | 82 | >10,000 |
| 9 | 491 | >10,000 |
| 10 | 224 | >10,000 |
| 10b | 26 | 1761 |
| 10c | 212 | >10,000 |
| 10d | 435 | >10,000 |
| 11 | 27 | 2590 |
| 12 | 63 | >10,000 |
| 13 | 98 | >10,000 |
| 14 | 211 | >10,000 |
| 15 | 223 | >10,000 |
| 16 | 630 | >10,000 |
| 17 | 292 | >10,000 |
| 18b | 145 | >10,000 |
| 19 | 12 | 3382 |
| 20 | 19 | 2670 |
| 21 | 19 | 1009 |
| 22 | 19 | 2373 |
| 23 | 21 | 2836 |
| 24 | 68 | >10,000 |
| 25 | 152 | >10,000 |
| 27 | 304 | >10,000 |
| 28 | 98 | >10,000 |
| 29 | 19 | >10,000 |
| 30 | 390 | >10,000 |
| 31 | 42 | 7586 |
| 32 | 38 | 8183 |
| 33 | 119 | >10,000 |

The invention claimed is:
1. A compound of formula I:

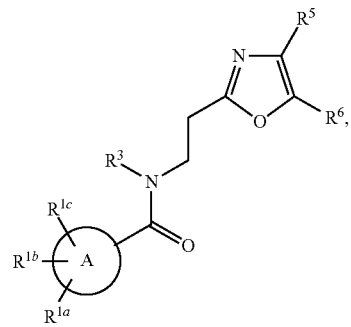

or a pharmaceutically acceptable salt thereof, wherein
A is phenyl, pyridyl, or thiophenyl;
$R^{1a}$, $R^{1b}$, and $R^{1c}$ are independently selected from the group consisting of:
(1) hydrogen,
(2) halogen,
(3) hydroxy,
(4) —(C=O)$_m$O$_n$C$_{1-6}$alkyl, where m is 0 or 1, n is 0 or 1, with the proviso that if m is 0 or n is 0, a bond is present, and where alkyl is unsubstituted or substituted with 1-5 substituents independently selected from $R^4$,
(5) —(C=O)$_m$O$_n$C$_{3-6}$cycloalkyl, where cycloalkyl is unsubstituted or substituted with 1-5 substituents independently selected from $R^4$,
(6) —(C=O)$_m$C$_{2-4}$alkenyl, where alkenyl is unsubstituted or substituted with 1-5 substituents independently selected from $R^4$,
(7) —(C=O)$_m$C$_{2-4}$alkynyl, where alkynyl is unsubstituted or substituted with 1-5 substituents independently selected from $R^4$,
(8) —(C=O)$_m$O$_n$-phenyl or —(C=O)$_m$—O$_n$-naphthyl, where phenyl or naphthyl is unsubstituted or substituted with 1-5 substituents independently selected from $R^4$,
(9) —(C=O)$_m$O$_n$-heterocycle, where the heterocycle is unsubstituted or substituted with 1-5 substituents independently selected from $R^4$,
(10) —(C=O)$_m$NR$^{10}$R$^{11}$,
(11) —S(O)$_2$NR$^{10}$R$^{11}$,
(12) —S(O)$_q$R$^{12}$, where q is 0, 1 or 2 and where R$^{12}$ is selected from the definitions of R$^{10}$ and R$^{11}$,
(13) —CO$_2$H,
(14) —CN, and
(15) —NO$_2$;
$R^3$ is selected from C$_{1-6}$alkyl, C$_{2-6}$alkenyl, or C$_{3-6}$cycloalkyl, wherein $R^3$ is unsubstituted or substituted with 1-5 substituents independently selected from $R^4$;
each $R^4$ is independently selected from the group consisting of:
(1) hydroxyl,
(2) halogen,
(3) C$_{1-6}$alkyl, optionally substituted with 1-5 halogens,
(4) —C$_{3-6}$cycloalkyl,
(5) —O—C$_{1-6}$alkyl, optionally substituted with 1-5 halogens,
(6) —O(C=O)—C$_{1-6}$alkyl,
(7) —NH$_2$,
(8) —NH—C$_{1-6}$alkyl,
(9) —NO$_2$,
(10) phenyl,

(11) heterocycle,
(12) —$CO_2H$, and
(13) —CN;
$R^5$ is $C_{1-6}$alkyl or —$OC_{1-3}$alkyl, wherein $R^5$ is optionally substituted with 1-4 substituent groups which are independently selected from halogen, —OH, and —$OCH_3$;
$R^6$ is $C_{1-3}$alkyl, which is optionally substituted with 1-3 substituent groups which are independently selected from halogen, —OH, and —$OCH_3$; and
$R^{10}$ and $R^{11}$ are independently selected from the group consisting of:
(1) hydrogen,
(2) $C_{1-6}$alkyl, which is unsubstituted or substituted with 1-4 groups independently selected from $R^4$,
(3) $C_{3-6}$alkenyl, which is unsubstituted or substituted with 1-4 groups independently selected from $R^4$
(4) $C_{3-6}$alkynyl, which is unsubstituted or substituted with 1-4 groups independently selected from $R^4$,
(5) $C_{3-6}$cycloalkyl which is unsubstituted or substituted with 1-4 groups independently selected from $R^4$,
(6) phenyl, which is unsubstituted or substituted with 1-4 groups independently selected from $R^4$, and
(7) heterocycle, which is unsubstituted or substituted with 1-4 groups independently selected from $R^4$.

2. The compound of claim 1, or a pharmaceutically acceptable salt thereof, wherein $R^{1a}$, $R^{1b}$, and $R^{1c}$ are independently selected from the group consisting of:
(1) hydrogen,
(2) halogen,
(3) C(=O)$OC_{1-3}$alkyl,
(4) $C_{1-3}$alkyl, which is unsubstituted or substituted with 1-5 groups which are independently selected from halogen, hydroxyl and phenyl,
(5) —$OC_{1-3}$ alkyl, which is unsubstituted or substituted with 1-5 groups which are independently selected from halogen, hydroxyl and phenyl,
(6) —C(=O)OH,
(7) heteroaryl, wherein heteroaryl is triazolyl, tetrazolyl, oxazolyl, oxadiazolyl, pyrrolyl, pyrazolyl, imidazolyl, indolyl, pyridyl, or pyrimidinyl, and is unsubstituted or substituted with 1-3 groups which are independently selected from halogen, hydroxy, —$C_{1-3}$alkyl, —$OC_{1-3}$ alkyl, —CN, and —$NO_2$, wherein —$C_{1-3}$alkyl and —$OC_{1-3}$alkyl are optionally substituted with 1-3 halogens,
(8) phenyl, which is unsubstituted or substituted with 1-3 groups which are independently selected from halogen, hydroxy, —CN, —$CH_3$, —$CF_3$, —$OCH_3$, and —$OCF_3$, and
(9) $C_{3-6}$cycloalkyl, which is unsubstituted or substituted with 1-3 groups which are independently selected from halogen, hydroxyl, $C_{1-3}$alkyl, —$OC_{1-3}$alkyl, and —CN, wherein $C_{1-3}$alkyl, and —$OC_{1-3}$alkyl are optionally substituted with 1-3 halogens.

3. The compound of claim 2, or a pharmaceutically acceptable salt thereof, wherein $R^{1c}$ is H.

4. The compound of claim 2, or a pharmaceutically acceptable salt thereof, wherein $R^{1a}$ is attached to A in a position that is ortho to the carboxamide group connecting A to the rest of the compound, wherein $R^{1a}$ is selected from the group consisting of:
(1) heteroaryl that is triazolyl, pyrazolyl, tetrazolyl, or oxadiazolyl, wherein heteroaryl is optionally substituted with 1-3 groups which are independently $C_{1-3}$alkyl optionally substituted with 1-3 halogens, —$OC_{1-3}$alkyl optionally substituted with 1-3 halogens, or halogen,
(2) cyclopropyl, which is optionally substituted with 1-2 groups which are independently halogen, —CN, —$C_{1-2}$ alkyl, or —$OC_{1-2}$alkyl, wherein —$C_{1-2}$alkyl and —$OC_{1-2}$alkyl are optionally substituted with 1-3 halogens,
(3) phenyl, which is optionally substituted with 1-3 groups which are independently —CN, —$CH_3$, —$OCH_3$, —$CF_3$, or —$OCF_3$,
(4) —$C_{1-3}$alkyl, which is optionally substituted with 1-5 halogens,
(5) —$OC_{1-3}$alkyl, which is optionally substituted with 1-5 halogens,
(6) —C(=O)OH, and
(7) —C(=O)$OC_{1-2}$alkyl,
$R^{1b}$ is H, halogen, —$C_{1-3}$alkyl optionally substituted with 1-3 F, or —$OC_{1-3}$alkyl optionally substituted with 1-3 F, and
$R^{1c}$ is H.

5. The compound of claim 2 or a pharmaceutically acceptable salt thereof, wherein $R^3$ is selected from:
(1) $C_{1-3}$alkyl, which is optionally substituted with 1-5 substituent groups, which are independently selected from halogen, —OH, —$OCH_3$, and $C_{3-6}$ cycloalkyl,
(2) $C_{2-3}$alkenyl, which is optionally substituted with 1-5 halogens, and
(3) $C_{3-5}$ cycloalkyl.

6. The compound of claim 2, or a pharmaceutically acceptable salt thereof, wherein $R^5$ is —C($CH_3$)(OH)$C_{1-3}$ alkyl.

7. The compound of claim 2, or a pharmaceutically acceptable salt thereof, wherein $R^6$ is methyl.

8. The compound of claim 2, or a pharmaceutically acceptable salt thereof, wherein $R^{1a}$ is selected from the group consisting of:
(1) heteroaryl that is triazolyl, pyrazolyl, tetrazolyl, or oxadiazolyl, wherein heteroaryl is optionally substituted with 1-3 groups which are independently $C_{1-3}$alkyl optionally substituted with 1-3 halogens, —$OC_{1-3}$alkyl optionally substituted with 1-3 halogens, or halogen,
(2) cyclopropyl, which is optionally substituted with 1-2 groups which are independently —CN, —$C_{1-2}$alkyl, or —$OC_{1-2}$alkyl, wherein —$C_{1-2}$alkyl and —$OC_{1-2}$alkyl are optionally substituted with 1-3 halogens,
(3) phenyl, which is optionally substituted with 1-3 groups which are independently —CN, —$CH_3$, —$OCH_3$, —$CF_3$, or —$OCF_3$,
(4) —$C_{1-3}$alkyl, which is optionally substituted with 1-3 halogens,
(5) —$OC_{1-3}$alkyl, which is optionally substituted with 1-3 halogens,
(6) —C(=O)OH, and
(7) —C(=O)$OC_{1-2}$alkyl,
$R^{1b}$ is H, halogen, —$C_{1-3}$alkyl optionally substituted with 1-3 F, or —$OC_{1-3}$alkyl optionally substituted with 1-3 F,
$R^{1c}$ is H,
$R^3$ is selected from:
(1) $C_{1-3}$alkyl, which is optionally substituted with 1-3 F and optionally one group $C_{3-4}$ cycloalkyl, —OH, or —$OCH_3$,
(2) $C_{2-3}$alkenyl, and
(3) $C_{3-4}$cycloalkyl,
$R^5$ is —C($CH_3$)(OH)$C_{1-3}$alkyl, and
$R^6$ is methyl.

9. The compound of claim 1 having formula Ia, or a pharmaceutically acceptable salt thereof:

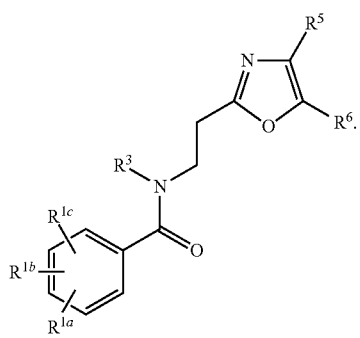
Ia
10. The compound of claim 1 having formula Ib, or a pharmaceutically acceptable salt thereof:
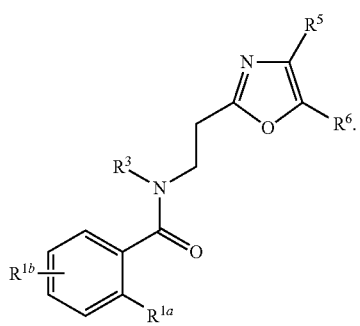
Ib
11. A compound which is selected from the group consisting of:
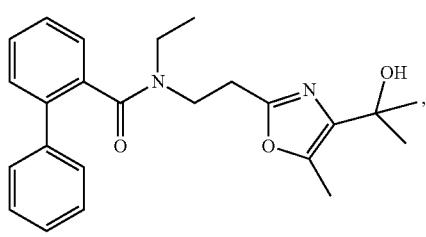
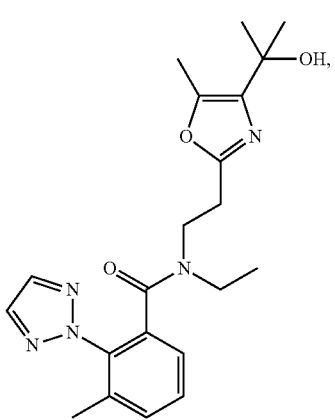
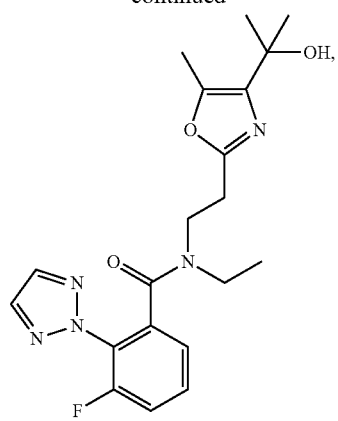
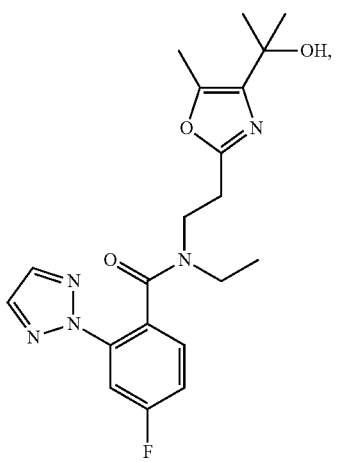
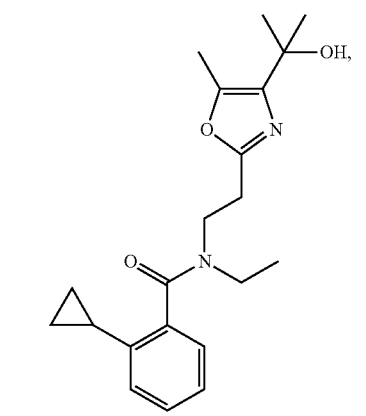
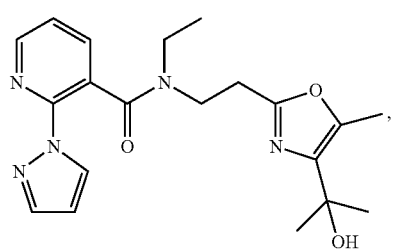

-continued

91
-continued
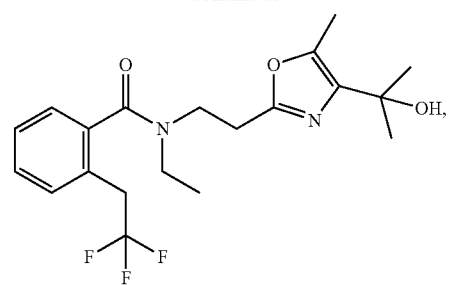
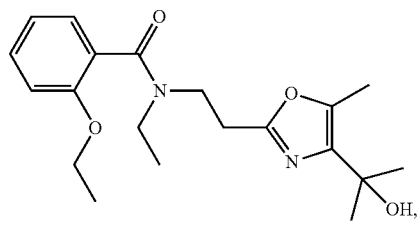
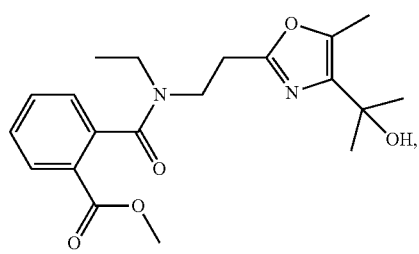
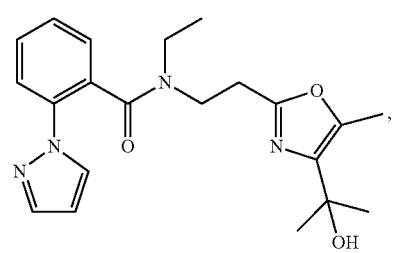
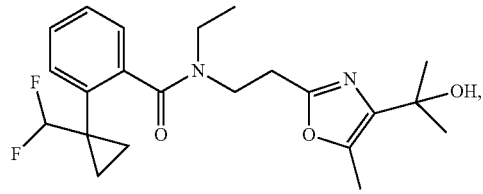
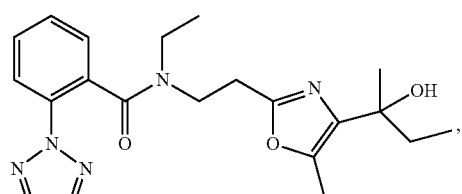
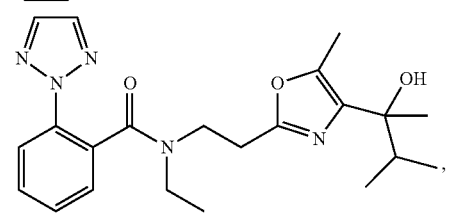
92
-continued
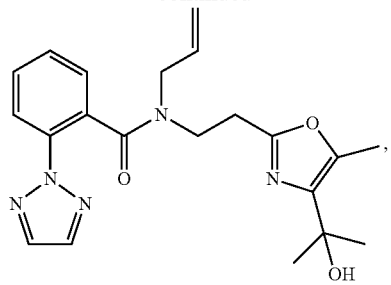
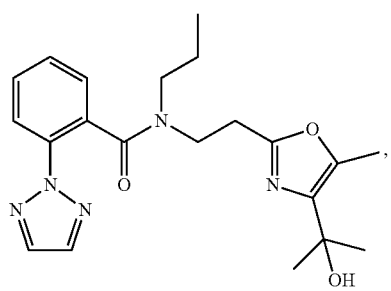
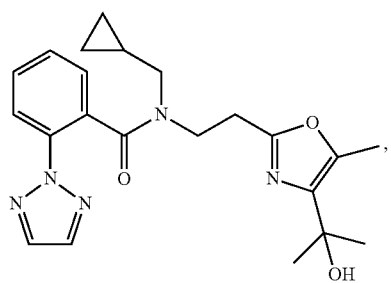
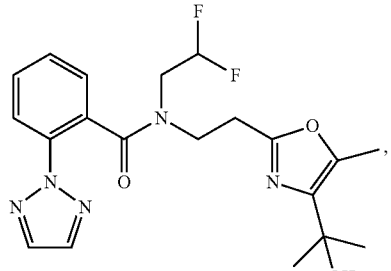
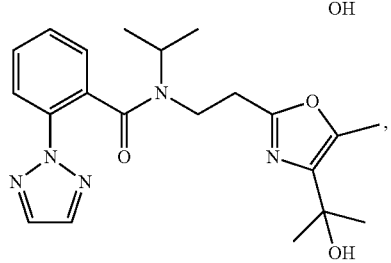
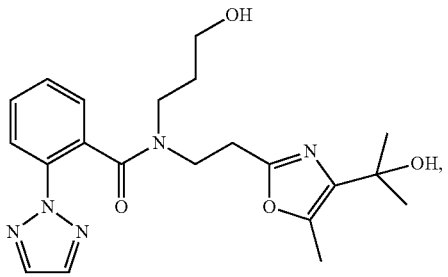

-continued

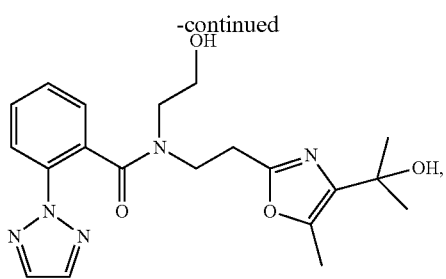

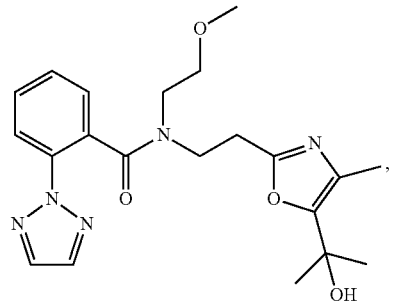

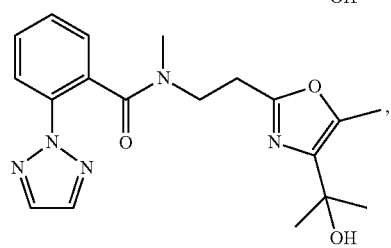

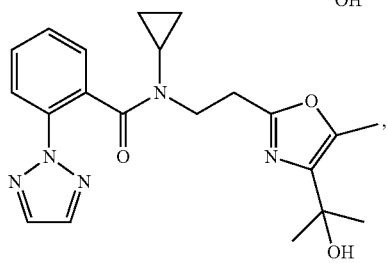

-continued

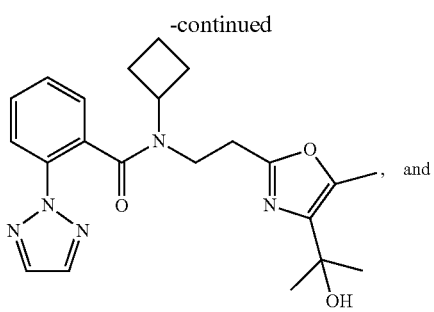
, and

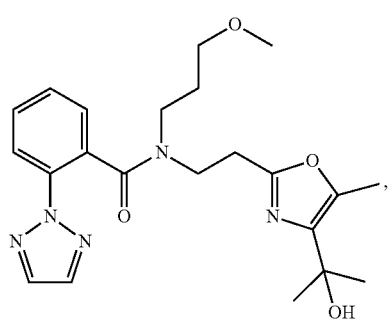

or a pharmaceutically acceptable salt thereof.

12. A pharmaceutical composition which comprises an inert carrier and a compound of claim 1, or a pharmaceutically acceptable salt thereof.

13. A method for enhancing the quality of sleep in a mammalian subject in need thereof which comprises administering to the subject a therapeutically effective amount of a compound of claim 1, or a pharmaceutically acceptable salt thereof.

* * * * *